US007161061B2

(12) United States Patent
Valentin et al.

(10) Patent No.: US 7,161,061 B2
(45) Date of Patent: Jan. 9, 2007

(54) METABOLITE TRANSPORTERS

(75) Inventors: Henry E. Valentin, Chesterfield, MO (US); Toni Voelker, Davis, CA (US); Wei Zheng, Davis, CA (US); Thomas J. Savage, Sacramento, CA (US)

(73) Assignee: Monsanto Technology LLC, St. Louis, MO (US)

( * ) Notice: Subject to any disclaimer, the term of this patent is extended or adjusted under 35 U.S.C. 154(b) by 659 days.

(21) Appl. No.: 10/141,478

(22) Filed: May 9, 2002

(65) Prior Publication Data

US 2003/0148300 A1    Aug. 7, 2003

Related U.S. Application Data

(63) Continuation-in-part of application No. 10/137,310, filed on May 3, 2002.

(60) Provisional application No. 60/289,519, filed on May 9, 2001, provisional application No. 60/289,527, filed on May 9, 2001.

(51) Int. Cl.
   C12N 15/82     (2006.01)
   C12N 15/29     (2006.01)
   A01H 5/00      (2006.01)
   A01H 5/10      (2006.01)
(52) U.S. Cl. ............... 800/278; 800/287; 800/306; 800/312; 435/468; 536/23.6
(58) Field of Classification Search ........... 536/23.1; 800/295; 435/320.1
   See application file for complete search history.

(56) References Cited

U.S. PATENT DOCUMENTS

| | | | |
|---|---|---|---|
| 4,727,219 A | 2/1988 | Brar et al. |
| 5,304,478 A | 4/1994 | Bird et al. |
| 5,429,939 A | 7/1995 | Misawa et al. |
| 5,432,069 A | 7/1995 | Grüninger et al. |
| 5,545,816 A | 8/1996 | Ausich et al. |
| 5,618,988 A | 4/1997 | Hauptmann et al. |
| 5,684,238 A | 11/1997 | Ausich et al. |
| 5,693,507 A | 12/1997 | Daniell et al. |
| 5,750,865 A | 5/1998 | Bird et al. |
| 5,792,903 A | 8/1998 | Hirschberg et al. |
| 5,876,964 A | 3/1999 | Croteau et al. |
| 6,281,017 B1 | 8/2001 | Croteau et al. |
| 6,303,365 B1 | 10/2001 | Martin et al. |
| 6,541,259 B1 | 4/2003 | Lassner et al. |
| 2002/0069426 A1 | 6/2002 | Boronat et al. |
| 2002/0108148 A1 | 8/2002 | Boronat et al. |
| 2003/0148300 A1 | 8/2003 | Valentin et al. |
| 2003/0150015 A1 | 8/2003 | Norris et al. |
| 2003/0154513 A1 | 8/2003 | van Eenennaam et al. |
| 2003/0166205 A1 | 9/2003 | van Eenennaam et al. |
| 2003/0170833 A1 | 9/2003 | Lassner et al. |
| 2003/0176675 A1 | 9/2003 | Valentin et al. |
| 2003/0213017 A1 | 11/2003 | Valentin et al. |
| 2004/0018602 A1 | 1/2004 | Lassner et al. |
| 2004/0045051 A1 | 3/2004 | Norris et al. |

FOREIGN PATENT DOCUMENTS

| | | |
|---|---|---|
| CA | 2339519 | 2/2000 |
| CA | 2343919 | 3/2000 |
| CA | 2372332 | 11/2000 |
| DE | 198 35 219 A1 | 8/1998 |
| EP | 0 531 639 A2 | 3/1993 |
| EP | 0 531 639 A3 | 3/1993 |
| EP | 0 674 000 A2 | 9/1995 |
| EP | 0 723 017 A2 | 7/1996 |
| EP | 0 763 542 A2 | 3/1997 |
| EP | 1 033 405 A2 | 9/2000 |
| EP | 1 063 297 A1 | 12/2000 |
| FR | 2 778 527 | 11/1999 |
| GB | 560529 | 4/1944 |
| WO | WO 91/02059 | 2/1991 |
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 4/1996 |
| WO | WO 96/13149 | 5/1996 |
| WO | WO 96/13159 | 5/1996 |
| WO | WO 96/36717 A2 | 11/1996 |
| WO | WO 96/36717 A3 | 11/1996 |

(Continued)

OTHER PUBLICATIONS

Geingenberger et al. Apr. 2001. Plant Physiol. vol. 125(4) pp. 1667-1678.*

(Continued)

Primary Examiner—David T. Fox
(74) Attorney, Agent, or Firm—Fulbright & Jaworski, L.L.P.

(57) ABSTRACT

The present invention is in the field of plant genetics and biochemistry. More specifically, the invention relates to genes associated with nucleotide triphosphate transport. The present invention provides and includes nucleic acid molecules, proteins, and antibodies associated with the genes involved in nucleotide triphosphate transport. The present invention also provides methods for utilizing such agents, for example, in gene isolation, gene analysis, and the production of transgenic plants. Moreover, the present invention includes transgenic plants modified to express proteins associated with nucleotide triphosphate transport.

38 Claims, 32 Drawing Sheets

FOREIGN PATENT DOCUMENTS

| | | |
|---|---|---|
| WO | WO 96/38567 | 12/1996 |
| WO | WO 97/17447 | 5/1997 |
| WO | WO 97/27285 | 7/1997 |
| WO | WO 97/49816 | 12/1997 |
| WO | WO 98/04685 | 2/1998 |
| WO | WO 98/18910 | 5/1998 |
| WO | WO 99/04021 | 1/1999 |
| WO | WO 99/04622 | 2/1999 |
| WO | WO 99/06580 | 2/1999 |
| WO | WO 99/07867 | 2/1999 |
| WO | WO 99/11757 | 3/1999 |
| WO | WO 99/19460 | 4/1999 |
| WO | WO 99/55889 | 11/1999 |
| WO | WO 99/58649 | 11/1999 |
| WO | WO 00/01650 | 1/2000 |
| WO | WO 00/08169 | 2/2000 |
| WO | WO 00/08187 | 2/2000 |
| WO | WO 00/11165 | 3/2000 |
| WO | WO 00/14207 | 3/2000 |
| WO | WO 00/17233 | 3/2000 |
| WO | WO 00/22150 A3 | 4/2000 |
| WO | WO 00/28005 | 5/2000 |
| WO | WO 00/34448 | 6/2000 |
| WO | WO 00/42205 A2 | 7/2000 |
| WO | WO 00/42205 A3 | 7/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/65036 A2 | 11/2000 |
| WO | WO 00/65036 A3 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 A2 | 11/2001 |
| WO | WO 01/88169 A3 | 11/2001 |
| WO | WO 02/26933 | 4/2002 |
| WO | WO 02/29022 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Schulz et al. 1998. Planta. vol. 206(4). pp. 553-543.*
Lazar et al. 1988. Mol. Cell. Biol. vol. 8. pp. 1247-1252.*
Hill et al. 1998. Biochem Biophys Res Comm 244. pp. 573-577.*
Guo et al. 2004. PNAS. USA. 101. p. 9205-9210.*
Saint-Guily et al. 1993. vol. 100. p. 1069-1071.*
Cahoon et al., "Production of fatty acid components of meadowfoam oil in somatic soybean embryos," Plant Physiology, 124:243-251, 2000.
Tjaden et al., "Altered plastidic ATP/ADP-transporter activity influences potato (Solanum tuberosum L.) tuber morphology yield and composition of tuber starch," The Plant Journal, 16(5):531-540, 1998.
Shewmaker et al., "Seed-specific overexpression of phytoene synthase: increase in carotenoids and other metabolic effects," The Plant Journal, 20(4):401-412, 1999.
Addlesee et al., "Cloning, sequencing and functional assignment of the chlorophyll biosyntheses gene, chlP, of Synechocystis sp. PCC 6803", FEBS Letters 389 (1996) 126-130.
Arango et al., "Tocopherol synthesis from homogentisate in Capsicum anuum L. (yellow pepper) chromoplast membranes: evidence for tocopherol cyclase", Biochem J., 336:531-533 (1998).
Baker et al., "Sequence and characterization of the gcpE gene of Escherichia coli", FEMS Microbiology Letters, 94:175-180 (1992).
Bayley et al., "Engineering 2,4-D resistance into cotton," Theor Appl Genet, 83:645-649 (1992).
Bentley, R., "The Shikimate Pathway—A Metabolic Tree with Many Branches," Critical Reviews™ in Biochemistry and Molecular Biology; vol. 25, Issue 5, 307-384 (1990).
Bevan, M., "Binary Agrobacterium vectors for plant transformation", Nucleic Acids Research, 12:8711-8721 (1984).
Beyer et al., "Phytoene-forming activities in wild-type and transformed rice endosperm," IRRN 21:2-3, p. 44-45 (Aug.-Dec. 1996).
Bork et al., "Go hunting in sequence databases but watch out for the traps", TIG 12, 10:425-427 (Oct. 1996).
Bramley et al., "Biochemical characterization of transgenic tomato plants in which carotenoid synthesis has been inhibited through the expression of antisense RNA to pTOM5," The Plant Journal, 2(3), 343-349 (1992).
Breitenbach et al., "Expression in Escherichia coli and properties of the carotene ketolase from Haematococcus pluvialis," FEMS Microbiology Letters 140, 241-246 (1996).
Broun et al., "Catalytic Plasticity of Fatty Acid Modification Enzymes Underlying Chemical Diversity of Plant Lipids," Science, 282:1315-1317 (1998).
Buckner et al., "The y1 Gene of Maize Codes for Phytoene Synthase," Genetics 143:479-488 (May 1996).
Burkhardt et al., "Genetic engineering of provitamin A biosynthesis in rice endosperm," Experientia, 818-821.
Burkhardt et al., "Transgenic rice (Oryza sativa) endosperm expressing daffodil (Narcissus pseudonarcissus) phytoene synthase accumulates phytoene, a key intermediate of provitamin A biosynthesis" The Plant Journal, 11(5), 1071-1078 (1997).
Cahoon et al., "Production of Fatty Acid Components of Meadowfoam Oil in Somatic Soybean Embryos," Plant Physiology, 124:243-251 (2000).
Chaudhuri et al., "The purification of shikimate dehydrogenase from Escherichia coli," Biochem. J., 226:217-223 (1985).
Cheng et al., "Highly Divergent Methyltransferases Catalyse a Conserved Reaction in Tocopherol and Plastoquinone Synthesis in Cyanobacteria and Photosynthetic Eukaryotes", The Plant Cell, 15:2343-2346 (2003).
Collakova et al., "Homogentisate Phytyltransferase Activity is Limiting for Tocopherol Biosynthesis in Arabidopsis", Plant Physiology, 131:632-642 (Feb. 2003).
Collakova et al., "Isolation and Characterization of Tocopherol Prenyl Transferase From Synechocystis and Arabidopsis", Poster Abstract see REN-01-026.
Cook et al., "Nuclear Mutations affecting plastoquinone accumulation in maize", Photosynthesis Research, 31:99-111 (1992).
Cunillera et al., "Characterization of dehydrodolichyl diphosphate synthase of Arabidopsis thaliana, a key enzyme in dolichol biosynthesis", FEBS Letters, 477:170-174 (2000).
d'Amato et al., "Subcellular localization of chorismate-mutase isoenzymes in protoplasts from mesophyll and suspension-cultured cells of Nicotiana silvestris," Planta, 162:104-108 (1984).
Doerks et al., "Protein annotation: detective work for function prediction", TIG, 14:248-250 (1998).
d'Harlingue et al., "Plastid Enzymes of Terpenoid Biosynthesis, Purification and Characterization of τTocopherol Methyltransferase from Capsicum Chromoplasts," The Journal of Biological Chemistry, vol. 260, No. 28, pp. 15200-15203, Dec. 5, 1985.
De Luca, Vincenzo, "Molecular characterization of secondary metabolic pathways", AgBiotech News and Information, 5(6):225N-229N (1993).
Duncan et al., "The overexpression and complete amino acid sequence of Escherichia coli 3-dehydroquinase", Biochem. J., 238:475-483 (1986).
Duvold et al., "Incorporation of 2-C-Methyl-D-erythritol, a Putative Isoprenoid Precursor in the Mevalonate-Independent Pathway, into Ubiquinone and Menaquinone of Escherichia coli", Tetrahedron Letters, 38(35):6181-6184 (1997).

Elliott, Thomas, "A Method for Constructing Single-Copy lac Fusions in *Salmonella typhimurium* and Its Application to the hemA-prfA Operon", Journal of Bacteriology, 174:245-253 (1992).

Ericson et al., "Analysis of the promoter region of napin genes from *Brassica napus* demonstrates binding of nuclear protein *in vitro* to a conserved sequence motif", Eur. J. Biochem., 197:741-746 (1991).

Estévez et al., "1-Deoxy-D-xylulose-5-phosphate Synthase, a Limiting Enzyme for Plastidic Isoprenoid Biosynthesis in Plants", The Journal of Biological Chemistry, 276(25):22901-22909 (2001).

Fellermeier et al., "Cell-free conversion of 1-deoxy-D-xylulose 5-phosphate and 2-C-methyl-D-erythritol 4-phosphate into β-carotene in higher plants and its inhibition by fosmidomycin", Tetrahedron Letters, 40:2743-2746 (1999).

Fourgoux-Nicol et al., "Isolation of rapeseed genes expressed early and specifically during development of the male gametophyte", Plant Molecular Biology, 40:857-872 (1999).

Fraser et al., "Enzymic confirmation of reactions involved in routes to astaxanthin formation, elucidated using a direct substrate *in vitro* assay", Eur. J. Biochem., 252:229-236 (1998).

Fraser et al., "*In Vitro* Characterization of Astaxanthin Biosynthetic Enzymes", the Journal of Biological Chemistry, 272(10) 6128-6135 (1997).

Fray et al., "Constitutive expression of a fruit phytoene synthase gene in transgenic tomatoes causes dwarfism by redirecting metabolites from the gibberellin pathway", The Plant Journal, 8(5):693-701 (1995).

Fray et al., "Identification and genetic analysis of normal and mutant phytoene synthase genes of tomato by sequencing, complementation and co-suppresion", Plant Molecular Biology, 22:589-602 (1993).

Fuqua et al., "Characterization of melA: a gene encoding melanin biosynthesis from the marine bacterium *Shewanella colwelliana*", Gene, 109:131-136 (1991).

Furuya et al., "Production of Tocopherols by Cell Culture of Safflower", Phytochemistry, 26(10):2741-2747 (1987).

Garcia et al., "Subcellular localization and purification of a ρhydroxyphenylpyruvate dioxygenase from cultured carrot cells and characterization of the corresponding cDNA", Biochem. J., 325:761-769 (1997).

Gaubier et al., "A chlorophyll synthetase gene from *Arabidopsis thaliana*", Mol. Gen. Genet., 249:58-64 (1995).

Goers et al., "Separation and characterization of two chorismate-mutase isoenzymes from *Nicotina silvestris*", Planta, 162:109-116 (1984).

Grabse et al., "Loss of α-tocopherol in tobacco plants with decreased geranylgeranyl reductase activity does not modify photosynthesis in optimal growth conditions but increases sensitivity to high-light stress", Planta, 213:620-628 (2001).

Harker et al., "Biosynthesis of ketocarotenoids in transgenic cyanobacteria expressing the algal gene for β-C-4-oxygenase, crtO", FEBS Letters, 404:129-134 (1997).

Harker et al., "Expression of prokaryotic 1-deoxy-D-xylulose-5-phosphatases in *Escherichia coli* increases carotenoid and ubiquinone biosynthesis", FEBS Letters, 448:115-119 (1999).

Hecht et al., "Studies of the nonmevalonate pathway to terpenes: The role of the GcpE (IspG) protein", PNAS, 98(26):14837-14842 (2001).

Herrmann, K.M., "The Shikimate Pathway as an Entry to Aromatic Secondary Metabolism", Plan Physiol., 107:7-12 (1995).

Kajiwara et al., "Isolation and functional identification of a novel cDNA for astaxanthin biosynthesis from *Haematococcus pluvialis*, and astaxanthin synthesis in *Escherichia coli*", Plant Molecular Biology, 29:343-352 (1995).

Kishore et al., "Amino Acid Biosynthesis Inhibitors as Herbicides", Ann. Rev. Biochem., 57:627-663 (1988).

Koziel et al., "Optimizing expression of transgenes with an emphasis on post-transcriptional events", Plant Molecular Biology, 32:393-405 (1996).

Kumagai et al., "Cytoplasmic inhibition of carotenoid biosynthesis with virus-derived RNA", Proc. Natl. Acad. Sci. USA, 92:1679-1683 (1995).

Kuntz et al., "Identification of a cDNA for the plastid-located geranylgeranyl pyrophosphate synthase from *Capsicum annuum*: correlative increase in enzyme activity and transcript level during fruit ripening", The Plant Journal, 2(1):25-34 (1992).

Lange et al., "Isoprenoid Biosyntheis via a Mevalonate-Independent Pathway in Plants: Cloning and Heterologous Expression of 1-Deoxy-D-xylulose-5-phosphate Reductoisomerase from Peppermint", Archives of Biochemistry and Biophysics, 365(1):170-174 (1999).

Li et al., "Identification of a maize endosperm-specific cDNA encoding famesyl pyrophosphate synthetase", Gene, 171:193-196 (1996).

Linthorst et al., "Constitutive Expression of Pathogenesis-Related Proteins PR-1, GRP, and PR-S in Tobacco Has No Effect on Virus Infection", The Plant Cell, 1:285-291 (1989).

Lopez et al., "Sequence of the bchG Gene from *Chloroflexus aurantiacus*: Relationship between Chlorophyll Synthase and other Polyprenyltransferases", Journal of Bacteriology, 178(11):3369-3373 (1996).

Lotan et al., "Cloning and expression in *Escherichia coli* of the gene encoding β-C-4-oxygenase, that converts β-carotene to the ketocarotenoid canthaxanthin in *Haematococcus pluvialis*", FEBS Letters, 364:125-128 (1995).

Mahmoud et al., "Metabolic engineering of essential oil yield and composition in mint by altering expression of deoxyxylulose phosphate reductoisomerase and menthofuran synthase", PNAS, 98(15):8915-8920 (2001).

Mandel et al., "CLA1, a novel gene required for chloroplast development, is highly conserved in evolution", The Plant Journal, 9(5):649-658 (1996).

Misawa et al., "Expression of an *Erwinia* phytoene desaturase gene not only confers multiple resistance to herbicides interfering with carotenoid biosynthesis but also alters xanthophyll metabolism in transgenic plants", The Plant Journal, 6(4):481-489 (1994).

Misawa et al., "Elucidation of the *Erwinia uredovora* Carotenoid Biosynthetic Pathway by Functional Analysis of Gene Products Expressed in *Escherichia coli*", Journal of Bacteriology, 172(12):6704-6712 (1990).

Misawa et al., "Functional expression of the *Ewinia uredovora* carotenoid biosynthesis gene crtl in transgenic plants showing an increase of β-carotene biosynthesis activity and resistance to the bleaching herbicide norflurazon", The Plant Journal, 4(5):833-840 (1993).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575-6584 (1995).

Nakamura et al., "Structural Analysis of *Arabidopsis thaliana* Chromosome 5. III. Sequence Features of the Regions of 1,191,918 bp Covered by Seventeen Physically Assigned P1 Clones", DNA Research, 4(6):401-414 (1997).

Oh et al., "Molecular Cloning, Expression, and Functional Analysis of a cis-Prenyltransferase from *Arabidopsis thaliana*", The Journal of Biological Chemistry, 275(24):18482-18488 (2000).

Oommen et al., "The Elicitor-Inducible Alfalfa Isoflavone Reductase Promoter Confers Different Patterns of Developmental Expression in Homologous and Heterologous Transgenic Plants", The Plant Cell, 6:1789-1803 (1994).

Oster et al., "The G4 Gene of *Arabidopsis thaliana* Encodes a Chlorophyll Synthase of Etiolated Plants", Bot. Acta, 110:420-423 (1997).

Peisker et al., "Phytol and the Breakdown of Chlorophyll in Senescent Leaves", J. Plant Physiol., 135:428-432 (1989).

Pompliano et al., "Probing Lethal Metabolic Perturbations in Plants with Chemical Inhibition of Dehydroquinate Synthase", J. Am. Chem. Soc., 111:1866-1871 (1989).

Porfirova et al., "Isolation of an *Arabidopsis* mutant lacking vitamin E and identification of a cyclase essential for all tocopherol biosynthesis", PNAS, 99(19):12495-12500 (2002).

Querol et al., "Functional analysis of the *Arabidopsis thaliana* GCPE protein involved in plastid isoprenoid biosynthesis", FEBS Letters, 514:343-346 (2002).

Rippert et al., "Molecular and biochemical characterization of an *Arabidopsis thaliana* arogenate dehydrogenase with two highly similar and active protein domains", Plant Mol. Biol., 48:361-368 (2002).

Rippert et al., "Engineering Plant Shikimate Pathway for Production of Tocotrienol and Improving Herbicide Resistance", Plant Physiology, 134:92-100 (2004).

Rodriguez-Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079-1089 (2002).

Rodriguez-Concepción et al., "1-Deoxy-D-xylulose 5-phosphate reductoisomerase and plastid isoprenoid biosynthesis during tomato fruit ripening", The Plant Journal, 27(3):213-222 (2001).

Römer et al., "Expression of the Genes Encoding the Early Carotenoid Biosynthetic Enzymes in *Capsicum Annuum*", Biochemical and Biophysical Research Communications, 196(3):1414-1421 (1993).

Ruzafa et al., "The protein encoded by the *Shewanella colwelliana melA* gene is a p-hydroxyphenylpyruvate dioxygenase", FEMS Microbiology Letters, 124:179-184 (1994).

Sandmann et al., "New functional assignment of the carotenogenic genes crtB and crtE with constructs of the genes from *Erwinia* species", FEMS Microbiology Letters, 90:253-258 (1992).

Sato et al., "Structural Analysis of *Arabidopsis thaliana* Chromosome 5. X. Sequence Features of the Regions of 3,076,755 bp Covered by Sixty P1 and TAC Clones", DNA Research, 7(1):31-63 (2000).

Savidge et al., "Isolation and Characterization of Homogentisate Phytyltransferase Genes from *Synechocystis* sp. PCC 6803 and *Arabidopsis*", Plant Physiology, 129:321-332 (2002).

Schwender et al., "Cloning and heterologous expression of a cDNA 1-deoxy-D-xylulose-5-phosphate reductoisomerase of *Arabidopsis thaliana*", FEBS Letters, 455:140-144 (1999).

Shewmaker et al., "Seed-specific overexpression of phytoene synthase: increase in carotenoids and other metabolic effects", The Plant Journal, 20(4):401-412 (1999).

Shigeoka et al., "Isolation and properties of γ-tocopherol methyltransferase in *Euglena gracilis*", Biochimica et Biophysica Acta, 1128:220-226 (1992).

Singh et al., "Chorismate Mutase Isoenzymes from *Sorghum bicolor*. Purification and Properties", Archives of Biochemistry and Biophysics, 243(2):374-384 (1985).

Smith, C.J.S. et al., "Antisense RNA inhibition of polygalacturonase gene expression in transgenic tomatoes", Nature, 334:724-726 (1998).

Smith, T.F. et al., "The challenges of genome sequence annotation or the devil is in the details", Nature Biotechnology, 15:1222-1223 (1997).

Soll et al., "Hydrogenation of Geranylgeraniol", Plant Physiol., 71:849-854 (1983).

Soll et al., "2-Methyl-6-Phytylquinol and 2,3-Dimethyl-5-Phytylquinol as Precursors of Tocopherol Synthesis in Spinach Chloroplasts", Phytochemistry, 19:215-218 (1980).

Spurgeon et al., "Biosynthesis of Isoprenoid Compounds", 1:1-45 (1981).

Stam et al.., "The Silence of Genes in Transgenic Plants", Annals of Botany, 79:3-12 (1997).

Stocker et al., "Identification of the Tocopherol-Cyclase in the Blue-Green Algae *Anabaena variabilis* Kützing (Cyanobacteria)", Helvetica Chimica Acta, 76:1729-1738 (1993).

Stocker et al., "The Substrate Specificity of Tocopherol Cyclase", Bioorganic & Medicinal Chemistry, 4(7):1129-1134 (1996).

Sun et al., "Cloning and Functional Analysis of the β-Carotene Hydroxylase of *Arabidopsis thaliana*", The Journal of Biological Chemistry, 271(40):24349-24352 (1996).

Suzich et al., "3-Deoxy-D-*arabino*-Heptulosonate 7-Phosphate Synthase from Carrot Root (*Daucus carota*) Is a Hysteretic Enzyme", Plant Physiol., 79:765-770 (1985).

Svab et al., "High-frequency plastid transformation in tobacco by selection for a chimeric aadA gene", Proc. Natl. Acad. Sci. USA, 90:913-917 (1993).

Svab et al., "Stable transformation of plastids in higher plants", Proc. Natl. Acad. Sci. USA, 87:8526-8530 (1990).

Takatsuji, H., "Zinc-finger transcription factors in plants", CMLS Cell. Mol. Life Sci., Birkhauser Verlag Basel CH, 54(6):582-596 (1998).

Tjaden et al., "Altered plastidic ATP/ADP-transporter activity influences potato (*Solanum tubersomum* L) tuber morphology, yield and composition of tuber starch", The Plant Journal, 16(5):531-540 (1998).

Town et al., "Whole genome shotgun sequencing of *Brassica oleracea*, BOGKS71TR BOGK *Brassica oleracea* genomic clone BOGKS71, DNA sequence", Database EMBL Accession No. BH534089 (Dec. 2001).

Town et al, "Whole genome shotgun sequencing of *Brassica oleracea*, BOGAU46TR BOGA *Brassica oleracea* genomic clone BOGAU46, DNA sequence", Database EMBL Accession No. BH248880 (Nov. 2001).

Verwoert et al., "Developmental specific expression and organelle targeting of the *Escherichia coli fabD* gene, encoding malonyl coenzyme A-acyl carrier protein transacylase in transgenic rape and tobacco seeds", Plant Molecular Biology, 26:189-202 (1994).

Yamamoto, E., "Purification and Metal Requirements of 3-Dehydroquinate Synthase from *Phaseolus Mungo* Seedlings", Phytochemistry, 19:779-781 (1980).

Zaka et al., "Changes in Carotenoids and Tocopherols During Maturation of *Cassia* Seeds", Pakistan J. Sci. Ind. Res., 30(11):812-814 (1987).

Zeidler et al., "Inhibition of the Non-Mevalonate 1-Deoxy-D-xylulose-5-phosphate Pathway of Plant Isoprenoid Biosynthesis by Fosmidomycin", A Journal of Biosciences, Zeitschrift fuer Naturforschung, Section C, 53(11/12):980-986 (Nov./Dec. 1998).

Zhu et al., "Geranylgeranyl pyrophosphate synthase encoded by the newly isolated gene GGPS6 from *Arabidopsis thaliana* is localized in mitochondria", Plant Molecular Biology, 35:331-341 (1997).

Zhu et al., "Cloning and Functional Expression of a Novel Geranylgeranyl Pyrophosphate Synthase Gene from *Arabidopsis thaliana* in *Escherichia coli*", Plant Cell Physiol., 38(3):357-361 (1997).

Kaneko et al., NCBI General Identifier No. 1001725, Accession No. BAA10562 (Feb. 2003).

Alcala et al., Genbank Accession No. AI 897027 (Jul. 1999).

Bevan et al., Database EMBL, Accession No. AL035394 (Feb. 1999).

Bevan et al., TREMBL Database Accession No. O65524 (Aug. 1998).

Campos et al., NCBI General Identifier BAA 18485, Database EMBL, Accession No. AF148852, (2000).

Chen et al., EMBL Sequence Database Accession No. AI995392 (Sep. 1999).

Desprez et al., Database EMBL, Accession No. Z34566 (Jun. 1994).

Fedenko et al., Abstract: RU 2005353, Derwent Accession No. 1994-253787.

Gaubier et al., Database EMBL, Accession No. Q38833 (Nov. 1996).

Kaneko et al., Database EMBL, Accession No. P73726 (Feb. 1997).

Kaneko et al., Database EMBL, Accession No. P73962 (Jul. 1998).

Kaneko et al., EMBL Sequence Database Accession No. D90909 (Oct. 1996).

Kaneko et al., TREMBL Database Accession No. P73727 (Feb. 1997).

Lange et al., "Mentha x Piperita 1-deoxy-D-xylulose-5-phosphate Reductoisomerase (DXR) mRNA", complete cds, Entrez Report, Accession No. AF116825 (Apr. 1999).

Lin et al., Database EMBL, Accession No. AC003672 (Dec. 1997).

Lin et al., Database EMBL, Accession No. AC003673 (Dec. 1997).

Lin et al., Database EMBL, Accession No. AC004077 (Feb. 1998).

Malakhov et al., Database TREMBL, Accession No. Q55207 (Nov. 1996).

Murata et al., EMBL Sequence Database Accession No. D13960 (Mar. 1996).

Nakamura et al., Database EMBL, Accession No. AB009053, Abstract (Dec. 1997) (1998)(2000).

Nakamura et al., Database EMBL, Accession No. AB005246 (Jul. 1997).
Newman et al., Database EMBL, Accession No. AA586087, Abstract (Sep. 1997).
Newman et al., Database EMBL, Accession No. R30625 (Aug. 1995).
Newman et al., Database EMBL, Accession No. T44803 (Feb. 1995).
Newman et al., DEBEST ID:1262303, Entrez Report, Accession No. AA586087 (Sep. 1997).
Oster et al., Database Biosis, Accession No. PREV199800047824 (Oct. 1997).
Ouyang et al., Database EMBL, Accession No. AF381248 (Jan. 2003).
Rounsley et al., Database EMBL, Accession No. B24116 (Oct. 1997).
Rounsley et al., Database EMBL, Accession No. B29398 (Oct. 1997).
Rounsley et al., Database TREMBL, Accession No. 064684 (Aug. 1998).
Schwender et al., *Arabidopsis thaliana* mRNA for Partial 1-deoxy-d-xylulose-5-phosphate Reductoisomerase (dxr gene), Entrez Report, Accession No. AJ242588 (Aug. 1999).
Scolnik et al., Database EMBL, Accession No. L40577 (Apr. 1995).
Shintani et al., Database NCBI, Accession No. AF104220 (Jan. 1999).
Shoemaker et al., Database EMBL, Accession No. AI748688 (Jun. 1999).
Shoemaker et al., Database EMBL, Accession No. AI938569 (Aug. 1999).
Shoemaker et al., Database EMBL, Accession No. AI988542 (Sep. 1999).
Shoemaker et al., Database EMBL, Accession No. AW306617 (Jan. 2000).
Tabata et al., Database EMBL, Accession No. D64001 (Sep. 1995).
Tabata et al., Database EMBL, Accession No. D64006 (Sep 1995).
Tabata et al., Database EMBL, Accession No. D90909 (Oct. 1996).
Tabata et al., Database EMBL, Accession No. D90911 (Oct. 1996).
Tabata et al., Database EMBL, Accession No. Q55145 (Nov. 1996).
Tabata et al., Database EMBL, Accession No. Q55500 (Nov. 1996).
Walbot, V., Database EMBL, Accession No. AI795655 (Jul. 1999).
Wing et al., Database EMBL, Accession No. AQ690643 (Jul. 1999).
Xia et al., Database EMBL, Accession No. M74133 (Jun. 1993).
Bevan et al., Accession T4 8445.
International Search Report, PCT/US00/10367, pp. 1-5 (Sep. 15, 2000).
International Search Report, PCT/US00/10368, pp. 1-14 (Jun. 15, 2001).
Written Opinion, PCT/US00/10368, pp. 1-6 (May 9, 2002).
IPER, PCT/US00/10368, pp. 1-5 (Aug. 16, 2002).
Examination Report, New Zealand Patent Application No. 514600, based on PCT/US/00/10368, pp. 1-2 (Apr. 24, 2003).
Communication pursuant to Article 96(2) EPC, EP Application 00922287.8, based on PCT/US00/10368, pp. 1-6 (Oct. 17, 2003).
Examiner's Report No. 2, Australia Patent Application No. 42492/00, based on PCT/US00/10368, pp. 1-4 (Nov. 12, 2003).
International Search Report, PCT/US01/12334, pp. 1-5 (Apr. 5, 2002).
International Search Report, PCT/US01/24335, 1-8 (Mar. 6, 2003).
International Search Report, PCT/US01/42673, pp. 1-4.
International Search Report, PCT/US02/03294, pp. 1-4 (Mar. 19, 2003).
International Search Report, PCT/US02/13898, pp. 1-3 (Sep. 13, 2002).
IPER, PCT/US02/13898, pp. 1-4 (Apr. 24, 2003).
International Search Report, PCT/US02/14445, pp. 1-6 (Oct. 30, 2003).
International Search Report, PCT/US02/26047, pp. 1-5 (Dec. 5, 2003).
International Search Report, PCT/US02/34079, pp. 1-5 (Jul. 28, 2003).
Written Opinion, PCT/US02/34079, pp. 1-4 (Oct. 23, 2003).

Response to Written Opinion, PCT/US02/34079, pp. 1-6 (Dec. 22, 2003).
Str 1736 cyanobase www.kazusa.com.
Ball, Fat-Soluble *Vitamin Assays in Food Analysis: A Comprehensive Review*, London, Elsevier Science Publishers, Ltd., 1988.
Buckley et al., "Influence of dietary vitamin E on the oxidative stability and quality of pig meat," *J of Animal Science*, 73:3122-3130, 1995.
Chen et al., "Functional analysis of regulatory elements in a plant embryo-specific gene," *Proc. Natl. Acad. Sci., USA*, 83(22):8560-8564, 1986.
Christou, In: *Particle Bombardment for the Genetic Engineering of Plants*, Biotechnology Intelligence Unit, Academic Press, San Diego, California, 1996.
Co-Pending U.S. Appl. No. 10/219,810, filed Aug. 16, 2002.
Co-Pending U.S. Appl. No. 10/279,029 filed Oct. 24, 2002.
Erin et al., "Formation of α-tocopherol complexes with fatty acids. Nature of complexes," *Biochim Biophys Acta*, , 815:209, 1995.
Fryer, "The antioxidant effects of thylakoid vitamin E (α-tocopherol)," *Plant Cell Environ*, 15(4):381-392, 1992.
Fukuzawa et al., "Antioxidant activities of tocopherols on $Fe^{2+}$-ascorbate-induced lipid peroxidation in lecithin liposomes," *Lipids*, 17:511-513, 1982.
Goossens et al., "The arcelin-5 Gene of *Phaseolus vulgaris* Directs High Seed-Specific Expression in Transgenic *Phaseolus acutifolius* and *Arabidopsis* Plants," *Plant Physiol*, 120:1095-1104, 1999.
Kridl et al., "Isolation and characterization of an expressed napin gene from *Brassica rapa*," *Seed Sci Res*, 1:209-219, 1991.
Peterson, "Oat tocols: concentration and stability on oat products and distribution within the kernel," *Cereal-Chem*, 72(1):21-24, 1995.
Radke et al., "Transformation and regeneration of *Brassica rapa* using *Agrobacterium tumefaciens*," *Plant Cell Reports*, 11:499-505, 1995.
Rohmer, *Comprehensive Natural Products Chemistry*, vol. 2, pp. 45-68, Barton Nakanishi eds, Pergamon Press, Oxford, England, 1999.
Sante and Lacourt, "The effect of dietary α-tocopherol supplementation and antioxidant spraying on colour stability and lipid oxidation of turkey meat," *J. Sci Food Agric*, 65(4):503-507, 1994.
Scolnik and Barley, "Nucleotide sequence of an *Arabidopsis* cDNA for geranylgeranyl pyrophosphate synthase," *Plant Physiol*, 104:1469-1470, 1994.
Taylor and Barnes, "Analysis for vitamin E in edible oils by high performance liquid chromatography," *Chemy Ind*, Oct.:722-726, 1981.
Trabor and Sies, "Vitamin E in humans: demand and delivery," *Annu Rev Nutr*, 16:321-347, 1996.
International Search Report, PCT/US02/13898, Sep. 13, 2002 (7 pages).
Collakova et al., "Isolation and Functional Analysis of Homogentisate Phytyltransferase from *Synechocystis* sp. PCC 6803 and *Arabidopsis*", *Plant Physiology*, vol. 127, pp. 1113-1124 (2001).
Norris et al., "Genetic Dissection of Carotenoid Synthesis in *Arabidopsis* Defines Plastoquinone as an Essential Component of Phytoene Desaturation", *The Plant Cell*, vol. 7, pp. 2139-2149 (1995).
Shintani et al., "Elevating the Vitamin E Content of Plants Through Metabolic Engineering", *SCIENCE*, vol. 282, pp. 2098-2100 (1998).
Xia et al., "The pheA/tyrAroF region from *Erwinia herbicola*: an emerging comparative basis for analysis of gene organization and regulation in enteric bacteria", Database GENBANK on STN, GenBank ACC. No. (GBN): M74133, *J. Mol. Evol.*, vol. 36, No. 2, pp. 107-120, Abstract (1993).
Arigoni et al., "Terpenoid biosynthesis from 1-deoxy-D-xylulose in higher plants by intramolecular skeletal rearrangement", *Proc. Natl. Acad. Sci. USA*, 94:10600-10605 (1997).
Bouvier et al., "Dedicated Roles of Plastid Transketolases during the Early Onset of Isoprenoid Biogenesis in Pepper Fruits", *Plant Physiol.*, 117:1423-1431 (1998).

Eisenreich et al., "The deoxyxylulose phosphate pathway of terpenoid biosynthesis in plants and microorganisms", *Chemistry & Biology*, 5(9):R221-R233 (1998).

Fiedler et al., "The formation of homogentisate in the biosynthesis of tocopherol and plastoquinone in spinach chloroplasts", *Planta*, 155:511-515 (1982).

Herz et al., "Biosynthesis of terpenoids: YgbB protein converts 4-diphosphocytidyl-2C-methyl-D-erythritol 2-phosphate to 2C-methyl-D-erythritol 2,4-cyclodiphosphate", *Proc. Natl. Acad. Sci. U.S.A.*, 97(6):2486-2490 (2000).

Kaneko et al., "Complete Genomic Sequence of the Filamentous Nitrogen-fixing Cyanobacterium *Anabaena* sp. Strain PCC 7120", *DNA Research*, 8(5): 205-213 (2001).

Keegstra, K., "Transport and Routing of Proteins into Chloroplasts", *Cell*, 56(2):247-53 (1989).

Keller et al., "Metabolic compartmentation of plastid prenyllip biosynthesis Evidence for the involvement of a multifunctional geranylgeranyl reductase" *Eur. J. Biochem.*, 251:413-417 (1998).

Lange et al., "A family of transketolases that directs isoprenoid biosynthesis via a mevalonate-independent pathway", *Proc. Natl. Acad. Sci. USA*, 95:2100-2104 (1998).

Lois et al., "Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis", *Proc. Natl. Acad. Sci. USA*, 95(5):2105-2110 (1998).

Marshall et al., "Biosynthesis of tocopherols: a re-examination of the biosynthesis and metabolism of 2-methyl-6-phytyl-1,4-benzoquinol", *Phytochemistry*, 24(8):1705-1711 (1985).

Nawrath et al., "Targeting of the polyhydroxybutyrate biosynthetic pathway to the plastids of *Arabidopsis thaliana* results in high levels of polymer accumulation", *Proc. Natl. Acad. Sci. U.S.A.*, 91:12760-12764 (1994).

NCBI General Identifier No. 1653572, Accession No. BAA18485.

Norris et al., "Complementation of the *Arabidopsis* pds1 Mutation with the Gene Encoding p-Hydroxyphenylpyruvate Dioxygenase", *Plant Physiology*, 117:1317-1323 (1998).

Okada et al., "Five Geranylgeranyl Diphosphate Synthases Expressed in Different Organs Are Localized into Three Subcellular Compartments in *Arabidopsis*", *Plant Physiology*, 122:1045-1056 (2000).

Rohdich et al., "Cytidine 5'-triphosphate-dependent biosynthesis of isoprenoids: YgbP protein of *Escherichia coli* catalyzes the formation of 4-diphosphocytidyl-2-C-methylerythritol", *Proc. Natl. Acad. Sci. USA*, 96(21):11758-11763 (1999).

Rohmer et al., "Glyceraldehyde 3-Phosphate and Pyruvate as Precursors of Isoprenic Units in an Alternative Non-mevalonate Pathway for Terpenoid Biosynthesis", *J. Am. Chem. Soc.*, 118:2564-2566 (1996).

Rohmer et al., "Isoprenoid biosynthesis in bacteria: a novel pathway for the early steps leading to isopentenyl diphosphate", *Biochem. J.*, 295:517-524 (1993).

Rohmer, M., "Isoprenoid biosynthesis via the mevalonate-independent route, a novel target for antibacterial drugs?", *Progress in Drug Research*, 50:136-154 (1998).

Rohmer, M., "A Mevalonate-independent Route to Isopentenyl Diphosphate", *Comprehensive Natural Products Chemistry*, 2:45-67 (1999).

Saint-Guily et al., "Complementary DNA Sequence of an Adenylate Translocator from *Arabidopsis thaliana*", *Plant Physiology*, 100(2):1069-1071 (1992).

Sato et al., "Structural Analysis of *Arabidopsis thaliana* Chromosome 5. X. Sequence Features of the Regions of 3,076,755 bp Covered by Sixty P1 and TAC Clones", *DNA Research*, 7(1):31-63 (2000).

Scolnik and Bartley, "Nucleotide Sequence of an *Arabidopsis* cDNA for Geranylgeranyl Pyrophosphate Synthase", *Plant Physiology*, 104(4):1469-1470 (1994).

Smith et al., "The cloning of two *Arabidopsis* genes belonging to a phosphate transporter family", *Plant Journal*, 11(1):83-92 (1997).

Soll et al., "Tocopherol and Plastoquinone Synthesis in Spinach Choroplasts Subfractions", *Arch. Biochem. Biophys.* 204(2):544-550 (1980).

Sprenger et al., "Identification of a thiamin-dependent synthase in *Escherichia coli* required for the formation of the 1-deoxy-D-xylulose 5-phosphate precursor to isoprenoids, thiamin, and pyridoxol", *Proc. Natl. Acad. Sci. USA*, 94:12857-12862 (1997).

Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis", *Proc. Natl. Acad. Sci. U.S.A.*, 95(17), 9879-9884 (1998).

Xia et al., "A monofunctional prephenate dehydrogenase created by cleavage of the 5' 109 bp of the tyrA gene from *Erwinia herbicola*", *J. Gen. Microbiol.* 138(7):1309-1316 (1992).

Bowie et al., "Deciphering the Message in Protein Sequences: Tolerance to Amino Acid Substitutions", Science, 247:1306-1310 (1990).

McConnell et al., "Role of *Phabulosa* and *Phavoluta* in determining radial patterning in shoots", Nature, 411(6838): 709-713 (2001).

Baker et al., NCBI Accession No. X64451 (Dec. 1993).

* cited by examiner

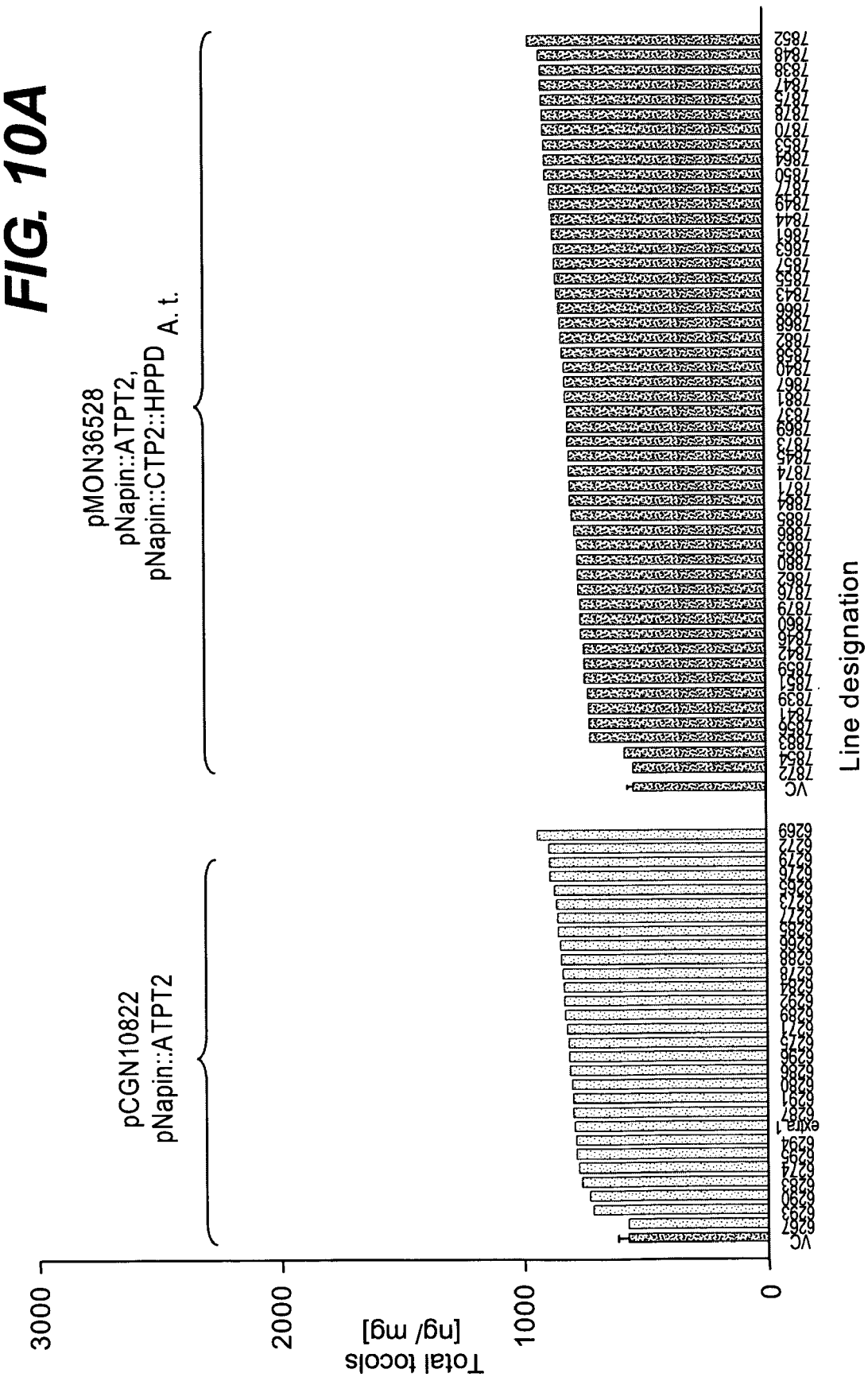

METABOLITE TRANSPORTERS

CROSS-REFERENCE TO RELATED APPLICATION

This application claims the benefit of and priority to U.S. Provisional Application No. 60/289,519, filed May 9, 2001, this application is also a continuation-in-part of U.S. application Ser. 10/137,310, filed May 3, 2002, which claims priority to U.S. Provisional Application No. 60/289,527, filed May 9, 2001. The content of each of the foregoing applications is herein incorporated by reference in its entirety.

FIELD OF THE INVENTION

The present invention is in the field of plant genetics and biochemistry. More specifically, the invention relates to genes associated with nucleotide triphosphate transport. The present invention provides and includes nucleic acid molecules, proteins, and antibodies associated with the genes involved in nucleotide triphosphate transport. The present invention also provides methods for utilizing such agents, for example in gene isolation, gene analysis and the production of transgenic plants. Moreover, the present invention includes transgenic plants modified to express proteins associated with nucleotide triphosphate transport.

BACKGROUND OF THE INVENTION

Tocopherols are an essential component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.* 16:321–347 (1996)). Tocopherol functions, in part, by stabilizing the lipid bilayer of biological membranes (Skrypin and Kagan, *Biochim. Biophys. Acta* 815:209 (1995); Kagan, *N. Y. Acad. Sci.* p 121, (1989); Gomez-Fernandez et al., *Ann. N. Y. Acad. Sci.* p 109 (1989)), reducing polyunsaturated fatty acid (PUFA) free radicals generated by lipid oxidation (Fukuzawa et al., *Lipids* 17: 511–513 (1982)), and scavenging oxygen free radicals, lipid peroxy radicals, and singlet oxygen species (Diplock et al., *Ann. N. Y. Acad. Sci.* 570: 72 (1989); Fryer, *Plant Cell Environ.* 15(4):381–392 (1992)).

α-Tocopherol, often referred to as vitamin E, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "vitamin E," vitamin E is more appropriately defined chemically as α-tocopherol. α-Tocopherol is significant for human health, in part because it is readily absorbed and retained by the body, and has a higher degree of bioactivity than other tocopherol species (Traber and Sies, *Annu. Rev. Nutr.* 16:321–347 (1996)). However, other tocopherols such as β, γ, and δ-tocopherols, also have significant health and nutritional benefits.

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10–50 μg of total tocopherols per gram fresh weight, but most of the world's major staple crops (e.g., rice, maize, wheat, potato) produce low to extremely low levels of total tocopherols, of which only a small percentage is α-tocopherol (Hess, Vitamin E, α-tocopherol, In *Antioxidants in Higher Plants*, R. Alscher and J. Hess, Eds., CRC Press, Boca Raton. pp. 111–134 (1993)). Oil seed crops generally contain much higher levels of total tocopherols, but α-tocopherol is present only as a minor component (Taylor and Barnes, *Chemy Ind.*, Oct.:722–726 (1981)).

The recommended daily dietary intake of 15–30 mg of vitamin E is quite difficult to achieve from the average American diet. For example, it would take over 750 grams of spinach leaves, in which α-tocopherol comprises 60% of total tocopherols, or 200–400 grams of soybean oil to satisfy this recommended daily vitamin E intake. While it is possible to augment the diet with supplements, most of these supplements contain primarily synthetic vitamin E, having six stereoisomers, whereas natural vitamin E is predominantly composed of only a single isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocpherols, increased α-tocopherol levels in crops have been associated with enhanced stability and extended shelf life of plant products (Peterson, *Cereal-Chem* 72(1):21–24 (1995); Ball, *Fat-soluble vitamin assays in food analysis. A comprehensive review*, London, Elsevier Science Publishers Ltd. (1988)). Further, tocopherol supplementation of swine, beef, and poultry feeds has been shown to significantly increase meat quality and extend the shelf life of post-processed meat products by retarding post-processing lipid oxidation, which contributes to undesirable flavor components (Sante and Lacourt, *J. Sci. Food Agric.* 65(4):503–507 (1994); Buckley et al., *J. of Animal Science* 73:3122–3130 (1995)).

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methyl-6 phytylplastoquinol (Fiedler et al., *Planta* 155: 511–515 (1982); Soll et al., *Arch. Biochem. Biophys.* 204: 544–550 (1980); Marshall et al., *Phytochem.* 24: 1705–1711 (1985)). This plant tocopherol pathway can be divided into four parts: 1) synthesis of homogentistic acid, which contributes to the aromatic ring of tocopherol; 2) synthesis of phytylpyrophosphate, which contributes to the side chain of tocopherol; 3) cyclization, which plays a role in chirality and chromanol substructure of the vitamin E family; 4) and S-adenosyl methionine dependent methylation of an aromatic ring, which affects the relative abundance of each of the tocopherol species.

Synthesis of Homogentistic Acid

Homogentisic acid is the common precursor to both tocopherols and plastoquinones. In at least some bacteria the synthesis of homogentesic acid is believed to occur via the conversion of chorismate to prephenate and then to p-hydroxyphenyl-pyruvate via a bifunctional prephenate dehydrogenase. Examples of bifunctional bacterial prephenate dehydrogenase enzymes include the proteins encoded by the TyrA genes of *Erwinia herbicola* and *Escherichia coli*. The TyrA gene product catalyzes the production of prephenate from chorismate, as well as the subsequent dehydrogenation of prephenate to form p-hydroxyphenylpyruvate (p-HPP), the immediate precursor to homogentistic acid. p-HPP is then converted to homogentistic acid by hydroxyphenylpyruvate dioxygenase (HPPD). In contrast, plants are reported to lack prephenate dehydrogenase activity, and it is further reported that the synthesis of homogentesic acid from chorismate occurs via the synthesis and conversion of the intermediate arogenate. Since pathways involved in homogentesic acid synthesis are also responsible for tyrosine formation, any alterations in these pathways can also result in the alteration in tyrosine synthesis and the synthesis of other aromatic amino acids.

Synthesis of Phytylpyrophosphate

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221-R233 (1998); Rohmer, *Prog. Drug. Res.*, 50:135–154 (1998); Rohmer, *Comprehensive Natural Products Chemistry*, Vol. 2, pp. 45–68, Barton and Nakanishi (eds.), Pergamon Press, Oxford, England (1999)), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate in the novel pathway, now referred to as the MEP pathway (Rohmer et al., *Biochem. J.*, 295:517–524 (1993); Schwarz, Ph.D. thesis, Eidgenössiche Technische Hochschule, Zurich, Switzerland (1994)). Recent studies showed the formation of 1-deoxyxylulose 5-phosphate (Broers, Ph.D. thesis (Eidgenössiche Technische Hochschule, Zurich, Switzerland) (1994)) from one molecule each of glyceraldehyde 3-phosphate (Rohmer, *Comprehensive Natural Products Chemistry*, Vol. 2, pp. 45–68, Barton and Nakanishi, eds., Pergamon Press, Oxford, England (1999)) and pyruvate (Eisenreich et al., *Chem. Biol.*, 5:R223–R233 (1998); Schwarz supra; Rohmer et al., *J. Am. Chem. Soc.*, 118:2564–2566 (1996); and Sprenger et al., *Proc. Natl. Acad. Sci. USA*, 94:12857–12862 (1997)) by an enzyme encoded by the dxs gene (Lois et al., *Proc. Natl. Acad. Sci. USA*, 95:2105–2110 (1997); and Lange et al., *Proc. Natl. Acad. Sci. USA*, 95:2100–2104 (1998)). 1-Deoxyxylulose 5-phosphate can be further converted into 2-C-methylerythritol 4-phosphate (Arigoni et al., *Proc. Natl. Acad. Sci. USA*, 94:10600–10605 (1997)) by a reductoisomerase catalyzed by the dxr gene (Bouvier et al., *Plant Physiol*, 117:1421–1431 (1998); and Rohdich et al., *Proc. Natl. Acad. Sci. USA*, 96:11758–11763 (1999)).

Reported genes in the MEP pathway also include ygbP, which catalyzes the conversion of 2-C-methylerythritol 4-phosphate into its respective cytidyl pyrophosphate derivative and ygbB, which catalyzes the conversion of 4-phosphocytidyl-2C-methyl-D-erythritol into 2C-methyl-D-erythritol, 3, 4-cyclophosphate. These genes are tightly linked on the E. coli genome (Herz et al., *Proc. Natl. Acad. Sci. U.S.A.*, 97(6):2485–2490 (2000)).

Once IPP is formed by the MEP pathway, it is converted to GGDP by GGDP synthase, and then to phytylpyrophosphate, which is the central constituent of the tocopherol side chain.

Combination and Cyclization

Homogentisic acid is combined with either phytyl-pyrophosphate or solanyl-pyrophosphate by phytyl/prenyl transferase forming 2-methyl-6-phytyl plastoquinol or 2-methyl-6-solanyl plastoquinol respectively. 2-methyl-6-solanyl plastoquinol is a precursor to the biosynthesis of plastoquinones, while 2-methyl-6-phytyl plastoquinol is ultimately converted to tocopherol.

Methylation of the Aromatic Ring

A major structural difference between each of the tocopherol subtypes is the position of the methyl groups around the phenyl ring. Both 2-methyl-6-phytyl plastoquinol and 2-methyl-6-solanyl plastoquinol serve as substrates for 2-methyl-6-phytylplatoquinol/2-methyl-6-solanylplastoquinol-9 methyltransferase (Methyl Transferase 1; MT1), which catalyzes the formation of plastoquinol-9 and γ-tocopherol respectively, by methylation of the 7 position. Subsequent methylation at the 5 position of γ-tocopherol by γ-methyl-transferase generates the biologically active α-tocopherol.

Energy Requirements

Production of tocopherols is extremely expensive in terms of the amount of energy required to generate adequate tocopherol levels. Adenylate transporters supply nucleotide triphosphates (including ATP and CTP) into the cell or cellular compartment for use in biosynthetic or metabolic processes. A putative adenylate transporter sequence from *Arabidopsis thaliana* has been reported in the literature (Saint Guily, et al., *Plant Physiol.*, 100(2):1069–1071 (1992)).

There is a need in the art for nucleic acid molecules encoding enzymes involved in nucleotide triphosphate transport, as well as related enzymes and antibodies for the enhancement or alteration of tocopherol production in plants. There is a further need for transgenic organisms expressing those nucleic acid molecules involved in nucleotide triphosphate transport, which are capable of nutritionally enhancing food and feed sources.

SUMMARY OF THE INVENTION

The present invention includes and provides a substantially purified nucleic acid molecule that encodes an adenylate transporter, wherein the nucleic acid molecule comprises SEQ ID NO: 1.

The present invention includes and provides a nucleic acid molecule which comprises: (A) a promoter region which functions in a plant cell to cause the production of a mRNA molecule; (B) an exogenous structural nucleic acid molecule encoding a protein or fragment thereof comprising an amino acid sequence of SEQ ID NO: 2; and (C) a 3' non-translated sequence that functions in the plant cell to cause termination of transcription and addition of polyadenylated ribonucleotides to a 3' end of the mRNA molecule.

The present invention includes and provides a nucleic acid molecule which comprises a substantially purified nucleic acid molecule comprising as operably linked components: (A) a promoter region which functions in a plant cell to cause the production of an mRNA molecule; (B) a nucleic acid sequence that encodes an adenylate transporter or a fragment there of; wherein the purified nucleic acid molecule further comprises one or more expression cassettes, each of which expresses a member selected from the group consisting of slr1736, ATPT2, dxs, dxr, GGH, GGPPS, HPPD, MT1, TMT2, GMT, slr 1737, and an antisense construct for homogentisic acid dioxygenase.

The present invention includes and provides a transgenic plant comprising a substantially purified nucleic acid molecule comprising as operably linked components: (A) a promoter region which functions in a plant cell to cause the production of an mRNA molecule; (B) a nucleic acid sequence that encodes an adenylate transporter or a fragment thereof; wherein the purified nucleic acid molecule further comprises one or more expression cassettes, each of which expresses a member selected from the group consisting of slr1736, ATPT2, dxs, dxr, GGH, GGPPS, HPPD, MT1, TMT2, GMT, slr 1737, and an antisense construct for homogentisic acid dioxygenase.

The present invention includes and provides a substantially purified protein comprising SEQ ID NO: 2.

The present invention includes and provides an antibody capable of specifically binding a substantially purified protein comprising SEQ ID NO: 2.

The present invention includes and provides a transformed plant having an exogenous nucleic acid molecule that encodes an adenylate transporter, wherein the nucleic acid molecule comprises an *Arabidopsis* nucleic acid sequence.

The present invention includes and provides a transformed plant having an exogenous nucleic acid molecule which comprises a nucleic acid sequence that encodes for a protein having an amino acid sequence of SEQ ID NO: 2.

The present invention includes and provides a transformed plant having an exogenous nucleic acid molecule that comprises a nucleic acid sequence SEQ ID NO: 1.

The present invention includes and provides a method of producing a plant having seeds with increased tocopherol level comprising: (a) transforming the plant with a nucleic acid molecule that encodes an adenylate transporter; and (b) growing the transformed plant.

The present invention includes and provides a method of producing a plant having seeds with increased tocopherol level comprising: (a) transforming the plant with a nucleic acid molecule which comprises a nucleic acid sequence that encodes for a protein having an amino acid sequence of SEQ ID NO: 2; and (b) growing the transformed plant.

The present invention includes and provides a method of producing a plant having seeds with an increased tocopherol level comprising: (A) transforming the plant with a nucleic acid molecule, wherein the nucleic acid molecule comprises SEQ ID NO: 1; and (B) growing the plant.

The present invention includes and provides a seed derived from a transformed plant having an exogenous nucleic acid molecule that encodes an adenylate transporter, wherein the seed has an increased tocopherol level relative to seeds from a plant having a similar genetic background but lacking the exogenous nucleic acid molecule.

The present invention includes and provides a seed derived from a transformed plant has an exogenous nucleic acid molecule which comprises a nucleic acid sequence that encodes for a protein having an amino acid sequence of SEQ ID NO: 2, wherein the seed has an increased tocopherol level relative to seeds from a plant having a similar genetic background but lacking the exogenous nucleic acid molecule.

The present invention includes and provides a seed derived from a transformed plant having an exogenous nucleic acid molecule comprising SEQ ID NO: 1, wherein the seed has an increased tocopherol level relative to seeds from a plant having a similar genetic background but lacking the exogenous nucleic acid molecule.

The present invention includes and provides oil derived from a seed of a transformed plant having an exogenous nucleic acid molecule that encodes an adenylate transporter, wherein the transformed plant has a seed with an increased tocopherol level relative to seeds from a plant having a similar genetic background but lacking the exogenous nucleic acid molecule.

The present invention includes and provides oil derived from a seed of a transformed plant having an exogenous nucleic acid molecule which comprises a nucleic acid sequence that encodes for a protein having an amino acid sequence of SEQ ID NO: 2, wherein the transformed plant has a seed with an increased tocopherol level relative to seeds from a plant having a similar genetic background but lacking the exogenous nucleic acid molecule.

The present invention includes and provides oil derived from a seed of a transformed plant, wherein the transformed plant contains an exogenous nucleic acid molecule comprising a nucleic acid sequence comprising SEQ ID NO: 1.

The present invention includes and provides feedstock comprising a transformed plant or part thereof having an exogenous nucleic acid molecule that encodes an adenylate transporter, wherein the transformed plant has a seed with an increased tocopherol level relative to seeds from a plant having a similar genetic background but lacking the exogenous nucleic acid molecule.

The present invention includes and provides feedstock comprising a transformed plant or part thereof having an exogenous nucleic acid molecule which comprises a nucleic acid sequence that encodes for a protein having an amino acid sequence of SEQ ID NO: 2, wherein the transformed plant has a seed with an increased tocopherol level relative to seeds from a plant having a similar genetic background but lacking the exogenous nucleic acid molecule.

The present invention includes and provides feedstock comprising a transformed plant or part thereof, wherein the transformed plant has an exogenous nucleic acid molecule that comprises a nucleic acid sequence comprising SEQ ID NO: 1.

The present invention includes and provides a meal comprising plant material manufactured from a transformed plant having an exogenous nucleic acid molecule that encodes an adenylate transporter, wherein the transformed plant has a seed with an increased tocopherol level relative to seeds from a plant having a similar genetic background but lacking the exogenous nucleic acid molecule.

The present invention includes and provides a meal comprising plant material manufactured from a transformed plant having an exogenous nucleic acid molecule which comprises a nucleic acid sequence that encodes for a protein having an amino acid sequence of SEQ ID NO: 2, wherein the transformed plant has a seed with an increased tocopherol level relative to seeds from a plant having a similar genetic background but lacking the exogenous nucleic acid molecule.

The present invention includes and provides a meal comprising plant material manufactured from a transformed plant, wherein the transformed plant has an exogenous nucleic acid molecule that comprises a nucleic acid sequence comprising SEQ ID NO: 1.

DESCRIPTION OF THE NUCLEIC AND AMINO ACID SEQUENCES

SEQ ID NO: 1 sets forth a nucleic acid sequence of a cDNA molecule which encodes an *Arabidopsis thaliana* adenylate transporter.

SEQ ID NO: 2 sets forth a derived amino acid sequence of an *Arabidopsis thaliana* adenylate transporter.

SEQ ID NO: 3 sets forth a forward primer for amplification of the AANT1 gene.

SEQ ID NO: 4 sets forth a reverse primer for amplification of the AANT 1 gene.

DETAILED DESCRIPTION OF THE INVENTION

Figure 1:
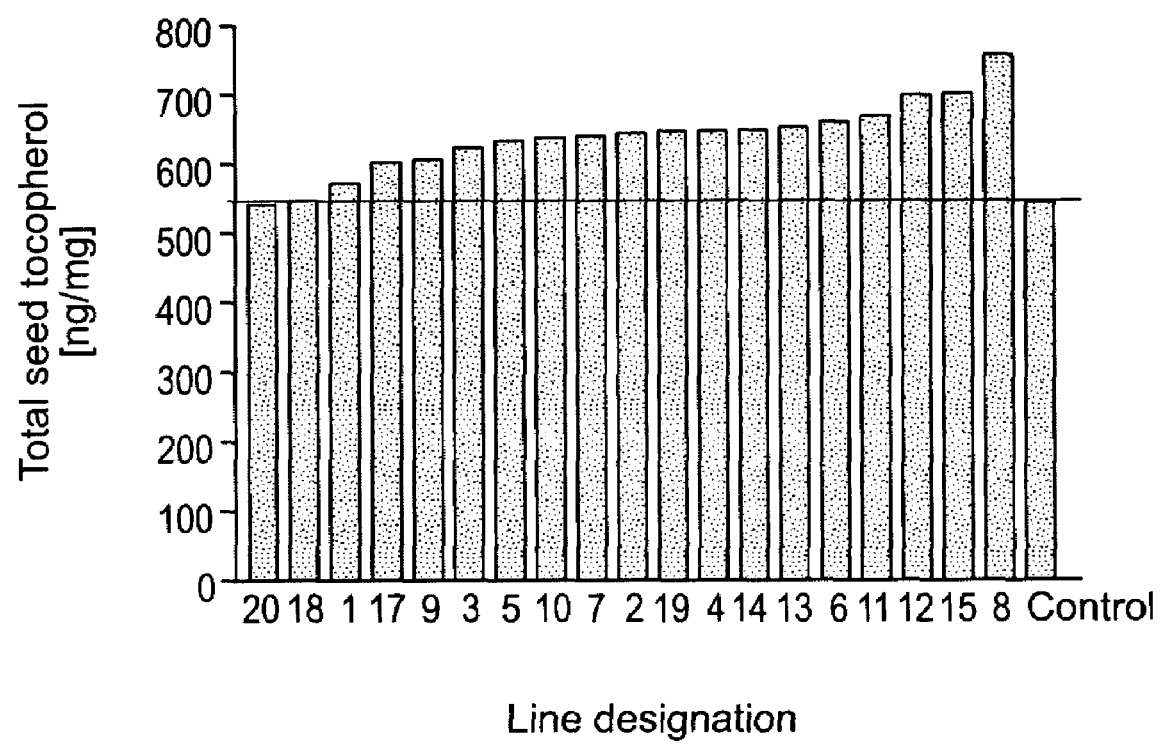
FIG. 1 is a graph comparing total seed tocopherol levels (nanograms per milligram) for 20 plant lines expressing a metabolite transporter gene under napin promoter control and a plant with a vector control.

The present invention provides a number of agents, for example, nucleic acid molecules and proteins associated with adenylate translocation, and provides uses of such agents.

Agents

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the invention may also be "recombinant." As used herein, the term "recombinant" means any agent (e.g., DNA, peptide etc.), that is, or results from, however indirectly, human manipulation of a nucleic acid molecule.

In some embodiments of the present invention, a cell, organism, or plant may have a phenotype that is altered relative to a similar cell, organism, or plant having a "similar genetic background." In a preferred aspect, a "similar genetic background" is a background where the organisms being compared share 50% or greater of their nuclear genetic material. In a more preferred aspect, a similar genetic background is a background where the organisms being compared share 75% or greater, even more preferably 90% or greater, of their nuclear genetic material. In another even more preferable aspect, a similar genetic background is a background where the organisms being compared are plants, and the plants are isogenic except for any genetic material originally introduced using plant transformation techniques.

It is understood that the agents of the invention may be labeled with reagents that facilitate detection of the agent (e.g., fluorescent labels, Prober et al., *Science* 238:336–340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

(a) Nucleic Acid Molecules

Agents of the invention include nucleic acid molecules. In a preferred aspect of the present invention the nucleic acid molecule comprises a nucleic acid sequence which encodes an adenylate transporter. As used herein an "adenylate transporter" is any protein that is a nucleotide transporter. A preferred adenylate transporter is a plant adenylate transporter, more preferably an *Arabidopis thaliana* adenylate transporter. An example of a more preferred *Arabidopis thaliana* adenylate transporter is a protein with the amino acid set forth in SEQ ID NO: 2.

In another preferred aspect of the present invention the nucleic acid molecule comprises a nucleic acid sequence of SEQ ID NO: 1, complements thereof, and fragments of either. In a further aspect of the present invention the nucleic acid molecule comprises a nucleic acid sequence encoding an amino acid sequence of SEQ ID NO: 2 and fragments thereof.

It is understood that in a further aspect of the present invention, nucleic acids can encode a protein that differs from any of the proteins in that one or more amino acids have been deleted, substituted, or added without altering the function. For example, it is understood that codons capable of coding for such conservative amino acid substitutions are known in the art.

One subset of the nucleic acid molecules of the invention is fragment nucleic acid molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A preferred fragment nucleic acid molecule of the present invention codes, at least in part, for a mitochondrial or plastid targeting peptide. A more preferred fragment nucleic acid molecule of the present invention codes for a plastid targeting peptide.

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112–123 (1998)), for example, can be used to identify potential PCR primers.

Another subset of the nucleic acid molecules of the invention include nucleic acid molecules that encode a protein or fragment thereof.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NO: 1 and complement thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0×sodium chloride/sodium citrate (SSC) at about 45° C., followed by a wash of 2.0×SSC at 20–25° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to a nucleic acid molecule having SEQ ID NO: 1 or a complement thereof under moderately stringent conditions, for example at about 2.0× SSC and about 65° C.

In a particularly preferred embodiment, a nucleic acid molecule of the present invention will include those nucleic acid molecules that specifically hybridize to a nucleic acid molecule having SEQ ID NO: 1 or the complement thereof under high stringency conditions such as 0.2×SSC and about 65° C.

In one aspect of the present invention, the nucleic acid molecules of the present invention have SEQ ID NO: 1 or the complement thereof. In another aspect of the present invention, a nucleic acid molecule of the present invention shares between 100% and 90% sequence identity to a nucleic acid molecule having SEQ ID NO: 1 or the complement thereof or fragment of either. In a further aspect of the present invention, a nucleic acid molecule of the present invention shares between 100% and 95% sequence identity to a nucleic acid molecule having SEQ ID NO: 1 or the complement thereof or fragment of either. In a more preferred aspect of the present invention, a nucleic acid molecule of the present invention shares between 100% and 98% sequence identity to a nucleic acid molecule having SEQ ID NO: 1 or the complement thereof or fragment of either. In an even more preferred aspect of the present invention, a nucleic acid molecule of the present invention shares between 100% and 99% sequence identity to a nucleic acid molecule having SEQ ID NO: 1 or the complement thereof or fragment of either.

In a preferred embodiment the percent identity calculations are performed using the Megalign program of the LASERGENE bioinformatics computing suite (default parameters, DNASTAR Inc., Madison, Wis.).

A nucleic acid molecule of the invention can also encode a homolog protein. As used herein, a homolog protein or fragment thereof is a counterpart protein molecule or fragment thereof in a second species (e.g., maize adenylate transporter is a homolog of *Arabidopsis* adenylate transporter). A homolog can also be generated by molecular evolution or DNA shuffling techniques, so that the molecule retains at least one functional or structural characteristic of the original protein (see, for example, U.S. Pat. No. 5,811,238).

In another embodiment, the homolog is selected from the group consisting of alfalfa, *Arabidopsis*, barley, *Brassica campestris, Brassica napus*, broccoli, cabbage, canola, citrus, cotton, garlic, oat, onion, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, Phaseolus, crambe, mustard, castor bean, sesame, cottonseed, linseed, safflower, and oil palm. More particularly, preferred homologs are selected from maize, *Brassica campestris, Brassica napus*, canola, soybean, crambe, mustard, castor bean, peanut, sesame, cottonseed, linseed, safflower, oil palm, flax, and sunflower. In an even more preferred embodiment, the homolog is selected from the group consisting of canola, maize, *Brassica campestris, Brassica napus*, soybean, sunflower, safflower, oil palm, and peanut.

In a preferred embodiment, the homolog is *Brassica napus*. In another preferred embodiment, the homolog is soybean. In another preferred embodiment, the homolog is canola.

In a preferred embodiment, nucleic acid molecules having SEQ ID NO: 1, the complement thereof, and fragments of either can be utilized to obtain such homologs.

In another further aspect of the present invention, nucleic acid molecules of the present invention can comprise sequences that differ from those encoding a protein or fragment thereof in SEQ ID NO: 2 because the different nucleic acid sequences encode a protein having one or more non-essential amino acid changes. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105–132 (1982)). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157:105–132 (1982)). These are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids which have hydropathic indices within ±2 is preferred, those which have hydropathic indices within ±1 are particularly preferred, and those which have hydropathic indices within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids which have hydrophilicity values within ±2 is preferred, those which have hydropathic indices within ±1 are particularly preferred, and those which have hydropathic indices within ±0.5 are even more particularly preferred.

In a further aspect of the present invention, one or more of the nucleic acid molecules of the present invention differ in nucleic acid sequence from those for which a specific sequence is provided herein because one or more codons has been replaced with a codon that encodes a conservative substitution of the amino acid originally encoded.

Agents of the invention include nucleic acid molecules that encode at least about a contiguous 10 amino acid region of a protein of the present invention, more preferably at least about a contiguous 25, 40, 50, 100, or 125 amino acid region of a protein of the present invention.

(b) Protein and Peptide Molecules

A class of agents includes one or more of the protein or fragments thereof or peptide molecules encoded by a nucleic acid agent of the invention. A preferred adenylate transporter is a plant adenylate transporter, more preferably an *Arabidopis thaliana* adenylate transporter. An example of a more preferred *Arabidopis thaliana* adenylate transporter is a protein with the amino acid sequence set forth in SEQ ID NO: 2. Preferred adenylate transporters of the present invention comprise a mitrochodrial or plastid targeting peptide. In a more preferred embodiment, an adenylate transporter of the present invention comprises a plastid targeting peptide.

As used herein, the term "protein" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein" or "peptide molecule" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof or peptide molecules may be produced via chemical synthesis, or more preferably, by expression in a suitable bacterial or eukaryotic host. Suitable methods for expression are described by Sambrook et al., In: *Molecular Cloning, A Laboratory Manual, 2nd Edition,* Cold Spring Harbor Press, Cold Spring Harbor, N.Y. (1989) or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion proteins or peptide molecules of the invention are preferably produced via recombinant means.

Another class of agents comprise a protein or peptide molecules or fragments or fusions thereof comprising SEQ ID NO: 2 and fragments thereof in which conservative, non-essential, or non-relevant amino acid residues have been added, replaced, or deleted. A further particularly preferred class of proteins are proteins in which conservative, non-essential, or non-relevant amino acid residues have been added, replaced, or deleted. Computerized means for designing modifications in protein structure are known in the art (Dahiyat and Mayo, *Science* 278:82–87 (1997)).

A protein of the invention can also be a homolog protein. As used herein, a homolog protein or fragment thereof is a counterpart protein or fragment thereof in a second species. A homolog can also be generated by molecular evolution or DNA shuffling techniques, so that the molecule retains at least one functional or structural characteristic of the original (see, for example, U.S. Pat. No. 5,811,238).

In another embodiment, the homolog is selected from the group consisting of alfalfa, *Arabidopsis,* barley, *Brassica campestris, Brassica napus,* broccoli, cabbage, canola, citrus, cotton, garlic, oat, onion, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, *Phaseolus,* crambe, mustard, castor bean, sesame, cottonseed, linseed, safflower, and oil palm. More particularly, preferred homologs are selected from maize, *Brassica campestris, Brassica napus,* canola, soybean, crambe, mustard, castor bean, peanut, sesame, cottonseed, linseed, safflower, oil palm, flax, and sunflower. In an even more preferred embodiment, the homolog is selected from the group consisting of canola, maize, *Brassica campestris, Brassica napus,* soybean, sunflower, safflower, oil palm, and peanut.

In a preferred embodiment, the homolog is *Brassica napus.* In another preferred embodiment, the homolog is soybean. In another preferred embodiment, the homolog is canola.

In a preferred embodiment, the nucleic acid molecules of the present invention or complements and fragments of either can be utilized to obtain such homologs.

Agents of the invention include proteins and fragments thereof comprising at least about a contiguous 10 amino acid region, preferably comprising at least about a contiguous 20 amino acid region, even more preferably comprising at least a contiguous 25, 35, 50, 75 or 100 amino acid region of a protein of the present invention. In another preferred embodiment, the proteins of the present invention include between about a 10 and about a 25 contiguous amino acid region, more preferably between about a 20 and about a 50 contiguous amino acid region, and even more preferably between about a 40 and about an 80 contiguous amino acid region.

(c) Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. In a preferred embodiment, the exogenous genetic material encodes a plant adenylate transporter, more preferably an *Arabidopsis thaliana* adenylate transporter. Preferred adenylate transporters of the present invention comprise a mitochondrial or plastid targeting peptide. In a more preferred embodiment, an adenylate transporter of the present invention comprises a plastid targeting sequence.

In another preferred embodiment, the exogenous genetic material includes a nucleic acid molecule of the present invention, preferably a nucleic acid molecule comprising SEQ ID NO: 1 or complement thereof or fragment of either. A further preferred class of exogenous genetic material is nucleic acid molecules that encode a protein or fragment thereof having an amino acid of SEQ ID NO: 2 or fragment thereof.

In one embodiment of the present invention, exogenous genetic material comprising an adenylate transporter homolog or fragment thereof is introduced into a plant with one or more additional genes. In one embodiment, preferred combinations of genes include two or more of the following genes: tyrA, slr1736, ATPT2, dxs, dxr, GGPPS, HPPD, GMT, AANT1, slr 1737, and an antisense construct for homogentisic acid dioxygenase (Kridl et al., *Seed Sci. Res.*

1:209:219 (1991); Keegstra, *Cell* 56(2):247–53 (1989); Nawrath, et al., *Proc. Natl. Acad. Sci. U.S.A.* 91:12760–12764 (1994); Xia et al., *J. Gen. Microbiol.* 138:1309–1316 (1992); Cyanobase www.kazusa.or.jp/cyanobase; Lois et al., *Proc. Natl. Acad. Sci. U.S.A.* 95 (5):2105–2110 (1998); Takahashi et al. *Proc. Natl. Acad. Sci. U.S.A.* 95 (17), 9879–9884 (1998); Norris et al., *Plant Physiol.* 117:1317–1323 (1998); Bartley and Scolnik, *Plant Physiol.* 104:1469–1470 (1994), Smith et al., *Plant J.* 11: 83–92 (1997); WO 00/32757; WO 00/10380; Saint Guily, et al., *Plant Physiol.*, 100(2):1069–1071 (1992); Sato et al., *J. DNA Res.* 7 (1):31–63 (2000)). In such combinations, one or more of the gene products can be directed to the plastid by the use of a plastid targeting sequence. Alternatively, one or more of the gene products can be localized in the cytoplasm. Such genes can be introduced, for example, with the adenylate transporter homolog or fragment thereof and one or more additional genes on a single construct, or with the adenylate transporter homolog or fragment thereof and one or more additional genes introduced on different constructs but the with same transformation event, or introduced into separate plants followed by one or more crosses to generate the desired combination of genes. In such combinations, a preferred promoter is a napin promoter and a preferred plastid targeting sequence is a CTP1 sequence.

In another embodiment, DNA constructs can be generated as "multiple gene constructs". In one embodiment, the multiple gene constructs contain multiple genes each under the control of a separate promoter, for example a seed specific promoter such as the napin promoter, arcelin 5, or 7S promoter. The products of each of the genes can be individually targeted to the plastid by an encoded plastid target peptide. The multiple gene construct or constructs can have one or more of the following genes in addition to AANT1: tyrA, slr1736, ATPT2, dxs, dxr, GGPPS, HPPD, GMT, AANT1, slr 1737, MT1, TMT2, and an antisense construct for homogentisic acid dioxygenase.

Such genetic material may be transferred into either monocotyledons or dicotyledons including, but not limited to, maize, soybean, canola, *Arabidopsis*, phaseolus, peanut, alfalfa, wheat, rice, oat, sorghum, rye, tritordeum, millet, fescue, perennial ryegrass, sugarcane, cranberry, papaya, banana, safflower, oil palm, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee, and dioscorea (Christou, In: *Particle Bombardment for Genetic Engineering of Plants*, Biotechnology Intelligence Unit. Academic Press, San Diego, Calif. (1996)), with canola, maize, *Brassica campestris, Brassica napus*, soybean, crambe, mustard, castor bean, peanut, sesame, cottonseed, linseed, safflower, oil palm, flax, and sunflower preferred, and canola, maize, *Brassica campestris, Brassica napus*, soybean, sunflower, safflower, oil palm, and peanut more preferred. In a more preferred embodiment, the genetic material is transferred into soybean. In another more preferred embodiment, the genetic material is transferred into canola. In another more preferred embodiment, the genetic material is transferred into *Brassica napus*.

Transfer of a nucleic acid that encodes a protein can result in expression or overexpression of that protein in a transformed cell or transgenic plant. One or more of the proteins or fragments thereof encoded by nucleic acid molecules of the invention may be overexpressed in a transformed cell or transformed plant. Such expression or overexpression may be the result of transient or stable transfer of the exogenous genetic material.

In a preferred embodiment, expression or overexpression of a protein or fragment thereof of the present invention in a plant provides in that plant, relative to an untransformed plant with a similar genetic background, an increased level of tocopherols.

In a preferred embodiment, overexpression of a protein or fragment thereof of the present invention in a plant provides in that plant, relative to an untransformed plant with a similar genetic background, an increased level of α-tocopherols.

In a preferred embodiment, overexpression of a protein or fragment thereof of the present invention in a plant provides in that plant, relative to an untransformed plant with a similar genetic background, an increased level of γ-tocopherols.

In another embodiment, overexpression of a protein or fragment thereof of the present invention in a plant provides in that plant, relative to an untransformed plant with a similar genetic background, an increased level of homogentisic acid.

In another embodiment, overexpression of a protein or fragment thereof of the present invention in a plant provides in that plant, relative to an untransformed plant with a similar genetic background, an increased level of phytylpyrophosphate acid.

In another preferred embodiment, overexpression of a protein or fragment thereof of the present invention in a transformed plant may provide tolerance to a variety of stressors, e.g. oxidative stress tolerance such as to oxygen or ozone, UV tolerance, cold tolerance, or fungal/microbial pathogen tolerance.

As used herein in a preferred aspect, a tolerance or resistance to stress is determined by the ability of a plant, when challenged by a stressor such as cold, to produce a plant having a higher yield than a plant without such tolerance or resistance to stress. In a particularly preferred aspect of the present invention, the tolerance or resistance to stress is measured relative to a plant with a similar genetic background to the tolerant or resistant plant except that the plant expresses or overexpresses a protein or fragment thereof of the present invention.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, N.Y. (1997)). In some embodiments of this invention, DNA vector constructs may be multiple gene constructs that comprise an expression casset for the adenylate transporter or a fragment thereof and one or more gene sequences selected from the group consisting of tyrA, slr1736, ATPT2, dxs, dxr, GGH, GGPPS, HPPD, MT1, TMT2, GMT, AANT1, slr 1737, and an antisense construct for homogentisic acid dioxygenase, such that transformation with a single DNA vector construct will result in the expression of the two or more of the gene sequences.

A construct or vector may include a plant promoter to express the protein or protein fragment of choice. A number of promoters that are active in plant cells have been described in the literature. These include the nopaline synthase (NOS) promoter (Ebert et al., *Proc. Natl. Acad. Sci. (U.S.A.)* 84:5745–5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315–324 (1987)), the CaMV 35S promoter (Odell et al., *Nature*

313:810–812 (1985)), the figwort mosaic virus 35S-promoter, which is the light-inducible promoter from the small subunit of ribulose-1,5-bis-phosphate carboxylase (ss-RUBISCO), the Adh promoter (Walker et al., *Proc. Natl. Acad. Sci. (U.S.A.)* 84:6624–6628 (1987)), the sucrose synthase promoter (Yang et al., *Proc. Natl. Acad. Sci. (U.S.A.)* 87:4144–4148 (1990)), the R gene complex promoter (Chandler et al., *The Plant Cell* 1:1175–1183 (1989)), the chlorophyll a/b binding protein gene promoter, etc. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci. (U.S.A.)* 87:3459–3463 (1990)), the chloroplast fructose-1,6-biphosphatase (FBPase) promoter from wheat (Lloyd et al., *Mol. Gen. Genet.* 225:209–216 (1991)), the nuclear photosynthetic ST-LS1 promoter from potato (Stockhaus et al., *EMBO J.* 8:2445–2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773–778 (1994)), the promoter for the Cab-1 gene from wheat (Fejes et al., *Plant Mol. Biol.* 15:921–932 (1990)), the promoter for the CAB-1 gene from spinach (Lubberstedt et al., *Plant Physiol.* 104:997–1006 (1994)), the promoter for the cab1R gene from rice (Luan et al., *Plant Cell.* 4:971–981 (1992)), the pyruvate, orthophosphate dikinase (PPDK) promoter from maize (Matsuoka et al., *Proc. Natl. Acad. Sci. (U.S.A.)* 90: 9586–9590 (1993)), the promoter for the tobacco Lhcb1*2 gene (Cerdan et al., *Plant Mol. Biol.* 33:245–255 (1997)), the *Arabidopsis thaliana* SUC2 sucrose-H+ symporter promoter (Truernit et al., *Planta.* 196:564–570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (*Sinapis alba*; Kretsch et al., *Plant Mol. Biol.* 28:219–229 (1995)).

For the purpose of expression in sink tissues of the plant, such as the tuber of the potato plant, the fruit of tomato, or the seed of maize, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., *EMBO J.* 8:1899–1906 (1986); Jefferson et al., *Plant Mol. Biol.* 14:995–1006 (1990)), the promoter for the potato tuber ADPGPP genes, both the large and small subunits, the sucrose synthase promoter (Salanoubat and Belliard, *Gene* 60:47–56 (1987), Salanoubat and Belliard, *Gene* 84:181–185 (1989)), the promoter for the major tuber proteins including the 22 kd protein complexes and protease inhibitors (Hannapel, *Plant Physiol.* 101:703–704 (1993)), the promoter for the granule-bound starch synthase gene (GBSS) (Visser et al., *Plant Mol. Biol.* 17:691–699 (1991)), and other class I and II patatin promoters (Koster-Topfer et al., *Mol Gen Genet.* 219:390–396 (1989); Mignery et al., *Gene.* 62:27–44 (1988)).

Other promoters can also be used to express a protein or fragment thereof in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219 (1991)), phaseolin (Bustos, et al., *Plant Cell,* 1(9):839–853 (1989)), soybean trypsin inhibitor (Riggs, et al., *Plant Cell* 1(6):609–621 (1989)), ACP (Baerson, et al., *Plant Mol. Biol.,* 22(2):255–267 (1993)), stearoyl-ACP desaturase (Slocombe, et al., *Plant Physiol.* 104(4):167–176 (1994)), soybean a' subunit of β-conglycinin (soy 7S, (Chen et al., *Proc. Natl. Acad. Sci.,* 83:8560–8564 (1986))), and oleosin (see, for example, Hong, et al., *Plant Mol. Biol.,* 34(3):549–555 (1997)). Further examples include the promoter for β-conglycinin (Chen et al., *Dev. Genet.* 10: 112–122 (1989)). A further preferred promoter is the arcelin 5 (Arc5) promoter (Goossens et al., *Plant Physiol.* 120:1095–1104 (1999), and as disclosed in U.S. application Ser. No. 60/255,879, filed on Dec. 18, 2000 and U.S. application Ser. No. 10/015,637, filed on Dec. 17, 2001 both of which are herein incorporated by reference in their entirety)). Also included are the zeins, which are a group of storage proteins found in maize endospenn. Genomic clones for zein genes have been isolated (Pedersen et al., *Cell* 29:1015–1026 (1982), and Russell et al., *Transgenic Res.* 6(2): 157–168) and the promoters from these clones, including the 15 kD, 16 kD, 19 kD, 22 kD, 27 kD and genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell Biol.* 13:5829–5842 (1993)). Examples of promoters suitable for expression in wheat include those promoters for the ADP-glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins, and the aleurone specific proteins. A preferred promoter for expression in the seed is a napin promoter.

Root specific promoters may also be used. An example of such a promoter is the promoter for the acid chitinase gene (Samac et al., *Plant Mol. Biol.* 25:587–596 (1994)). Expression in root tissue could also be accomplished by utilizing the root specific subdomains of the CaMV35S promoter that have been identified (Lam et., *Proc. Natl. Acad. Sci. (U.S.A.)* 86:7890–7894 (1989)). Other root cell specific promoters include those reported by Conkling et al. (Conkling et al., *Plant Physiol.* 93:1203–1211 (1990)).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977–984 (1989)).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671–680 (1989); Bevan et al., *Nucleic Acids Res.* 11:369–385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region which is naturally associated with the transcript initiation region. The skilled artisan will recognize that any convenient transcript termination region which is capable of terminating transcription in a plant cell can be employed in the constructs of the present invention.

A vector or construct may also include regulatory elements. Examples of such include the Adh intron 1 (Callis et al., *Genes and Develop.* 1:1183–1200 (1987)), the sucrose synthase intron (Vasil et al., *Plant Physiol.* 91:1575–1579 (1989)), and the TMV omega element (Gallie et al., *The Plant Cell* 1:301–311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183–188 (1985)) which codes for kanamycin resistance and can be selected for using kanamycin, RptII, G418, hpt, etc.; a bar gene which codes for bialaphos resistance; a mutant EPSP synthase gene (Hinchee et al., *Bio/Technology* 6:915–922 (1988); Reynaerts et al., Selectable and Screenable Markers. In Gelvin and Schilperoort. Plant Molecular Biology Manual, Kluwer, Dordrecht (1988); Reynaerts et al., Selectable and screenable markers. In Gelvin and Schilperoort. Plant Molecular Biology Manual, Kluwer, Dordrecht (1988)), aadA (Jones et al., Mol. Gen. Genet. (1987)) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance (European Patent Application 154,204 (Sep. 11, 1985)); ALS (D'Halluin et al., Bio/Technology 10: 309–314 (1992)); and a methotrexate resistant DHFR gene (Thillet et al., *J. Biol. Chem.* 263:12500–12508 (1988)).

A vector or construct may also include a transit peptide. Incorporation of a suitable chloroplast transit peptide may also be employed (European Patent Application Publication Number 0218571). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393–405 (1996). A preferred plastid transit peptide sequence is CTP1.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.* 5.387–405 (1987); Jefferson et al., *EMBO J.* 6:3901–3907 (1987)); an R-locus gene, which encodes a product that regulates the production of anthocyanin pigments (red color) in plant tissues (Dellaporta et al., Stadler Symposium 11:263–282 (1988)); a β-lactamase gene (Sutcliffe et al., *Proc. Natl. Acad. Sci. (U.S.A.)* 75:3737–3741 (1978)), a gene which encodes an enzyme for which various chromogenic substrates are known (e.g., PADAC, a chromogenic cephalosporin); a luciferase gene (Ow et al., *Science* 234:856–859 (1986)); a xylE gene (Zukowsky et al., *Proc. Natl. Acad. Sci. (U.S.A.)* 80:1101–1105 (1983)) which encodes a catechol dioxygenase that can convert chromogenic catechols; an α-amylase gene (Ikatu et al., *Bio/Technol.* 8:241–242 (1990)); a tyrosinase gene (Katz et al., *J. Gen. Microbiol.* 129:2703–2714 (1983)) which encodes an enzyme capable of oxidizing tyrosine to DOPA and dopaquinone which in turn condenses to melanin; and an α-galactosidase which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation, by acceleration of DNA coated particles, etc. (Potrykus, *Ann. Rev. Plant Physiol. Plant Mol. Biol.* 42:205–225 (1991); Vasil, *Plant Mol. Biol.* 25:925–937 (1994)). For example, electroporation has been used to transform maize protoplasts (Fromm et al., *Nature* 312: 791–793 (1986)).

Other vector systems suitable for introducing transforming DNA into a host plant cell include but are not limited to binary artificial chromosome (BIBAC) vectors (Hamilton et al., *Gene* 200:107–116 (1997)); and transfection with RNA viral vectors (Della-Cioppa et al., *Ann. N.Y. Acad. Sci.* (1996), 792 (Engineering Plants for Commercial Products and Applications), 57–61). Additional vector systems also include plant selectable YAC vectors such as those described in Mullen et al., *Molecular Breeding* 4:449–457 (1988).

Technology for introduction of DNA into cells is well known to those of skill in the art. Four general methods for delivering a gene into cells have been described: (1) chemical methods (Graham and van der Eb, *Virology* 54:536–539

(1973)); (2) physical methods such as microinjection (Capecchi, *Cell* 22:479–488 (1980)), electroporation (Wong and Neumann, *Biochem. Biophys. Res. Commun.* 107:584–587 (1982); Fromm et al., *Proc. Natl. Acad. Sci. (U.S.A.)* 82:5824–5828 (1985); U.S. Pat. No. 5,384,253), the gene gun (Johnston and Tang, *Methods Cell Biol.* 43:353–365 (1994)), and vacuum infiltration (Bechtold et al., *C.R. Acad. Sci. Paris, Life Sci.* 316:1194–1199 (1993)); (3) viral vectors (Clapp, *Clin. Perinatol.* 20:155–168 (1993); Lu et al., *J. Exp. Med.* 178:2089–2096 (1993), Eglitis and Anderson, *Biotechniques* 6:608–614 (1988)); and (4) receptor-mediated mechanisms (Curiel et al., *Hum. Gen. Ther.* 3:147–154 (1992), Wagner et al., *Proc. Natl. Acad. Sci. (USA)* 89:6099–6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer,* Oxford Press, Oxford, England (1994). Non-biological particles (microprojectiles) may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671–674 (1988)) nor the susceptibility to *Agrobacterium* infection is required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with maize cells cultured in suspension. Gordon-Kamm et al., describes the basic procedure for coating tungsten particles with DNA (Gordon-Kamm et al., *Plant Cell* 2:603–618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, California)(Sanford et al., *Technique* 3:3–16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus which expresses the exogenous gene product 48 hours post-bombardment often ranges from one to ten, and averages from one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)* 87:8526–8530 (1990); Svab and Maliga, *Proc. Natl. Acad. Sci. (U.S.A.)* 90:913–917 (1993); Staub and Maliga, *EMBO J.* 12:601–606 (1993); U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and which may therefore influence transformation and integration efficiencies. For example, the osmotic state, tissue hydration, and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example the methods described by Fraley et al., *Bio/Technology* 3:629–635 (1985) and Rogers et al., *Methods Enzymol.* 153:253–277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986)).

Modem *Agrobacterium* transformation vectors are capable of replication in *E. coli* as well as *Agrobacterium*, allowing for convenient manipulations as described (Klee et al., In: *Plant DNA Infectious Agents,* Hohn and Schell (eds.), Springer-Verlag, N.Y., pp. 179–203 (1985)). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et (al., *Methods Enzymol.* 153:253–277 (1987)). In addition, *Agrobacterium* containing both armed and disarmed Ti genes can be used for the transformations. In those plant strains where *Agro-* bacterium-mediated transformation is efficient, it is the method of choice because of the facile and defined nature of the gene transfer.

A transgenic plant formed using Agrobacterium transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced, and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193–200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454–457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor Appl. Genet.* 205:34 (1986); Yamada et al., *Plant Cell Rep.* 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988)). In addition, "particle gun" or high-velocity microprojectile technology can be utilized (Vasil et al., *Bio/Technology* 10:667 (1992)).

Using the latter technology, DNA is carried through the cell wall and into the cytoplasm on the surface of small metal particles as described (Klein et al., *Nature* 328:70 (1987); Klein et al., *Proc. Natl. Acad. Sci. (U.S.A.)* 85:8502–8505 (1988); McCabe et al., *Bio/Technology* 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.* 107:367 (1987); Luo et al., *Plant Mol Biol. Reporter* 6:165 (1988)), by direct injection of DNA into reproductive organs of a plant (Pena et al., *Nature* 325:274 (1987)), or by direct injection of DNA into the cells of immature embryos followed by the rehydration of desiccated embryos (Neuhaus et al., *Theor Appl. Genet.* 75:30 (1987)).

The regeneration, development, and cultivation of plants from single plant protoplast transformants or from various transformed explants is well known in the art (Weissbach and Weissbach, In: *Methods for Plant Molecular Biology,* Academic Press, San Diego, Calif., (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed with seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; 5,518,908); soybean (U.S. Pat. Nos. 5,569,834; 5,416,011; McCabe et. al., *Biotechnology* 6:923 (1988); Christou et al., *Plant Physiol.* 87:671–674 (1988)); Brassica (U.S. Pat. No. 5,463,174); peanut (Cheng et al., *Plant Cell Rep.* 15:653–657 (1996), McKently et al., *Plant Cell Rep.* 14:699–703 (1995)); papaya; pea (Grant et al., *Plant Cell Rep.* 15:254–258 (1995)); and *Arabidopsis thaliana* (Bechtold et al., *C.R. Acad. Sci. Paris, Life Sci.* 316:1194–1199 (1993)). The latter method for transforming *Arabidopsis thaliana* is commonly called "dipping" or vacuum infiltration or germplasm transformation.

Transformation of monocotyledons using electroporation, particle bombardment, and *Agrobacterium* have also been reported. Transformation and plant regeneration have been achieved in asparagus (Bytebier et al., *Proc. Natl. Acad. Sci. (USA)* 84:5354 (1987)); barley (Wan and Lemaux, *Plant Physiol* 104:37 (1994)); maize (Rhodes et al., *Science* 240: 204 (1988); Gordon-Kamm et al., *Plant Cell* 2:603–618 (1990); Fromm et al., *Bio/Technology* 8:833 (1990); Koziel et al., *Bio/Technology* 11:194 (1993); Armstrong et al., *Crop Science* 35:550–557 (1995)); oat (Somers et al., *Bio/Technology* 10:1589 (1992)); orchard grass (Horn et al., *Plant Cell Rep.* 7:469 (1988)); rice (Toriyama et al., *Theor Appl. Genet.* 205:34 (1986); Part et al., *Plant Mol. Biol.* 32:1135–1148 (1996); Abedinia et al., *Aust. J. Plant Physiol.* 24:133–141 (1997); Zhang and Wu, *Theor. Appl. Genet.* 76:835 (1988); Zhang et al., *Plant Cell Rep.* 7:379 (1988); Battraw and Hall, *Plant Sci.* 86:191–202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al, *Bio/Technology* 10:691 (1992)); and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.*

6:609–618 (1992); Goffet al., *EMBO J.* 9:2517–2522 (1990)). Transient expression systems maybe used to functionally dissect gene constructs (see generally, Mailga et al., *Methods in Plant Molecular Biology,* Cold Spring Harbor Press (1995)).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279–289 (1990); van der Krol et al., *Plant Cell* 2:291–299 (1990)). Cosuppression may result from stable transformation with a single copy nucleic acid molecule that is homologous to a nucleic acid sequence found within the cell (Prolls and Meyer, *Plant J.* 2:465–475 (1992)) or with multiple copies of a nucleic acid molecule that is homologous to a nucleic acid sequence found within the cell (Mittlesten et al., *Mol. Gen. Genet.* 244.325–330 (1994)). Genes, even though different, linked to homologous promoters may result in the cosuppression of the linked genes (Vaucheret, *C.R. Acad. Sci. III* 316:1471–1483 (1993); Flavell, *Proc. Natl. Acad. Sci. (U.S.A.)* 91:3490–3496 (1994); van Blokland et al., *Plant J.* 6:861–877 (1994); Jorgensen, *Trends Biotechnol.* 8:340–344 (1990); Meins and Kunz, In: *Gene Inactivation and Homologous Recombination in Plants,* Paszkowski (ed.), pp. 335–348, Kluwer Academic, Netherlands (1994)).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427–430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering,* Setlow (ed.), Vol. 11, New York: Plenum 49–63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.* 55:569–597 (1986)). In one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155–184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule whose non-transcribed strand encodes a protein or fragment thereof.

Posttranscriptional gene silencing (PTGS) can result in virus immunity or gene silencing in plants. PTGS is induced by dsRNA and is mediated by an RNA-dependent RNA polymerase, present in the cytoplasm, that requires a dsRNA template. The dsRNA is formed by hybridization of complementary transgene mRNAs or complementary regions of the same transcript. Duplex formation can be accomplished by using transcripts from one sense gene and one antisense gene collocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNase molecules hybridize to the endogene mRNA and cleave the single-stranded RNA adjacent to the hybrid. The cleaved single-stranded RNAs are further degraded by other host RNAses because one will lack a capped 5' end and the other will lack a poly(A) tail (Waterhouse et al., *PNAS* 95: 13959–13964 (1998)).

It is understood that one or more of the nucleic acids of the invention may be introduced into a plant cell and transcribed using an appropriate promoter with such transcription resulting in the postranscriptional gene silencing of an endogenous transcript.

Antibodies have been expressed in plants (Hiatt et al., *Nature* 342:76–78 (1989); Conrad and Fielder, *Plant Mol. Biol.* 26:1023–1030 (1994)). Cytoplasmic expression of an scFv (single-chain Fv antibody) has been reported to delay infection by artichoke mottled crinkle virus. Transgenic plants that express antibodies directed against endogenous proteins may exhibit a physiological effect (Philips et al., *EMBO J.* 16:4489–4496 (1997); Marion-Poll, *Trends in Plant Science* 2:447–448 (1997)). For example, expressed anti-abscisic antibodies have been reported to result in a general perturbation of seed development (Philips et al., *EMBO J.* 16: 4489–4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313–1315 (1997); Baca et al., *Ann. Rev. Biophys. Biomol. Struct.* 26:461–493 (1997)). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585.

It is understood that any of the antibodies of the invention may be expressed in plants and that such expression can result in a physiological effect. It is also understood that any of the expressed antibodies may be catalytic.

The present invention also provides for parts of the plants, particularly reproductive or storage parts. Plant parts, without limitation, include seed, endosperm, ovule, and pollen. In a particularly preferred embodiment of the present invention, the plant part is a seed. In one embodiment the seed is a constituent of animal feed.

In another embodiment, the plant part is a fruit, more preferably a fruit with enhanced shelf life. In another preferred embodiment, the fruit has increased levels of tocopherol.

The present invention also provides a container of at least about 10,000, more preferably at least about 20,000, and even more preferably at least about 40,000 seeds where at least about 10%, more preferably at least about 25%, more preferably at least about 50% more preferably at least about 75% and even more preferably at least about 90% of the seeds are seeds derived from a plant of the present invention.

The present invention also provides a container of at least about 10 kg, more preferably at least about 25 kg, and even more preferably at least about 50 kg seeds where at least about 10%, more preferably at least about 25%, more preferably at least about 50%, more preferably at least about 75%, and even more preferably at least about 90% of the seeds are seeds derived from a plant of the present invention.

Any of the plants or parts thereof of the present invention may be processed to produce a feed, meal, protein, or oil preparation. A particularly preferred plant part for this purpose is a seed. In a preferred embodiment the feed, meal, protein, or oil preparation is designed for ruminant animals. Methods to produce feed, meal, protein, and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of at least about than 5% w/v, more preferably at least about 10% w/v, and even more preferably at least about 15% w/v. In a preferred oil preparation, the oil preparation is a high oil preparation with an oil content derived from a plant or part thereof of the present invention of at least about 5% w/v, more preferably at least about 10% w/v, and even more preferably at least about 15% w/v. In a preferred embodiment the oil preparation is a liquid and of a volume greater than 1, 5, 10 or 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75%, or 90% by volume or weight of the oil component of any product. In another embodiment, the oil preparation may be blended and can constitute greater than 10%, 25%, 35%, 50%, or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, threshability, etc. will generally dictate the choice.

For highly heritable traits, a choice of superior individual plants evaluated at a single location will be effective, whereas selection for traits with low heritability should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences the choice of breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties, and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$ population. An $F_2$ population is produced by selfing one or several members of the $F_1$ population. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from these lines are derived will each trace to different $F_2$ individuals. The number of plants in a population declines each generation due to failure of some seeds to germinate or of some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population during each generation of inbreeding.

Descriptions of other breeding methods that are commonly used for different traits and crops can be found in one of several reference books (e.g. Fehr, *Principles of Cultivar Development* Vol. 1, pp. 2–3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucellus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes endosperm production possible. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

(d) Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Methods to transform such cells or organisms are known in the art (EP 0 238 023; Yelton et al., *Proc. Natl. Acad. Sci. (U.S.A.)*, 81:1470–1474 (1984); Malardier et al., *Gene,* 78:147–156 (1989); Becker and Guarente, In: Abelson and Simon (eds.), *Guide to Yeast Genetics and Molecular Biology, Method Enzymol.,* Vol. 194, pp. 182–187, Academic Press, Inc., New York; Ito et al., *J. Bacteriology,* 153:163 (1983) Hinnen et al., *Proc. Natl. Acad. Sci. (U.S.A.),* 75:1920 (1978); Bennett and LaSure (eds.), *More Gene Manipulation In Fungi,* Academic Press, California (1991)). (1)). Methods to produce proteins of the present invention are also known (Kudla et al., *EMBO,* 9:1355–1364 (1990); Jarai and Buxton, *Current Genetics,* 26:2238–2244 (1994); Verdier, *Yeast,* 6:271–297 (1990); MacKenzie et al., *Journal of Gen. Microbiol.,* 139: 2295–2307 (1993); Hartl et al., *TIBS,* 19:20–25 (1994); Bergenron et al., *TIBS,* 19:124–128 (1994); Demolder et al., *J. Biotechnology,* 32:179–189 (1994); Craig, *Science,* 260: 1902–1903 (1993); Gething and Sambrook, *Nature,* 355: 33–45 (1992); Puig and Gilbert, *J. Biol. Chem.,* 269:7764–7771 (1994); Wang and Tsou, *FASEB Journal,* 7:1515–1517 (1993); Robinson et al., *Bio/Technology,* 1:381–384 (1994); Enderlin and Ogrydziak, *Yeast,* 10:67–79 (1994); Fuller et al., *Proc. Natl. Acad. Sci. (U.S.A),* 86:1434–1438 (1989); Julius et al., *Cell,* 37:1075–1089 (1984); Julius et al., *Cell* 32:839–852 (1983)).

In a preferred embodiment, overexpression of a protein or fragment thereof of the present invention in a cell or organism provides in that cell or organism, relative to an untransformed cell or organism with a similar genetic background, an increased level of tocopherols.

In a preferred embodiment, overexpression of a protein or fragment thereof of the present invention in a cell or organism provides in that cell or organism, relative to an untransformed cell or organism with a similar genetic background, an increased level of α-tocopherols.

In a preferred embodiment, overexpression of a protein or fragment thereof of the present invention in a cell or organism provides in that cell or organism, relative to an untransformed cell or organism with a similar genetic background, an increased level of γ-tocopherols.

In another embodiment, overexpression of a protein or fragment thereof of the present invention in a cell or organism provides in that plant, relative to an untransformed plant with a similar genetic background, an increased level of homogentisic acid.

In another embodiment, overexpression of a protein or fragment thereof of the present invention in a cell or organism provides in that plant, relative to an untransformed plant with a similar genetic background, an increased level of phytylpyrophosphate acid.

(e) Antibodies

One aspect of the invention concerns antibodies, single-chain antigen binding molecules, or other proteins that specifically bind to one or more of the protein or peptide molecules of the invention and their homologs, fusions, or fragments. In a particularly preferred embodiment, the antibody specifically binds to a protein having the amino acid sequence set forth in SEQ ID NO: 2. Such antibodies may be used to quantitatively or qualitatively detect the protein or peptide molecules of the invention. As used herein, an antibody or peptide is said to "specifically bind" to a protein or peptide molecule of the invention if such binding is not competitively inhibited by the presence of non-related molecules.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments, may be a "fusion" molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulin fragments (such as (F(ab'), F(ab')$_2$), or single-chain immunoglobulins producible, for example, via recombinant means. It is understood that practitioners are familiar with the standard resource materials which describe specific conditions and procedures for the construction, manipulation, and isolation of antibodies (see, for example, Harlow and Lane, In: *Antibodies: A Laboratory Manual,* Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope, or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the invention may be employed to obtain other nucleic acid molecules from the same species (nucleic acid molecules from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologs. Such homologs include the nucleic acid molecules of other plants or other organisms (e.g., alfalfa, *Arabidopsis*, barley, *Brassica*, broccoli, cabbage, canola, citrus, cotton, garlic, oat, oilseed rape, onion, *Brassica campestris, Brassica napus,* flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, maize, soybean, *Phaseolus*, etc.) including the nucleic acid molecules that encode, in whole or in part, protein homologues of other plant species or other organisms and sequences of genetic elements, such as promoters and transcriptional regulatory elements. Particularly preferred plants are selected from the group consisting of canola, maize, *Brassica campestris, Brassica napus,* soybean, crambe, mustard, castor bean, peanut, sesame, cottonseed, linseed, safflower, oil palm, flax and sunflower. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in SEQ ID NO: 1 or complements thereof because complete complementarity is not needed for stable hybridization. The nucleic acid molecules of the invention therefore also include molecules that, although capable of specifically hybridizing with the nucleic acid molecules, may lack "complete complementarity."

Any of a variety of methods may be used to obtain one or more of the above-described nucleic acid molecules (Zamechik et al., *Proc. Natl. Acad. Sci. (U.S.A.)* 83:4143–4146 (1986); Goodchild et al., *Proc. Natl. Acad. Sci. (U.S.A.)* 85:5507–5511 (1988); Wickstrom et al., *Proc. Natl. Acad. Sci. (U.S.A.)* 85:1028–1032 (1988); Holt et al., *Molec. Cell. Biol.* 8:963–973 (1988); Gerwirtz et al., *Science* 242:1303–1306 (1988); Anfossi et al., *Proc. Natl. Acad. Sci. (U.S.A.)* 86:3379–3383 (1989); Becker et al., *EMBO J.* 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263–273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci. (U.S.A.)* 85:8998–9002 (1988); Ohara et al., *Proc. Natl. Acad. Sci. (U.S.A.)* 86:5673–5677 (1989); Pang et al., *Biotechniques* 22:1046–1048 (1977); Huang et al., *Methods Mol. Biol.* 69:89–96 (1997); Huang et al., *Method Mol. Biol.* 67:287–294 (1997); Benkel et al., *Genet. Anal.* 13:123–127 (1996); Hartl et al., *Methods Mol. Biol.* 58:293–301 (1996)). The term "chromosome walking" means a process of extending a genetic map by successive hybridization steps.

The nucleic acid molecules of the invention may be used to isolate promoters of cell enhanced, cell specific, tissue enhanced, tissue specific, developmentally regulated, or environmentally regulated expression profiles. Isolation and functional analysis of the 5' flanking promoter sequences of these genes from genomic libraries, for example, using genomic screening methods and PCR techniques, would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include, but are not limited to, enhancer sequences. Such genetic elements could be used to enhance gene expression of new and existing traits for crop improvement.

Another subset of the nucleic acid molecules of the invention includes nucleic acid molecules that are markers. The markers can be used in a number of conventional ways in the field of molecular genetics. Such markers include nucleic acid molecules of SEQ ID NO: 1, and complements thereof and fragments of either that can act as markers and other nucleic acid molecules of the present invention that can act as markers.

Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella, *Ann. Rev. Biochem.* 55:831–854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a population may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113–115 (1992); Jones et al., *Eur. J. Haematol.* 39:144–147 (1987); Horn et al., PCT Patent Application WO91/14003; Jeffreys, European Patent Application 370, 719; Jeffreys, U.S. Pat. No. 5,175,082; Jeffreys et al., *Amer. J. Hum. Genet.* 39:11–24 (1986); Jeffreys et al., *Nature* 316:76–79 (1985); Gray et al., *Proc. R. Acad. Soc. Lond.* 243:241–253 (1991); Moore et al., *Genomics* 10:654–660 (1991); Jeffreys et al., *Anim. Genet.* 18:1–15 (1987); Hillel et al., *Anim. Genet* 20:145–155 (1989); Hillel et al., *Genet.* 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of the polymorphism in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" ("RFLPs") (Glassberg, UK Patent Application 2135774; Skolnick et al., *Cytogen. Cell Genet.* 32:58–67 (1982); Botstein et al., *Ann. J. Hum. Genet.* 32:314–331 (1980); Fischer et al., (PCT Application WO90/13668; Uhlen, PCT Application WO90/11369).

Polymorphisms can also be identified by Single Strand Conformation Polymorphism (SSCP) analysis (Elles, *Methods in Molecular Medicine: Molecular Diagnosis of Genetic Diseases*, Humana Press (1996); Orita et al., *Genomics* 5:874–879 (1989)). A number of protocols have been described for SSCP including, but not limited to, Lee et al., *Anal. Biochem.* 205:289–293 (1992); Suzuki et al., *Anal. Biochem.* 192:82–84 (1991); Lo et al., *Nucleic Acids Research* 20:1005–1009 (1992); Sarkar et al., *Genomics* 13:441–443 (1992). It is understood that one or more of the nucleic acids of the invention may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407–4414 (1995)). This method allows for the specific co-amplification of high numbers of restriction fragments, which can be visualized by PCR without knowledge of the nucleic acid sequence. It is understood that one or more of the nucleic acids of the invention may be utilized as a marker or probe to detect polymorphisms by AFLP analysis or for fingerprinting RNA.

Polymorphisms may also be found using random amplified polymorphic DNA (RAPD) (Williams et al., *Nucl. Acids Res.* 18:6531–6535 (1990)) and cleaveable amplified polymorphic sequences (CAPS) (Lyamichev et al., *Science* 260: 778–783 (1993)). It is understood that one or more of the nucleic acid molecules of the invention may be utilized as markers or probes to detect polymorphisms by RAPD or CAPS analysis.

Single Nucleotide Polymorphisms (SNPs) generally occur at a greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314–331 (1980); Konieczny and Ausubel, *Plant J.* 4:403–410 (1993)), enzymatic and chemical mismatch assays (Myers et al., *Nature* 313:495–498 (1985)), allele-specific PCR (Newton et al., *Nucl. Acids Res.* 17:2503–2516 (1989); Wu et al., *Proc. Natl. Acad. Sci. USA* 86:2757–2760 (1989)), ligase chain reaction (Barany, *Proc. Natl. Acad. Sci. USA* 88:189–193 (1991)), single-strand conformation polymorphism analysis (Labrune et al., *Am. J. Hum. Genet.* 48:1115–1120 (1991)), single base primer extension (Kuppuswamy et al., *Proc. Natl. Acad. Sci. USA* 88:1143–1147 (1991), Goelet U.S. Pat. No. 6,004,744; Goelet U.S. Pat. No. 5,888,819), solid-phase ELISA-based oligonucleotide ligation assays (Nikiforov et al., *Nucl. Acids Res.* 22:4167–4175 (1994), dideoxy fingerprinting (Sarkar et al., *Genomics* 13:441–443 (1992)), oligonucleotide fluorescence-quenching assays (Livak et al, *PCR Methods Appl.* 4:357–362 (1995a)), 5'-nuclease allele-specific hybridization TaqMan™ assay (Livak et al., *Nature Genet.* 9:341–342 (1995)), template-directed dye-terminator incorporation (TDI) assay (Chen and Kwok, *Nucl. Acids Res.* 25:347–353 (1997)), allele-specific molecular beacon assay (Tyagi et al., *Nature Biotech.* 16: 49–53 (1998)), PinPoint assay (Haff and Smirnov, *Genome Res.* 7: 378–388 (1997)), dCAPS analysis (Neff et al., *Plant J.* 14:387–392 (1998)), pyrosequencing (Ronaghi et al, *Analytical Biochemistry* 267:65–71 (1999); Ronaghi et al PCT application WO 98/13523; Nyren et al PCT application WO 98/28440; www.pyrosequencing.com), mass spectrometry, e.g. the Masscode™ system (Howbert et al WO 99/05319; Howber et al WO 97/27331; www.rapigene.com; Becker et al PCT application WO 98/26095; Becker et al PCT application; WO 98/12355; Becker et al PCT application WO 97/33000; Monforte et al U.S. Pat. No. 5,965,363), invasive cleavage of oligonucleotide probes (Lyamichev et al *Nature Biotechnology* 17:292–296; www.twt.com), and high density oligonucleotide arrays (Hacia et al *Nature Genetics* 22:164–167; www.affymetrix.com).

Polymorphisms may also be detected using allele-specific oligonucleotides (ASO), which can be, for example, used in combination with hybridization based technology including Southern, northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide and temperature. These factors are important both during the hybridization itself and during subsequent washes performed to remove target polynucleotides that are not specifically hybridized. In practice, the conditions of the final, most stringent wash are most critical. In addition, the amount of target polynucleotide that is able to hybridize to the allele-specific oligonucleotide is also governed by such factors as the concentration of both the ASO and the target polynucleotide, the presence and concentration of factors that act to "tie up" water molecules so as to effectively concentrate the reagents (e.g., PEG, dextran, dextran sulfate, etc.) whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m = 81.5 + 16.6 \times (\log 10 \, [Na+]) + 0.41 \times (\% \, G+C) - 675/n$; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele.

While certain methods for detecting polymorphisms are described herein, other detection methodologies may be utilized. For example, additional methodologies are known and set forth, in Birren et al., *Genome Analysis*, 4:135–186, A Laboratory Manual. Mapping Genomes, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif. (1996); *The Maize Handbook*, Freeling and Walbot, eds., Springer-Verlag, New York, N.Y. (1994); *Methods in Molecular Medicine: Molecular Diagnosis of Genetic Diseases,* Elles, ed., Humana Press, Totowa, N.J. (1996); Clark, ed., *Plant Molecular Biology: A Laboratory Manual,* Clark, ed., Springer-Verlag, Berlin, Germany (1997).

Requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and user-friendly.

The genetic linkage of marker molecules can be established by a gene mapping model such as, without limitation, the flanking marker model reported by Lander and Botstein, *Genetics* 121:185–199 (1989) and the interval mapping, based on maximum likelihood methods described by Lander and Botstein, *Genetics* 121:185–199 (1989) and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A logio of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185–199 (1989) and further described by Arús and Moreno-González, *Plant Breeding,* Hayward et al., (eds.) Chapman & Hall, London, pp. 314–331 (1993).

In a preferred embodiment of the present invention the nucleic acid marker exhibits a LOD score of greater than 2.0, more preferably greater than 2.5, even more preferably greater than 3.0 or 4.0 with the trait or phenotype of interest. In a preferred embodiment, the trait of interest is altered tocopherol levels or compositions.

Additional models can be used. Many modifications and alternative approaches to interval mapping have been reported, including the use of non-parametric methods (Kruglyak and Lander, *Genetics* 139:1421–1428 (1995)). Multiple regression methods or models can be also be used in which the trait is regressed on a large number of markers (Jansen, *Biometrics in Plant Breeding,* van Oijen and Jansen (eds.), Proceedings of the Ninth Meeting of the Eucarpia Section Biometrics in Plant Breeding, The Netherlands, pp. 116–124 (1994); Weber and Wricke, *Advances in Plant Breeding,* Blackwell, Berlin, 16 (1994)). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447–1455 (1994), and Zeng, *Genetics* 136:1457–1468 (1994). Generally, the use of cofactors reduces the bias and sampling error of the estimated QTL positions (Utz and Melchinger, *Biometrics in Plant Breeding,* van Oijen and Jansen (eds.) Proceedings of the Ninth Meeting of the Eucarpia Section Biometrics in Plant Breeding, The Netherlands, pp. 195–204 (1994)), thereby improving the precision and efficiency of QTL mapping (Zeng, *Genetics* 136:1457–1468 (1994). These models can be extended to multi-environment experiments to analyze genotype-environment interactions (Jansen et al., *Theo. Appl. Genet.* 91:33–37 (1995)).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map the genetic position of traits. The choice of an appropriate mapping population often depends on the type of marker systems employed (Tanksley et al., *J. P. Gustafson and R. Appels* (eds.). Plenum Press, New York, pp. 157–173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as mapping populations. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (Reiter. *Proc. Natl. Acad. Sci. (U.S.A.)* 89:1477–1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus, a population is created consisting of individuals nearly like the recurrent parent but each individual carries varying amounts or a mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A*) 89:1477–1481 (1992)). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as mapping populations. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci. U.S.A.* 88:9828–9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

In an aspect of the present invention, one or more of the nucleic acid molecules of the present invention are used to determine the level (i.e., the concentration of mRNA in a sample, etc.) in a plant (preferably canola, maize, *Brassica campestris, Brassica napus*, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecules of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether an Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement, yield, etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem, pollen, etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissues. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477–484 (1984); Angerer et al., *Dev. Biol.* 112:157–166 (1985); Dixon et al., *EMBO J.* 10:1317–1324 (1991)). In situ hybridization may be used to measure the steady-state level of RNA accumulation (Hardin et al., *J. Mol. Biol.* 202:417–431 (1989)). A number of protocols have been devised for in situ hybridization, each with tissue preparation, hybridization, and washing conditions (Meyerowitz, *Plant Mol. Biol. Rep.* 5:242–250 (1987); Cox and Goldberg, In: *Plant Molecular Biology: A Practical Approach,* Shaw (ed.), pp. 1–35, IRL Press, Oxford (1988); Raikhel et al., *In situ RNA hybridization in plant tissues,* In: *Plant Molecular Biology Manual,* vol. B9:1–32, Kluwer Academic Publisher, Dordrecht, Belgium (1989)).

In situ hybridization also allows for the localization of proteins within a tissue or cell (Wilkinson, *In Situ Hybridization,* Oxford University Press, Oxford (1992); Langdale, *In Situ Hybridization* In: *The Maize Handbook,* Freeling and Walbot (eds.), pp. 165–179, Springer-Verlag, New York (1994)). It is understood that one or more of the molecules of the invention, preferably one or more of the nucleic acid molecules or fragments thereof of the invention, or one or more of the antibodies of the invention, may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.* 17:101–109 (1991); Gustafson et al., *Proc. Natl. Acad. Sci. (U.S.A.)* 87:1899–1902 (1990); Mukai and Gill, *Genome* 34:448–452 (1991); Schwarzacher and Heslop-Harrison, *Genome* 34:317–323 (1991); Wang et al., *Jpn. J. Genet.* 66:313–316 (1991); Parra and Windle, *Nature Genetics* 5:17–21 (1993)). It is understood that the nucleic acid molecules of the invention may be used as probes or markers to localize sequences along a chromosome.

Another method to localize the expression of a molecule is tissue printing. Tissue printing provides a way to screen, at the same time and on the same membrane, many tissue sections from different plants or at different developmental stages (Yomo and Taylor, *Planta* 112:35–43 (1973); Harris and Chrispeels, *Plant Physiol.* 56:292–299 (1975); Cassab and Varner, *J. Cell. Biol.* 105:2581–2588 (1987); Spruce et al., *Phytochemistry* 26:2901–2903 (1987); Barres et al., *Neuron* 5:527–544 (1990); Reid and Pont-Lezica, *Tissue Printing: Tools for the Study of Anatomy, Histochemistry and Gene Expression,* Academic Press, New York, N.Y. (1992); Reid et al., *Plant Physiol.* 93:160–165 (1990); Ye et al., *Plant J.* 1:175–183 (1991)).

One skilled in the art can refer to general reference texts for detailed descriptions of known techniques discussed herein or equivalent techniques. These texts include *Current Protocols in Molecular Biology* Ausubel, et al., eds., John Wiley & Sons, N. Y. (1989), and supplements through September (1998), *Molecular Cloning, A Laboratory Manual,* Sambrook et al., $2^{nd}$ Ed., Cold Spring Harbor Press, Cold Spring Harbor, N.Y. (1989), *Genome Analysis: A Laboratory Manual* 1: *Analyzing DNA,* Birren et al., Cold Spring Harbor Press, Cold Spring Harbor, N.Y. (1997); *Genome Analysis: A Laboratory Manual* 2: *Detecting Genes,* Birren et al., Cold Spring Harbor Press, Cold Spring Harbor, N.Y. (1998); *Genome Analysis: A Laboratory Manual* 3: *Cloning Systems,* Birren et al., Cold Spring Harbor Press, Cold Spring Harbor, N.Y. (1999); *Genome Analysis: A Laboratory Manual* 4: *Mapping Genomes,* Birren et al., Cold Spring Harbor Press, Cold Spring Harbor, N.Y. (1999); *Plant Molecular Biology: A Laboratory Manual,* Clark, Springer-Verlag, Berlin, (1997), *Methods in Plant Molecular Biology,* Maliga et al., Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Having now generally described the invention, the same will be more readily understood through reference to the following examples which are provided by way of illustration and are not intended to be limiting of the present invention unless specified.

Each periodical, patent, and other document or reference cited herein is herein incorporated by reference in its entirety.

EXAMPLE 1

Amplification of AANT1 Coding Region

A published partial sequence of a putative AANT1 (Saint-Guily et al., Plant Physiol. 100(2), 1069–1071 (1992)) is used to search an EST database, and three full-length clones are identified: LIB3176-057-P1-K1-B12, LIB3234-001-P1-K1-G3, and LIB3176-083-P1-K1-F2. An AANT1 coding region is PCR-amplified using the forward primer AANT1F 5'-GGA TCC GCGGCCGCA CCA TGG TTG ATC AAG TTC AGC A (SEQ ID NO: 3) and the reverse primer AANT1R 5'-GAG CTCCTGCAGGAA GCT TTT AGG CAC CTC CTG ATC CGT-3' (SEQ ID NO: 4). The AANT1F primer contains a NotI site (underlined) upstream of the start codon (italics) while the AANT1R primer contains an Sse8387I site (underlined) downstream of the stop codon (italics). A PCR product is generated and cloned into pCR2.1, and the insert is verified by sequencing both strands

EXAMPLE 2

Creation of pCGN11301 and pMON66454

Figure 2:
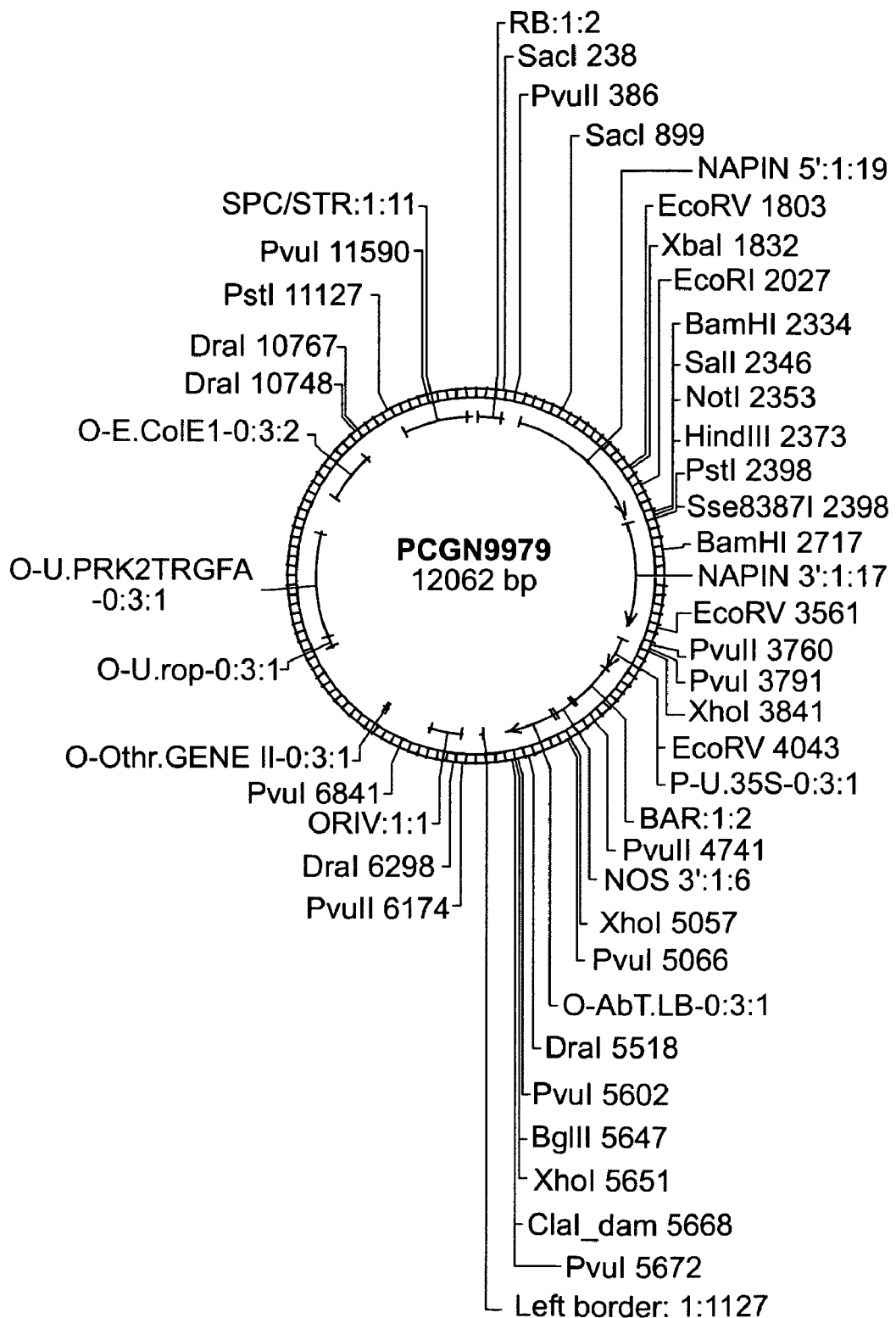
FIG. 2 is a schematic of construct pCGN9979.
Figure 3:
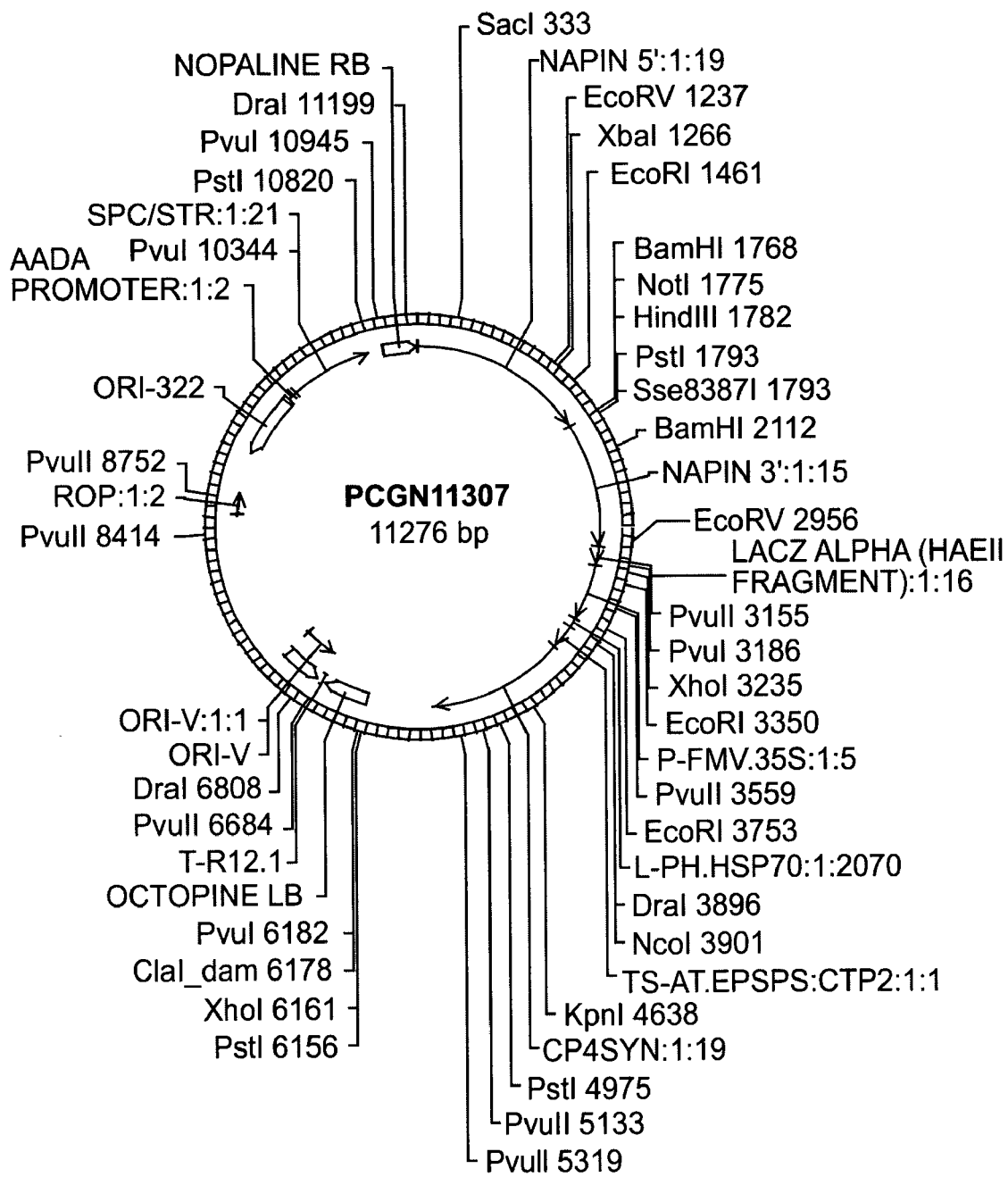
FIG. 3 is a schematic of construct pCGN11307.
Figure 4:
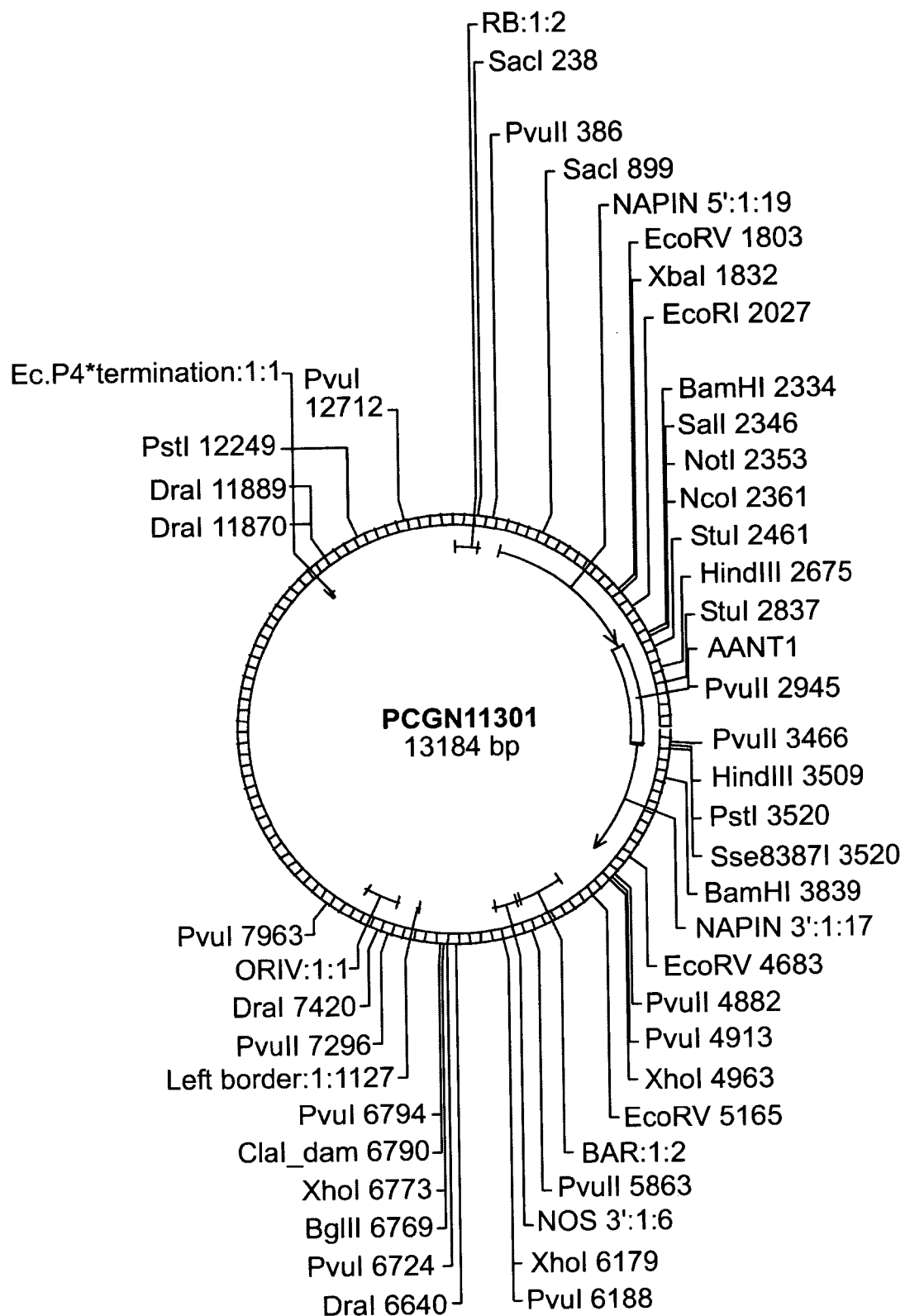
FIG. 4 is a schematic of construct pCGN11301.
Figure 5:
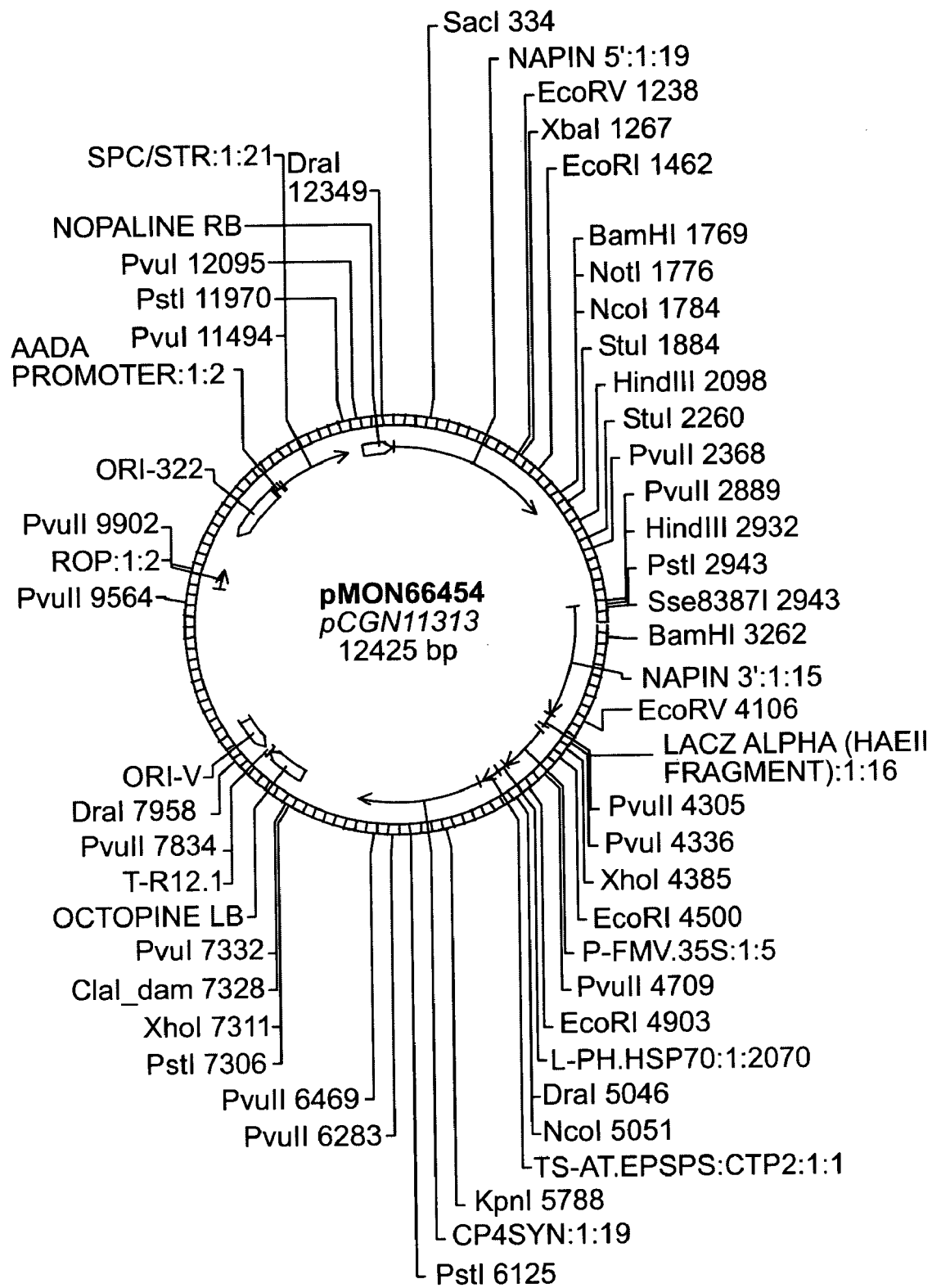
FIG. 5 is a schematic of construct pMON66454.
Figure 6:
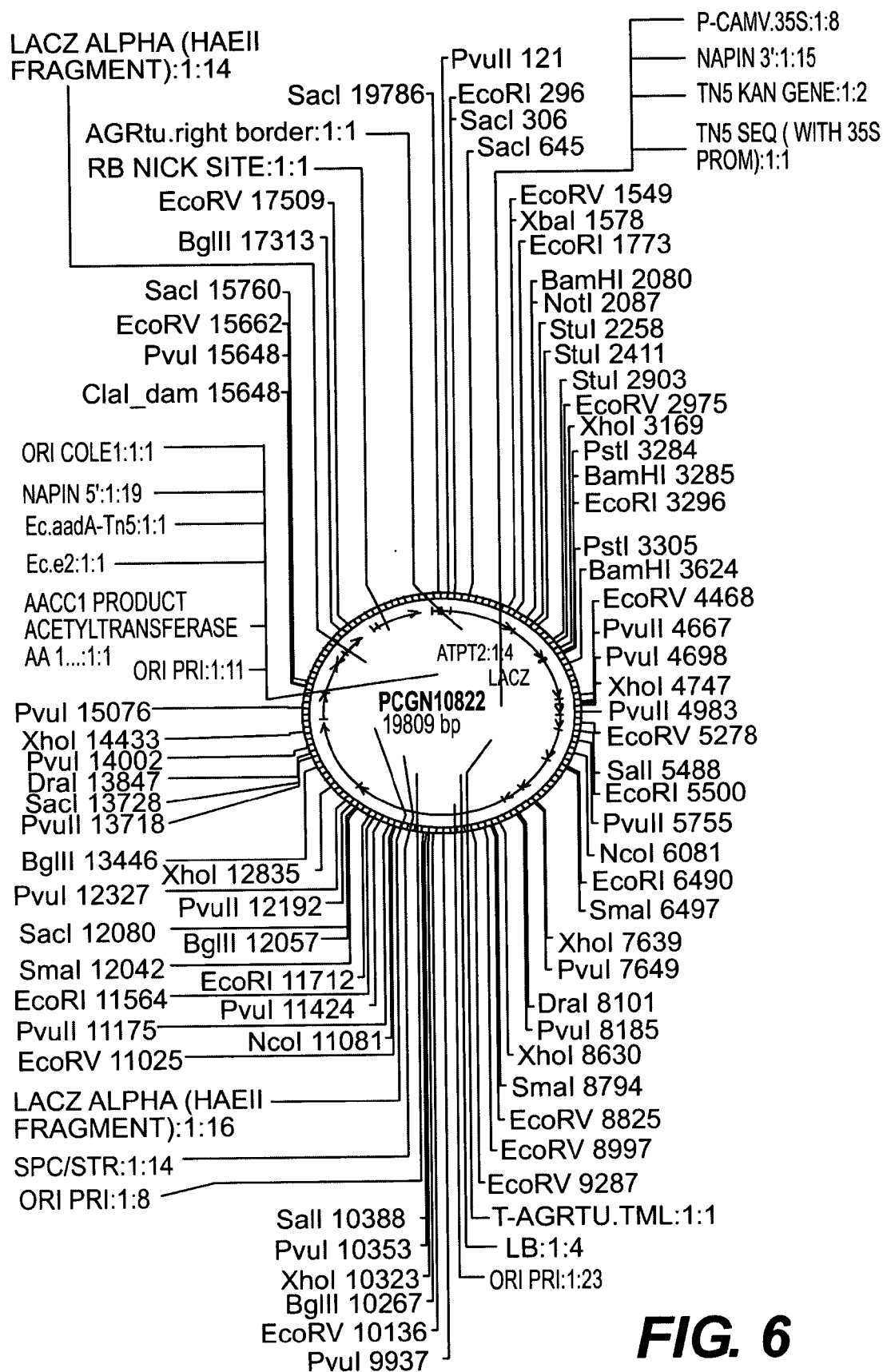
FIG. 6 is a schematic of construct pCGN10822.
Figure 7:
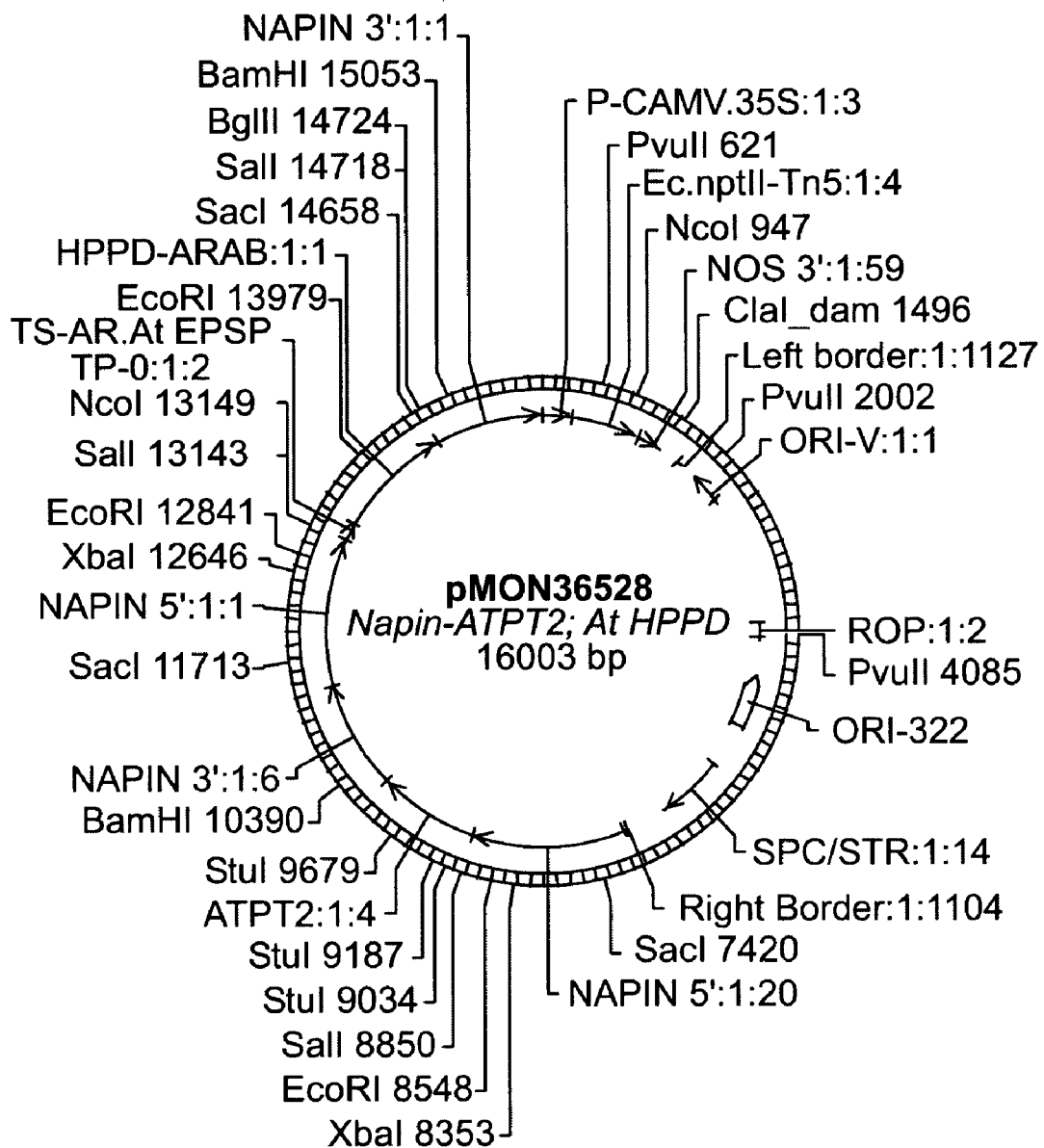
FIG. 7 is a schematic of construct pMON36528.

The NotI/Sse8387I fragment from example 1 is inserted into the NotI/Sse8387I sites of the napin expression cassettes in pCGN9979, which is shown in FIG. 2, and pCGN11307, which is shown in FIG. 3. pCGN9979 is designed for use in *Arabidopsis* and pCGN11307 is designed for use in *Brassica*. Both pCGN9979 and pCGN11307 contain a seed specific expression cassette using the *Brassica* seed storage protein (napin) gene promoter (Kridl et al., Seed Sci. Res. 1:209–219 (1991)). The resulting plasmids are pCGN11301 (for pCGN9979) and pMON66454 (for pCGN11307), which are shown in FIGS. 4 and 5, respectively.

EXAMPLE 3

Transformation of *Arabidopsis* with pCGN11301

*Arabidopsis* plants are grown for transformation with pCGN11301. 4.5 inch Kord pots are filled with Metro Mix 200 soil. Pots are placed into Kord 1040 green flats with holes, which are placed into Kord 1040 white flats without holes. The flats are filled with 1" of reverse osmosis water and a humidity dome is placed over each of the flats. The pots are allowed to soak up water for several hours to overnight until the soil is completely moistened. Eight inch fiberglass screens are placed over the soil and secured and seeds are sown. The flats are placed in a chamber at 22° C. for a 16/8 photoperiod at 55% relative humidity and 234 µMol/s/m². After germination the domes are raised slightly and then removed after three days. The plants are bottom watered as needed with Plantex 15-15-18 at 50 PPM N. The plants are thinned down to 7 plants per pot 3 weeks after seeding. The primary bolts at the base of the plant are pruned to promote secondary growth. The plants are bottom watered to saturate the soil prior to transformation. Plants are ready for transformation when secondary bolts are emerging (for vacuum infiltration transformation) or when bolts are 2–10 cm (for dipping method of transformation).

To transform the plants that are ready for transformation, 6 ml of LB (75 mg/l spectinomycin, 50 mg/l kanamycin, and 25 mg/l chloramplenicol) is inoculated with a single *Agrobacterium* colony containing pCGN11301 and incubated at 200 rpm and 30° C. for about 24 hours.

The 6 ml culture is then added to 300 ml of the same medium in a 1 liter Erlenmeyer flask and the culture is incubated at the same conditions for about 18 hours.

The pots containing the plants to be transformed are immersed in water for about 30 minutes prior to dipping.

The *Agrobacterium* culture is centrifuged at 5000×g for 12 minutes at 15° C., and the pellet is resuspended in 300 ml of 5% sucrose solution in water. Fifty ml aliquots of this suspension are placed into 200 ml of 5% sucrose solution, to which 125 μl of Silwet L-77 (Lehle Seeds) has been added. This mixture is poured into a plastic dish of about 14 cm diameter, with a capacity of about 850 ml.

The above-ground portion of the plants are dipped in the *Agrobacterium* solution for 2–5 seconds, with gentle agitation. Excess *Agrobacterium* solution is blotted with paper towels. The dipped plants are placed on their sides with the bolts on top of paper towels, and then are placed in a flat and covered with a plastic dome. The cover is kept in place for 16 to 25 hours to maintain high humidity.

The pots are not watered for about 5 days following dipping. After 5 days, the pots are provided with water and the plants are grown under normal conditions. Watering is stopped when the seeds become mature (in about 4 weeks) and the dry seed is harvested.

Selection involves sprinkling the transformed $T_1$ seeds directly onto the soil and then vernalizing them at 4° C. in 8 hours light, 16 hours dark for 4–7 days. The seeds are then transferred to 22° C. in 16 hours light and sprayed with a 1:200 dilution of Finale (Basta) at 7 days and again at 14 days.

EXAMPLE 4

Transformation of Canola with pMON66454.

In this example, all tissue is handled aseptically in a laminar flow hood (see Radke SE et al., *Plant Cell Reports* 11: 499–505 (1992)).

*Agrobacterium* strains ABI, EHA105, and EHA101 can be used for canola transformation. The canola cultivar Ebony can be used.

For the following procedure, culture room shelves are lit by two Cool White HO, and one Gro-Lux HO (or equivalent), fluorescent bulbs per shelf. The temperature of culture rooms is 22° C.

The seeds are surface-sterilized in a wire mesh tea strainer, for 2 minutes in 95% ethanol or 70% isopropanol, followed by 30 minutes in 20% bleach solution (1% NaOCl) with one drop of Tween 20 per 100 ml. The seeds are then rinsed 4 times with sterile reverse osmosis water. Sterilized seed is plated on modified 1/10×MS medium (1/10×MS minimal organics medium (Gibco 510-1118; final sucrose 0.3%), pyridoxine 50 ug/l, nicotinic acid 50 ug/l, glycine 200 ug/l, Phytagar (Gibco) 6 g/l, pH 5.8; 20 boxes per liter) at 25 seeds per Magenta box. The seed is kept at 24° C. for 16 hours light/day and 15–35 uE/m2/sec under shade. Complete darkness may be used during the last 24 hours to increase etiolation.

*Brassica napus* feeder plates are prepared 1 day before explant cutting. 0.5 ml of a *Brassica napus* cell suspension (10 ml) that has been subcultured into 100 ml KCMS 0/0.2/0.1 medium (MS salts (Gibco 500-1117), KH2PO4 200 mg/l, inositol 100 mg/l, thiamine-HCl 1.3 mg/l, 2,4-D 0.2 mg/l (Sigma D8407), kinetin 0.1 mg/l (Sigma K0753), sucrose 3%, pH 5.5; 100 ml per 500 ml Erlenmeyer flask), at 25° C. with continuous light at 90 rpm is spread onto each plate of MS 0/1/0 medium and the plates are stacked in a sealed plastic sleeve and incubated at 24° C. in indirect continuous light.

Hypocotyl segments (2–4 mm) are excised from etiolated one-week-old seedlings (4 to 14 days old). Segments are cut in a petri dish with several ml of water to prevent dehydration. Explants are placed onto a filter paper (Whatman 1001-082) and laid over the tobacco feeder cells on MS 0/1/0 cocultivation medium (MS salts (Gibco 500-1117), myo-inositol 100 mg/l, thiamine-HCl 1.3 mg/l, $KH_2PO_4$ 200 mg/l, 2,4-D1 mg/l, sucrose 3%, Phytagar 6 g/l, pH 5.8; 30 plates per liter) at 50 explants per plate (100×15 mm) and the plates are stacked in a sealed plastic sleeve and incubated for 18–24 hours at 24° C. in indirect continuous light.

A single colony of *Agrobacterium* containing pMON66454 is grown overnight in 5 ml MG/L broth (Mannitol 5 g/l, L-glutamic acid 1 g/l, KH2PO4 250 mg/l, NaCl 100 mg/l, MgSO4.7h20 100 mg/l, biotin 1 ug/l, tryptone 5 g/l, yeast extract 2.5 g/l, pH 7.0) in a large culture tube, at 30° C., in the dark, at 200 rpm. The Agrobacterium suspension OD is measured at 550 nm on a spectrophotometer. The overnight culture is diluted with MG/L broth to 0.05 OD (equivalent to about $1\times10^8$ bacteria/ml). The pre-incubated explants are inoculated for 10 minutes in $1\times10^8$ bacteria/ml; 200–400 explants per 10 ml inoculum. Inoculated explants are drained well, returned to the feeder plates, and cocultivated with *Agrobacterium* for 2 days. Plates are stacked in a sealed plastic sleeve and incubated at 24° C. in indirect continuous light.

Cocultivated explants are transferred to B5 0/1/0 callus induction medium (B5 salts (Gibco 85-5068), B5 vitamins (1 mg/l nicotinic acid, 1 mg/l pyridoxine-HCl, 10 mg/l thiamine-HCl), 100 mg/l inositol, 1 mg/l 2,4-D, sucrose 3%, 500 mg/l carbenicillin, 50 mg/l Timentin, 6 g/l Phytagar, pH5.8, 30 plates per liter) supplemented with 500 mg/l carbenicillin and 50 mg/l Timentin to inhibit *Agrobacterium*. There are about 40–50 explants per plate (100×15 mm). The plates are sealed with Parafilm. Explants remain on B5 0/1/0 for 7 days (to achieve a total of about 10 days exposure to 2,4-D) at 24° C. in continuous light at 85 uE/m2/s.

Explants are transferred to B5BZ shoot regeneration medium (B5 salts (Gibco 85-5068), B5 vitamins (1 mg/l nicotinic acid, 1 mg/l pyridoxine-HCl, 10 mg/l thiamine-HCl), 100 mg/l inositol, BAP 3 mg/l (Sigma B3408), zeatin 1 mg/l (Sigma Z0164), sucrose 1%, Phytagar 6 mg/l, pH 5.8; 25 plates per liter, silver nitrate (3 mg/l) is included during the first two weeks on B5BZ medium) containing 500 mg/l carbenicillin with 45 mg/l glyphosate. The plates (100×25 mm) are sealed with Parafilm and incubated at 24° C. in continuous light at 85 uE/m2/s. Explants are transferred to fresh medium every second week and plating density is reduced to 20–25 explants after two weeks on B5BZ. Shoots regenerate from kanamycin-selected calli 5 to 9 weeks after culture initiation.

Green, glyphosate selected shoots are transferred to hormone-free B5 shoot maturation medium (B5 salts (Gibco 85-5068) B5 vitamins (1 mg/l nicotinic acid, 1 mg/l pyridoxine-HCl, 10 mg/l thiamine-HCl), 100 mg/l inositol, sucrose 1%, Phytagar 6 g/l, pH 5.8; 25 plates per liter) containing 300 mg/l carbenicillin and 45 mg/l glyphosate. Multiple shoots from a single callus are kept together as one event with 9 events per plate. The plates are sealed with paraflim and shoots remain on maturation medium for 7–14 days at 24° C. for 16 hours light/day at 85 uE/m2/s.

Shoots that remain green on maturation medium are trimmed to one or two nodes and are transferred to B5 root induction medium (B5 salts (Gibco 85-5068), B5 vitamins (1 mg/l nicotinic acid, 1 mg/l pyridoxine-HCl, 10 mg/l thiamine-HCl), 100 mg/l inositol, IBA 2 mg/l, sucrose 1%, Phytagar 6 g/l, pH 5.8; 20 boxes per liter) containing 45 mg/l glyphosate with 5 events per Magenta box at 24° C. for 16 hours light/8 hours dark at 85 uE/m2/s. Roots develop over a period of 4–6 weeks and stems are re-cut to encourage rooting, as needed.

EXAMPLE 5

Testing Seed Tocopherol Levels

Arabidopsis plants resistant to Basta representing 20 independent transformation events are grown and seeds are harvested to produce $T_2$ seeds. The $T_2$ seeds are harvested and tested for tocopherol levels. FIG. 1 shows the total seed tocopherol level (nanograms per milligram) for 20 plant lines. Tocopherol levels are determined by adding 10 to 15 mg of Arabidopsis seed into a 2 mL microtube. A mass of 1 g of 0.5 mm microbeads (Biospecifics Technologies Corp., Lynbrook, N.Y.) and 500 µl of 1% pyrogallol (Sigma Chem, St. Louis, Mo.) in ethanol containing 5 µg/mL tocol, are added to the tube. The sample is shaken twice for 45 seconds in a FastPrep (Bio101/Savant) at a speed of 6.5. The extract is filtered (Gelman PTFE acrodisc 0.2 µm, 13 mm syringe filters, Pall Gelman Laboratory Inc, Ann Arbor, Mich.) into an autosampler tube. HPLC is performed on a Zorbax silica HPLC column, 4.6 mm×250 mm (5 µm) with a fluorescent detection using a Hewlett Packard HPLC (Agilent Technologies, Palo Alto Calif.). Sample excitation is performed at 290 nm, and emission is monitored at 336 nm. Tocopherols are separated with a hexane methyl-t-butyl ether gradient using, an injection volume of 20 µl, a flow rate of 1.5 ml/min, and a run time of 12 min (40° C.). Tocopherol concentration and composition is calculated based on standard curves for α, β, δ, and γ-tocopherol using Chemstation software (Agilent Technologies, Palo Alto Calif.).

EXAMPLE 6

Creation of Transformed Plants with Single and Multiple Gene Constructs

Canola, Brassica napus and soybean plants are transformed with a variety of DNA constructs using a particle bombardment approach essentially as set forth in Christou, In Particle Bombardment for the Genetic Engineering of Plants, Biotechnology Intelligence Unit, Academic Press, San Diego, Calif. (1996) or using Agrobacterium mediated transformation. Two sets of DNA constructs are produced. The first set of constructs are "single gene constructs." Each of the following genes is inserted into a separate plant DNA construct under the control of a napin promoter (Kridl et al., Seed Sci. Res. 1:209:219 (1991)) and the products of the genes can be targeted to the plastid by an encoded plastid target peptide such as CTP1 (Keegstra, Cell 56(2):247–53 (1989); Nawrath, et al., Proc. Natl. Acad. Sci. U.S.A. 91:12760–12764 (1994)): an E. herbicola tyrA gene (Xia et al., J. Gen. Microbiol. 138:1309–1316 (1992)), a plant slr1736 gene (in Cyanobase (www.kazusa.orjp/cyanobase)), a plant ATPT2 gene (Smith et al., Plant J. 11. 83–92 (1997)), an E. coli dxs gene (Lois et al., Proc. Natl. Acad. Sci. U.S.A. 95 (5):2105–2110 (1998)), a dxr gene (Takahashi et al. Proc. Natl. Acad. Sci. U.S.A. 95 (17), 9879–9884 (1998)), an Arabidopsis thaliana HPPD gene (Norris et al., Plant Physiol. 117:1317–1323 (1998)), an Arabidopsis thaliana GGPPS gene (Bartley and Scolnik, Plant Plysiol. 104: 1469–1470 (1994)), a AANT1 gene (Saint Guily, et al., Plant Physiol., 100(2).1069–1071 (1992)), a GMT gene (WO 00/32757, WO 00/10380), a slr1737 gene (in Cyanobase (www.kazusa.orjp/cyanobase), an MT1 gene (The sequence of the Synechocystis MT1 (NCBI General Identifier Number 1653572) was used in a blast search against ESTs of Anabaena sp. strain PCC 7120 (Kaneko 2001) and a sequence with substantial homology to the Synechocystis MT1 was found in a blast search against ESTs of Anabaena sp. strain PCC 7120 (Kaneko et al., DNA Research 8(5): 205–213 (2001)), a TMT2 gene (as disclosed in U.S. application Ser. No. 60/330,563, filed on Oct. 25, 2001, which is herein incorporated by reference in its entirety), and an antisense construct for homogentisic acid dioxygenase (Sato et al., J. DNA Res. 7 (1):31–63 (2000)). Each construct is transformed into at least one canola, Brassica napus, and soybean plant. Plants expressing each of these genes are selected to participate in additional crosses. The tocopherol composition and level in each plant is also analyzed using the method set forth in example 5. Crosses are carried out for each species to generate transgenic plants having one or more of the following combinations of introduced genes: tyrA, slr1736, ATPT2, dxs, dxr, GGPPS, HPPD, GMT, AANT1, slr 1737, MT1, TMT2, and an antisense construct for homogentisic acid dioxygenase.

The tocopherol composition and level in each plant generated by the crosses (including all intermediate crosses) is also analyzed using the method set forth in example 5. Progeny of the transformants from these constructs will be crossed with each other to stack the additional genes to reach the desired level of tocopherol.

A second set of DNA constructs is generated and referred to as the "multiple gene constructs". The multiple gene constructs contain multiple genes each under the control of a napin promoter (Kridl et al., Seed Sci. Res. 1.209:219 (1991)) and the products of each of the genes are targeted to the plastid by an encoded plastid target peptide. The multiple gene construct can have two or more of the following genes: tyrA, slr1736, ATPT2, dxs, dxr, GGPPS, HPPD, GMT AANT1, slr 1737, MT1, TMT2, and an antisense construct for homogentisic acid dioxygenase.

Each construct is then transformed into at least one canola, Brassica napus and soybean plant. The tocopherol composition and level in each plant is also analyzed using the method set forth in example 5. Progeny of the transformants from these constructs will be crossed with each other to stack the additional genes to reach the desired level of tocopherol.

EXAMPLE 7

Transformation of Canola with pMON66454 and Measurement of Total Tocopherol Composition Canola plants are transformed using Agrobacterium as in Example 4 with the vector pMON66454 (described in Example 2) which contains a coding region for AANT1. Plants are grown, and seeds are harvested and tested for tocopherol levels essentially as described in Example 5 for Arabidiopsis seeds. Table 1 shows the total seed tocopherol level for control plants and several plants generated from separate transformation events (given in nanograms per milligram of seed). The average tocopherol levels expressed in control seed is 325+/−36 ng/mg of seed, and the average tocopherol levels for seed from R1 plants bearing the vector pMON66454 is 338+/−36 ng/mg of seed.

TABLE 1

| Strain ID | Generation | Line | ng total tocopherol/mg seed |
|---|---|---|---|
| EBONY | VARIETY | Control | 338.49 |
| EBONY | VARIETY | Control | 312.45 |

TABLE 1-continued

| Strain ID | Generation | Line | ng total tocopherol/mg seed |
|---|---|---|---|
| EBONY | VARIETY | Control | 319.57 |
| EBONY | VARIETY | Control | 273.61 |
| EBONY | VARIETY | Control | 287.25 |
| EBONY | VARIETY | Control | 385.61 |
| EBONY | VARIETY | Control | 357.54 |
| EBONY | VARIETY | Control | 326.97 |
| 66454-SP30052-20 | R1 | AANT1 | 292.06 |
| 66454-SP30052-10 | R1 | AANT1 | 298.16 |
| 66454-SP30052-5 | R1 | AANT1 | 299.78 |
| 66454-SP30052-26 | R1 | AANT1 | 300.15 |
| 66454-SP30052-15 | R1 | AANT1 | 305.26 |
| 66454-SP30052-3 | R1 | AANT1 | 305.92 |
| 66454-SP30052-27 | R1 | AANT1 | 309.42 |
| 66454-SP30052-23 | R1 | AANT1 | 312.7 |
| 66454-SP30052-30 | R1 | AANT1 | 312.9 |
| 66454-SP30052-17 | R1 | AANT1 | 315.56 |
| 66454-SP30052-29 | R1 | AANT1 | 317.56 |
| 66454-SP30052-4 | R1 | AANT1 | 318.15 |
| 66454-SP30052-1 | R1 | AANT1 | 321.96 |
| 66454-SP30052-18 | R1 | AANT1 | 325.64 |
| 66454-SP30052-21 | R1 | AANT1 | 329.76 |
| 66454-SP30052-9 | R1 | AANT1 | 330.82 |
| 66454-SP30052-8 | R1 | AANT1 | 332.96 |
| 66454-SP30052-24 | R1 | AANT1 | 337.17 |
| 66454-SP30052-14 | R1 | AANT1 | 339.9 |
| 66454-SP30052-25 | R1 | AANT1 | 343.81 |
| 66454-SP30052-13 | R1 | AANT1 | 348.87 |
| 66454-SP30052-11 | R1 | AANT1 | 352.52 |
| 66454-SP30052-16 | R1 | AANT1 | 354.4 |
| 66454-8P30052-22 | R1 | AANT1 | 364.8 |
| 66454-SP30052-7 | R1 | AANT1 | 364.87 |
| 66454-SP30052-28 | R1 | AANT1 | 383.6 |
| 66454-SP30052-2 | R1 | AANT1 | 406.13 |
| 66454-SP30052-12 | R1 | AANT1 | 407.44 |
| 66454-SP30052-19 | R1 | AANT1 | 408.81 |
| 66454-SP30052-6 | R1 | AANT1 | 411.82 |

EXAMPLE 8

Transformed Plants with AANT1 and Other Tocopherol Biosynthesis Genes

Canola, *Brassica napus, Arabidopsis*, and soybean plants are transformed with a variety of DNA constructs using a particle bombardment approach essentially as set forth in Christou, In *Particle Bombardment for the Genetic Engineering of Plants*, Biotechnology Intelligence Unit, Academic Press, San Diego, Calif. (1996) or using *Agrobacterium* mediated transformation. Two sets of DNA constructs are produced. The first set of constructs are "single gene constructs". Each of the following genes is inserted into a separate plant DNA construct under the control of a napin promoter (Kridl et al., *Seed Sci. Res.* 1:209:219 (1991)) and the products of the genes can be targeted to the plastid by an encoded plastid target peptide such as CTP1 (Keegstra, *Cell* 56(2):247–53 (1989); Nawrath, et al., *Proc. Natl. Acad. Sci. U.S.A.* 91:12760–12764 (1994)) or CTP2): an *E. herbicola* tyrA gene (Xia et al., *J. Gen. Microbiol.* 138:1309–1316 (1992)), an slr1736 gene (in Cyanobase on the world wide web at: kazusa.orjp/cyanobase), a plant ATPT2 gene (Smith et al., *Plant J.* 11: 83–92 (1997)), a dxs gene (Lois et al., *Proc. Natl. Acad. Sci. U.S.A.* 95 (5):2105–2110 (1998)), a dxr gene (Takahashi et al., *Proc. Natl. Acad. Sci. U.S.A.* 95 (17), 9879–9884 (1998)), an *Arabidopsis thaliana* HPPD gene (Norris et al., *Plant Physiol.* 117:1317–1323 (1998)), a GGH gene (Keller et al., *Eur. J. Biochem.* 251:413–417 (1998)), an *Arabidopsis thaliana* GGPPS gene (Bartley and Scolnik, *Plant Physiol.* 104:1469–1470 (1994)), a AANT1 gene (Saint Guily, et al., *Plant Physiol.*, 100(2):1069–1071 (1992)), an MT1 gene (The sequence of the Synechocystis MT1 (NCBI General Identifier Number1653572) was used in a blast search against ESTs of Anabaena sp. strain PCC 7120 (Kaneko 2001). A sequence with substantial homology to the Synechocystis MT1 was found in a blast search against ESTs of *Anabaena* sp. strain PCC 7120 (Kaneko et al., DNA Research 8(5): 205–213 (2001)), a TMT2 gene (as disclosed in U.S. application Ser. No. 60/330,563, filed on Oct. 25, 2001, which is herein incorporated by reference in its entirety), a GMT gene (as disclosed in U.S. application Ser. No. 60/312,758, filed on Aug. 17, 2001, which is herein incorporated by reference in its entirety and WO 00/32757, WO 00/10380), and an slr1737 gene (in Cyanobase (on the world wide web at kazusa.or.jp/cyanobase), and an antisense construct for homogentisic acid dioxygenase (Sato et al., *J. DNA Res.* 7 (1):31–63 (2000))). Each construct is transformed into at least one canola, *Brassica napus, Arabidposis* and soybean plant. Plants expressing each of these genes are selected to participate in additional crosses. The tocopherol composition and level in each plant is also analyzed using the method set forth in example 5. Crosses are carried out for each species to generate transgenic plants having one or more of the following combination of introduced genes: tyrA, slr1736, ATPT2, dxs, dxr, GGH, GGPPS, HPPD, MT1, TMT2, GMT AANT1, slr 1737, and an antisense construct for homogentisic acid dioxygenase. The tocopherol composition and level in each plant generated by the crosses (including all intermediate crosses) is also analyzed using the method set forth in example 5. Progeny of the transformants from these constructs are crossed with each other to stack the additional genes to reach the desired level of tocopherol.

A second set of DNA constructs is generated and referred to as the "multiple gene constructs." The multiple gene constructs contain multiple genes each under the control of a napin promoter (Kridl et al., *Seed Sci. Res.* 1:209:219 (1991)) and the products of each of the genes are targeted to the plastid by an encoded plastid target peptide. The multiple gene construct can have two or more of the following genes: tyrA, slr1736, ATPT2, dxs, dxr, GGH, GGPPS, HPPD, MT1, TMT2, GMT AANT1, slr 1737, and an antisense construct for homogentisic acid dioxygenase.

Each construct is then transformed into at least one canola, *Brassica napus, Arabidopsis*, and soybean plant. The tocopherol composition and level in each plant is also analyzed using the method set forth in example 5. Progeny of the transformants from these constructs are crossed with each other to stack the additional genes to reach the desired level of tocopherol.

EXAMPLE 9

Figure 10B:
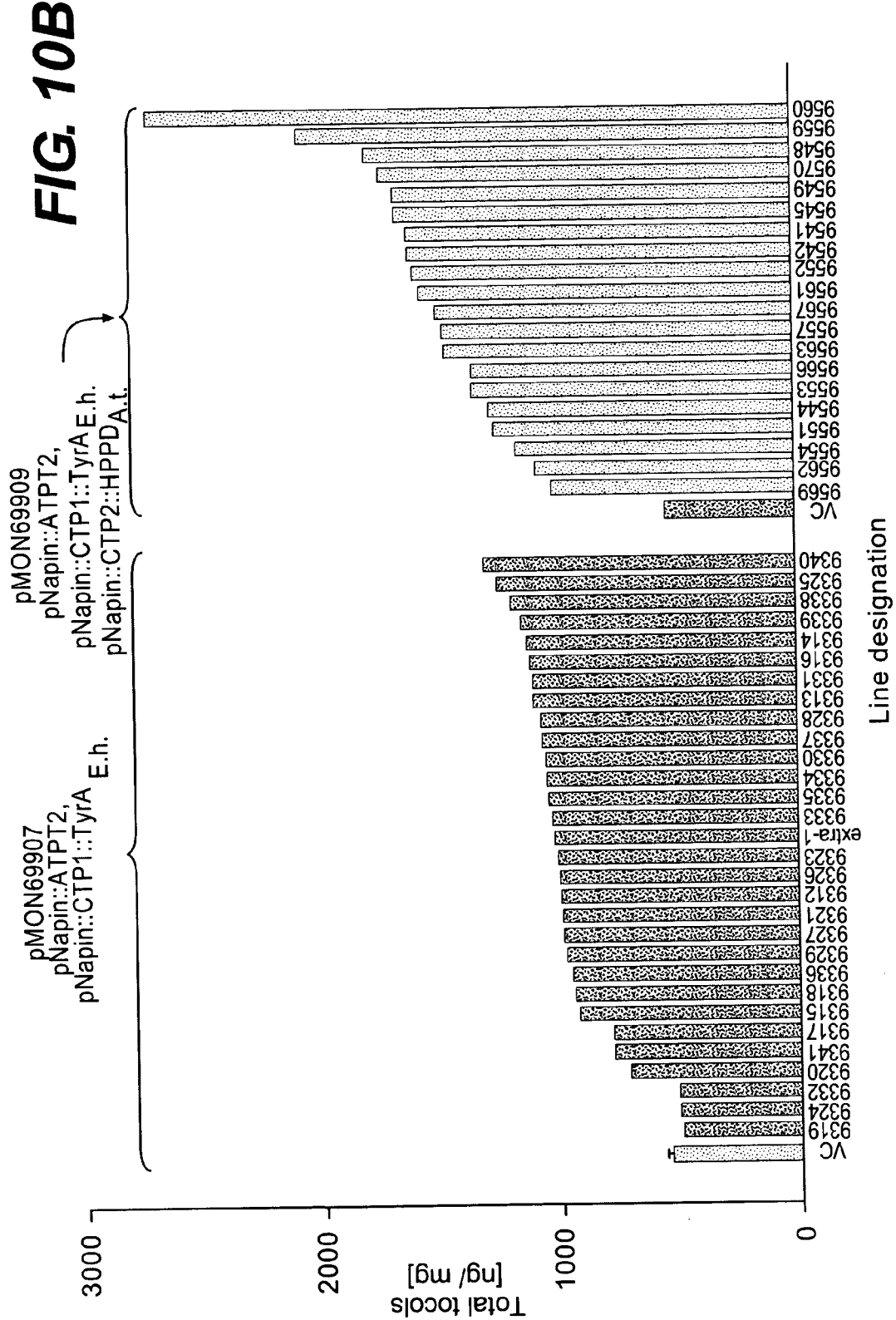
FIG. 10 depicts the total tocopherol and tocotrienol content of *Arabidopsis thaliana* seeds from wild type plants and several plant lines separately transformed with the plasmid vectors pCGN10822, pMON36528, pMON69907 and pMON69909.
Figure 11A:
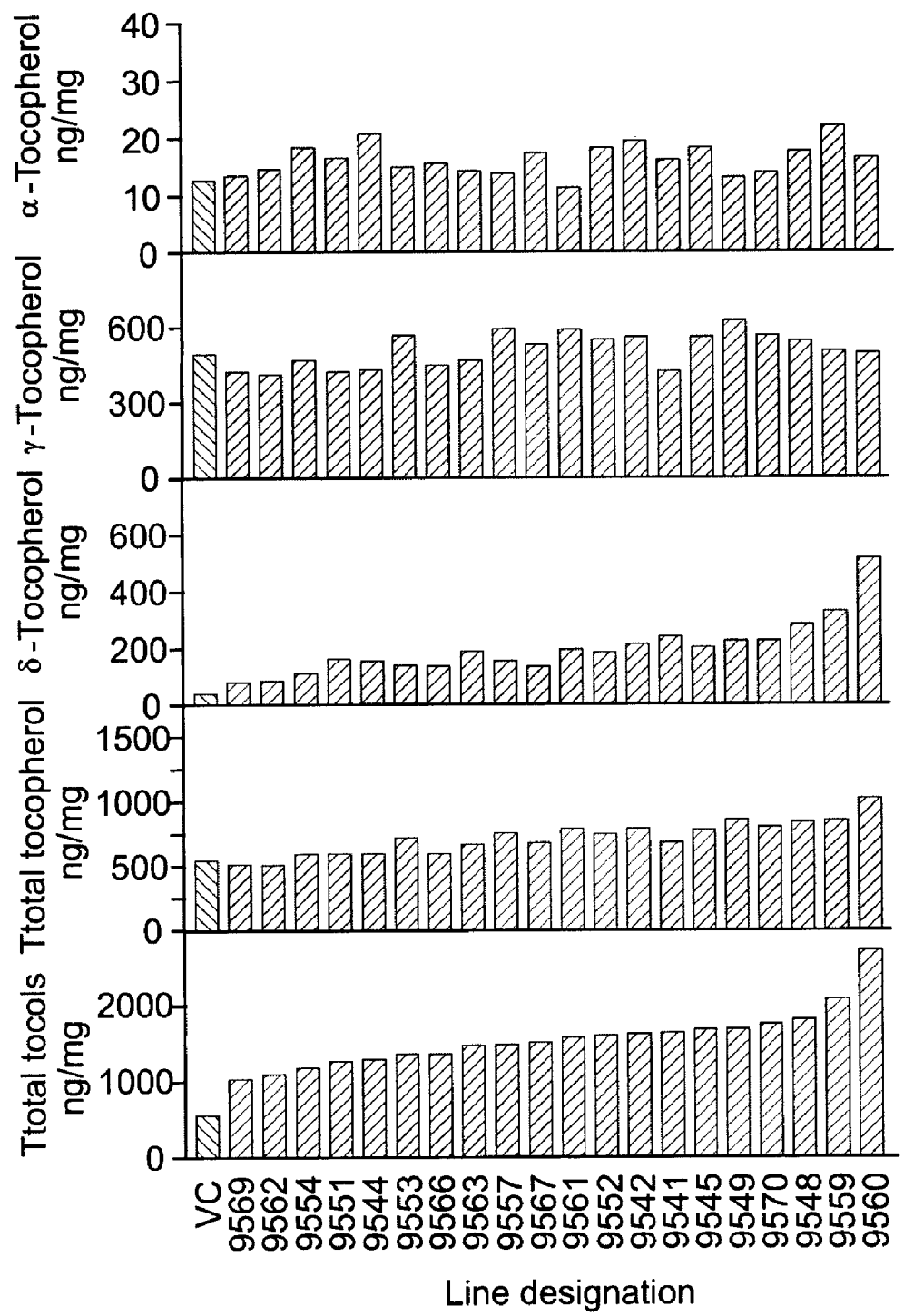
FIG. 11 represents an analysis of tocopherol and tocotrienol content of arabidopsis seeds from plant lines transformed with the vector pMON69909 relative to wild type plant seeds.
Figure 11B:
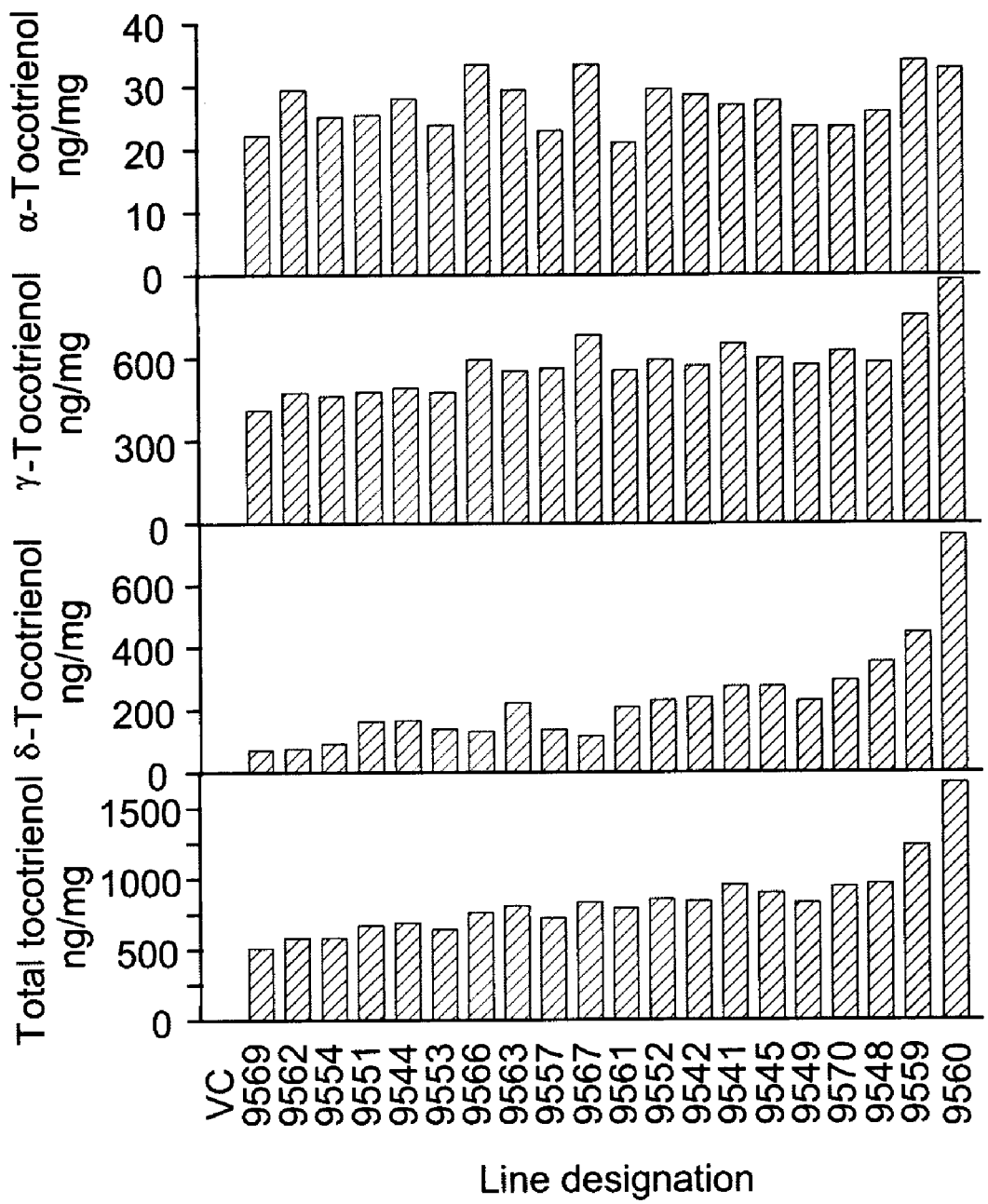
Figure 12A:
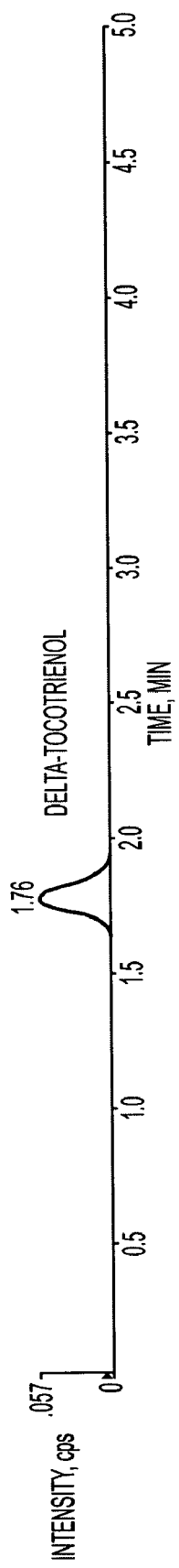
FIG. 12 is an LC/MS standard graph.
Figure 12A:
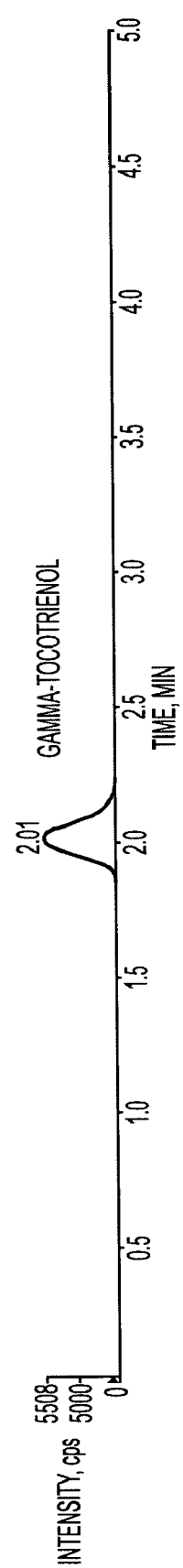
Figure 12A:
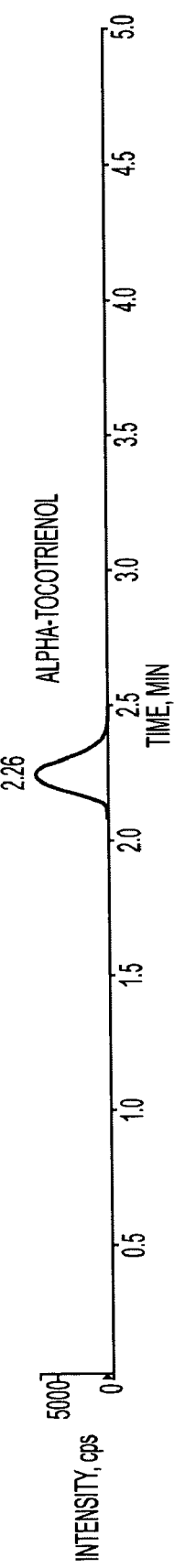
Figure 12B:
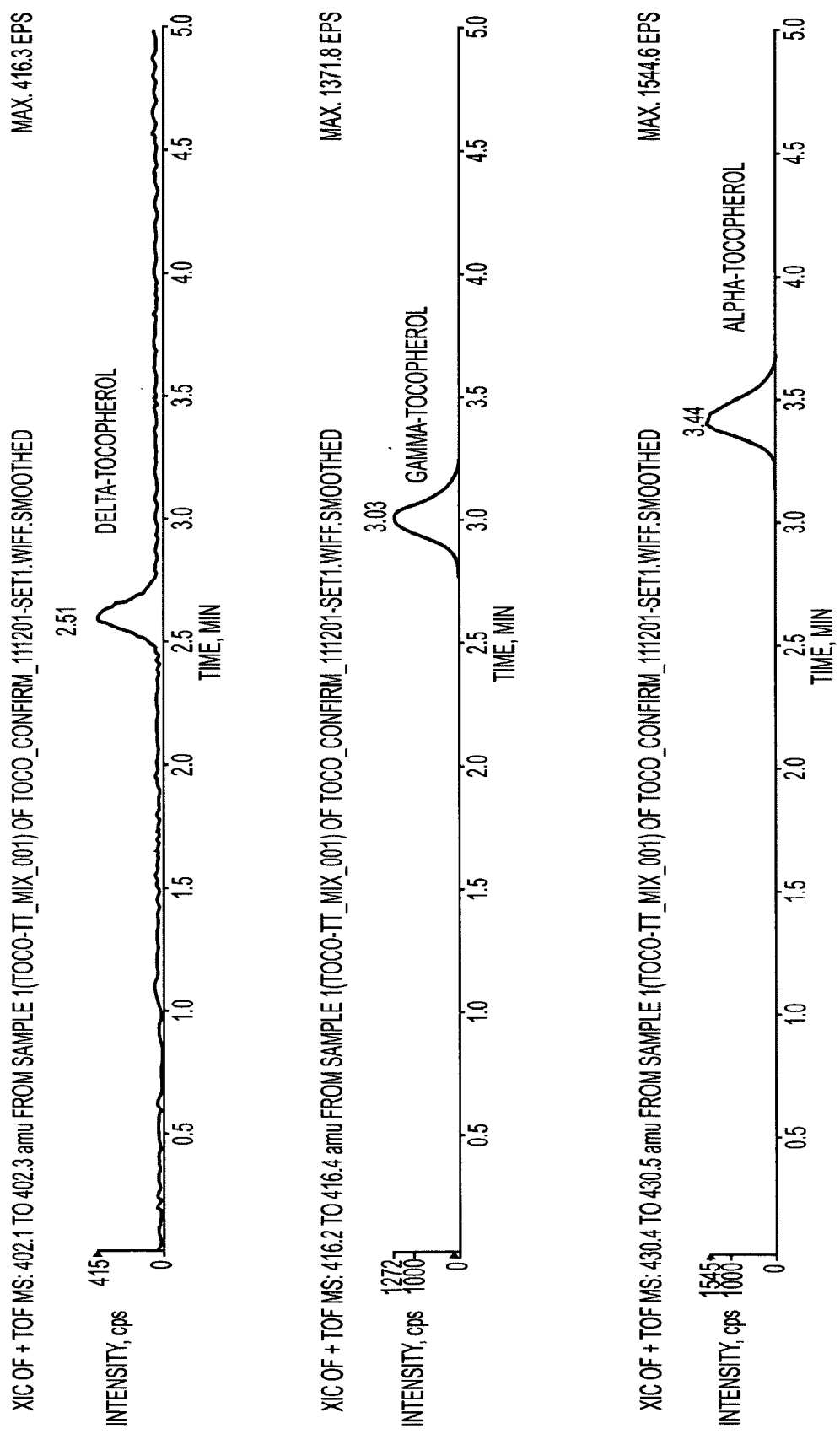
Figure 13A:
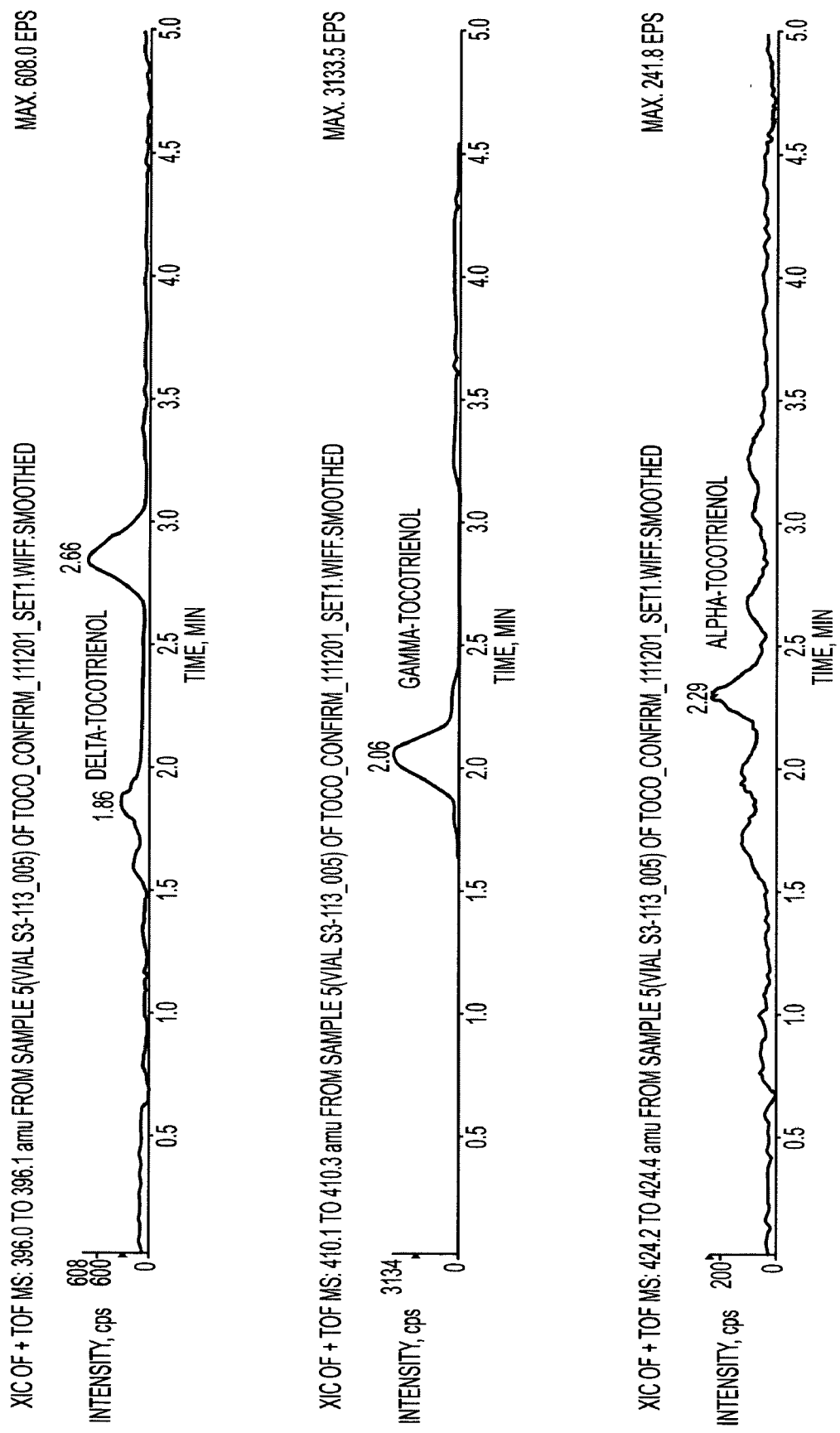
FIG. 13 is an LC/MS graph.
Figure 13B:
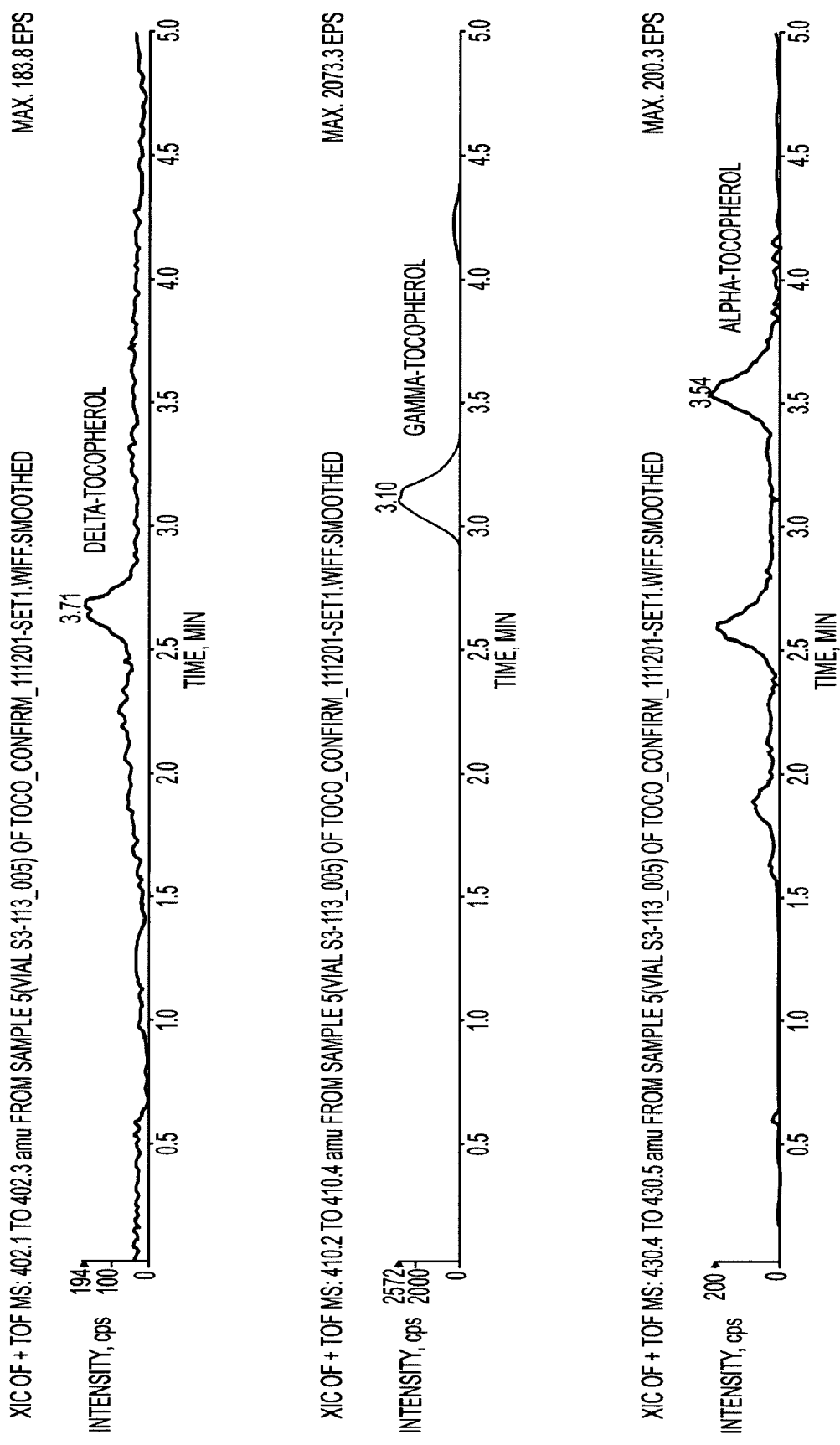
Figure 14:
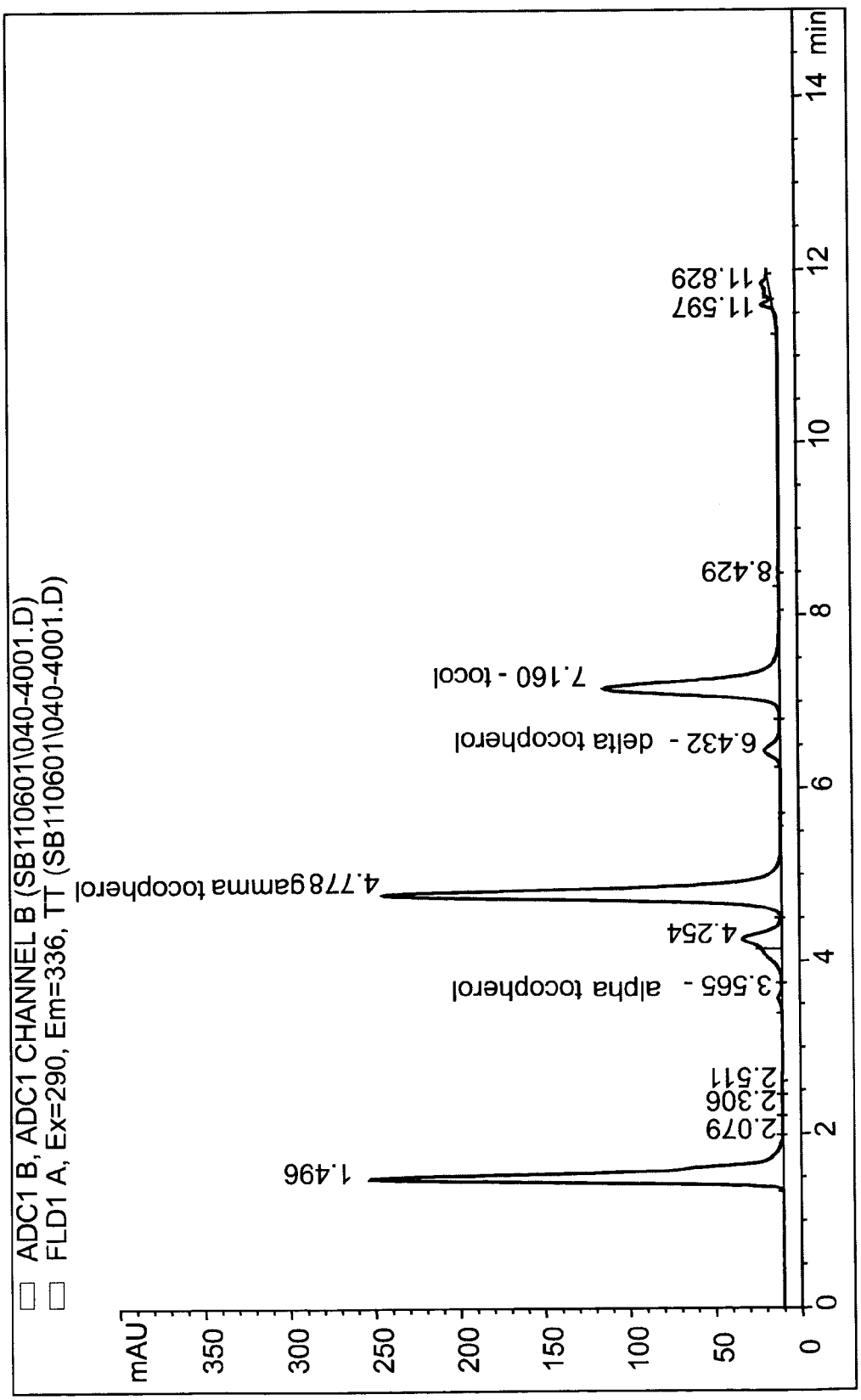
FIG. 14 is an HPLC chromatograph.
Figure 15:
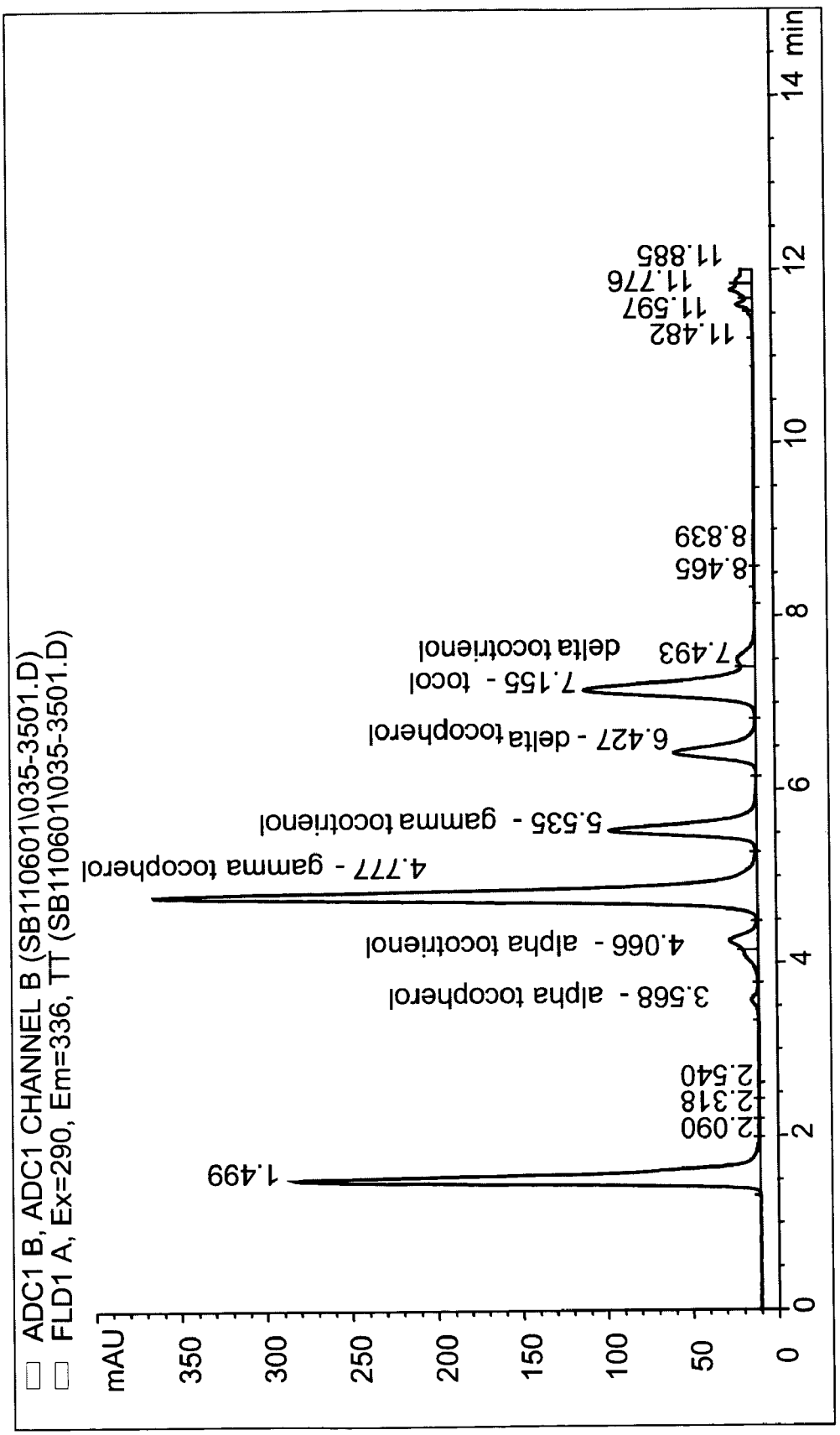
FIG. 15 is an HPLC chromatograph.

Transformed Arabidopsis Plants with AANT1 and Other Tocopherol Biosynthesis Genes Expression constructs pCGN10822, pMON36528, pMON69907 and pMON69909, shown in FIGS. 10–13 respectively, are prepared. *Arabidopsis* plants are transformed with the indicated vectors using the transformation techniques described in Example 8. Transformants are isolated and grown into individual lines by self pollination and seed from each line collected. The total tocopherol and tocotrienol composition of the seeds from each line are analyzed using the method set forth in Example 5. FIG. 10 shows total tocopherol and tocotrienol levels for plant lines harboring the described contructs or a control. An analysis of T2 seeds from plant lines derived by transformation with the vector pMON69909 relative to wild type is shown in FIG. 11. Plant lines transformed with pMON69909 demonstrate a substantial increase in total tocopherols and total tocotrienols, with the largest increases in delta tocopherol, alpha tocotrieneol, delta tocotrienol, and gamma tocotrienol. Some seed from plants harboring the vector pMON69909 show a dark coloration as the result of homogentisic acid accumulation, which is confirmed by LC/MS analysis (see FIGS. 12 and 13).

Heterologous expression of tyrA in seeds of transgenic Arabidopsis plants produces a 1.6-fold increase in seed tocopherol levels as compared to control lines. Another key enzyme essential for tocopherol biosynthesis is HPT, which is involved in the condensation of phytyl pyrophosphate (PPP) and homogentisate (HGA) to produced 2-methyl-6-phytylplastoquinol (2M6PPQ), a precursor for synthesis of four different isoforms of tocopherols. Overexpression of $HPT_{Arabidopisis}$ (ATPT2) and the $HPT_{Synechocystis}$ (slr1736) independently in seeds of transgenic A. thaliana results in a 1.6-fold increase in seed tocopherols. A putative adenylate transporter from A. thaliana (AANT1) expressed as a single gene is shown to increase seed tocopherol levels to 1.4-fold in A. thaliana. To test whether a combination of these genes would result in synergistic effect on tocopherol biosynthesis, various combinations are tested in A. thaliana.

Figure 16:
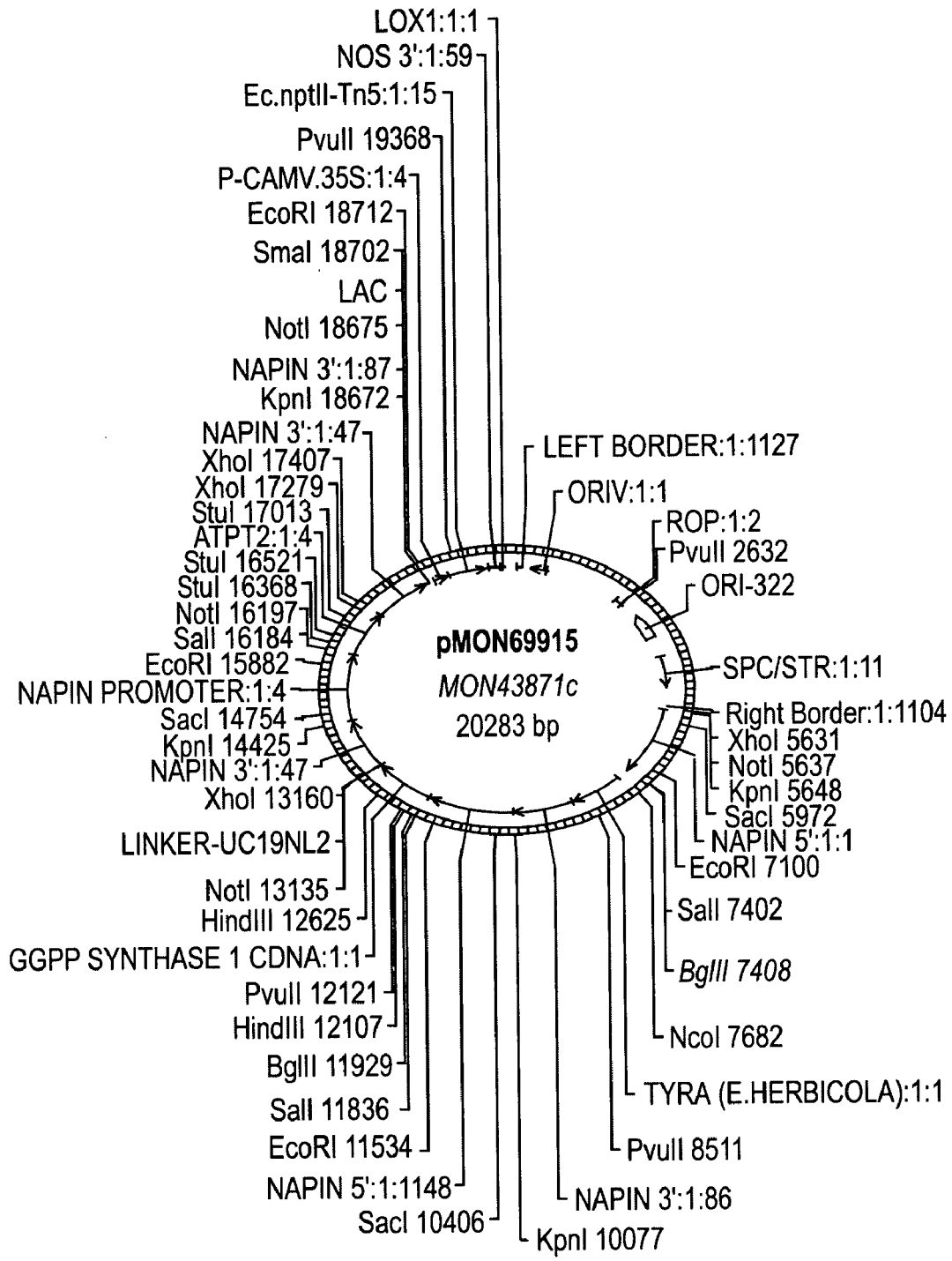
FIG. 16 is a schematic of construct pMON69915.
Figure 17:
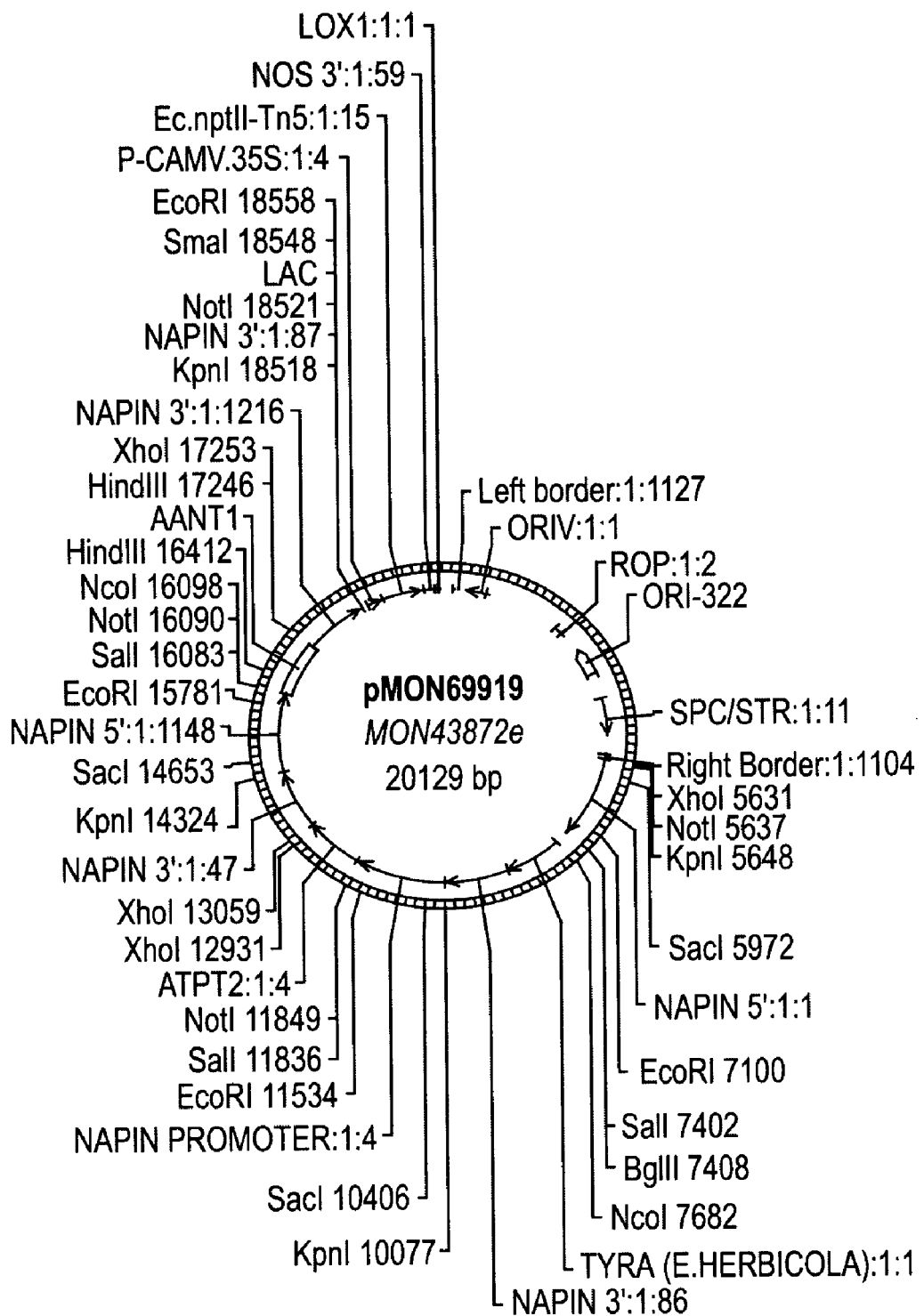
FIG. 17 is a schematic of construct pMON66919.

T2 Arabidopsis seeds harboring A TPT2 and tyrA double gene constructs (pMON69907), ATPT2, tyrA, and HPPD triple gene constructs (pMON69909), ATPT2, tyrA, and GGPPS triple gene constructs (pMON69915 (FIG. 16)), and A TPT2, tyrA, and AANT1 triple gene constructs (pMON69919 (FIG. 17)), are analyzed for seed tocopherol content and composition. Total seed tocopherol and tocotrienol content increases to approximately 2.4-fold in lines transformed with pMON69907 (double gene vector) and up to 5-fold in the lines carrying the triple gene vector (pMON69909) (See FIGS. 10 and 11). HPPD expressed as a single gene in A. thaliana result in a barely detectable increase of tocopherol levels. The combination of HPPD with ATPT2 does not result in a further increase of tocopherol levels as compared to lines harboring ATPT2 alone (data not shown). In contrast, when HPPD is combined with tyrA and ATPT2, tocopherol and tocotrienol levels double compared to the tyrA, ATPT2 combination. Seeds harboring the triple gene construct pMON69909 appear much darker in color than control seeds. Furthermore, it is known that wild-type dicotyledonous plants do not accumulate tocotrienols. However, the transgenic A. thaliana seeds harboring all four constructs accumulates substantial levels of tocotrienols (confirmed by HPLC, and for selected samples by LC-MS, (See FIGS. 12, 13, 14, and 15). The tocopherol and tocotrienol content of seeds harboring the triple gene expression construct, pMON69909, consist of 60% tocotrienols and 40% tocopherols. When the availability of endogenous HGA is elevated by overexpression of the HGA biosynthetic enzymes (tyrA & HPPD) along with HPT, the HPT would utilize geranylgeranyl pyrophosphate (GGPP) and HGA to produce tocotrienols instead of tocopherols under conditions limited by the availability of endogenous level of geranylgeranyl reductase (GGH). The GGH functions on hydrogenating the GGPP to PPP, a substrate for HPT in tocopherol synthesis. Hence, increased tocotrienols accumulation seen in the constructs tested can be overcome by overexpression of GGH in combination with tyrA, HPPD, and HPT.

EXAMPLE 10

Transformed Plants with AANT 1 and Other Tocopherol Biosynthesis Genes

Plants are transformed with the DNA constructs shown in tables 2 and 3 below, employing the techniques described in Example 8. The constructs contain one or more genes under the control of a napin promoter (Kridl et al., Seed Sci. Res. 1:209:219 (1991)), the 7S' promoter (Chen et al., PNAS 83(22):8560–8564 (1998)) or the Arcelin 5 (Arc5) promoter (Goossens et al., Plant Physiol. 120:1095–1104 (1999), and as disclosed in U.S. application Ser. No. 60/255,879, filed on Dec. 18, 2000 and U.S. application Ser. No. 10/015,637, filed on Dec. 17, 2001 both of which are herein incorporated by reference in their entirety)). The products of the genes can be targeted to the plastid by an encoded plastid target peptide such as CTP1 (Keegstra, Cell 56(2):247–53 (1989); Nawrath, al., Proc. Natl. Acad. Sci. U.S.A. 91:12760–12764 (1994)) or CTP2. One or more of the following genes are used: an E. herbicola tyrA gene (Xia et al., J. Gen. Microbiol. 138:1309–1316 (1992)), an slr1736 gene (in Cyanobase on the world wide web at: kazusa.org.jp/cyanobase), an ATPT2 gene (Smith et al., Plant J. II.: 83–92 (1997)), an E. coli dxs gene (Lois et al., Proc. Natl. Acad. Sci. U.S.A. 95 (5).2105–2110 (1998)), a dxr gene (Takahashi et al. Proc. Natl. Acad. Sci. U.S.A. 95 (17), 9879–9884 (1998)), an HPPD gene (Norris et al., Plant Physiol. 117:1317–1323 (1998)), a GGH gene (Keller et al., Eur. J. Biochem. 251: 413–417 (1998)), an Arabidopsis thaliana GGPPS gene (Bartley and Scolnik, Plant Physiol. 104:1469–1470 (1994)), an AANT1 gene (Saint Guily, et al., Plant Physiol., 100(2):1069–1071 (1992)), an MT1 gene (as above for Example 8), a TMT2 gene (as above for example 8), a GMT gene (as above for example 8, and WO 00/32757, WO 00/10380), an slr1737 gene (in Cyanobase on the world wide web at kazusa.org.jp/cyanobase), and an antisense construct for homogentisic acid dioxygenase (denoted $HGD_{AS}$)(Sato et al., J. DNA Res. 7 (1):31–63 (2000)). Each construct is transformed into at least one canola, Brassica napus, Arabidposis, and soybean plant. The tocopherol composition and level in each plant is also analyzed using the method set forth in example 5. Examples of transformed plants with tyrA and other tocopherol biosynthesis genes include Arabidopsis plants transformed with the constructs set forth in Table 2 and soy plants transformed with the constructs in Table 3.

Plants with desired characteristics are subject to further crosses to generate transgenic plants having one or more of the following combination of introduced genes: tyra, slr1736, ATPT2, dxs, dxr, GGH, GGPPS, HPPD, MT1, TMT2, GMT, AANT1, slr 1737, and an antisense construct for homogentisic acid dioxygenase. Alternatively the plants are crossed to stack multiple copies of one or more of the aforementioned genes in a transgenic plant.

TABLE 2

The following gene combinations are prepared and tested in *Arabidopsis thaliana*

1. pNapin::CTP1::TyrA$_{E.\ herbicola}$::Napin 3'/pNapin::CTP2::HPPD$_{A.\ thaliana}$::Napin3'/pNapin::ATPT2$_{A\ thaliana}$::Napin 3'
2. pNapin::CTP1::TyrA$_{E.\ herbicola}$::Napin 3'/pNapin::AANT1$_{A\ thaliana}$::Napin 3'/pNapin::ATPT2$_{A\ thaliana}$::Napin 3'
3. pNapin::CTP1::TyrA$_{E.\ herbicola}$::Napin 3'/pNapin::GGPPS$_{A.\ thaliana}$::Napin 3'/pNapin::ATPT2$_{A\ thaliana}$::Napin 3'
4. pNapin::CTP1::TyrA$_{E.\ herbicola}$::Napin 3'/pNapin::CTP1::DXS$_{E.\ coli}$::Napin 3'/pNapin::ATPT2$_{A\ thaliana}$::Napin 3'/pNapin::GGH::Napin 3'
5. pNapin::CTP1::TyrA$_{E.\ herbicola}$::Napin 3'/pNapin::CTP1::DXR$_{E.\ coli}$::Napin 3'/pNapin::ATPT2$_{A\ thaliana}$::Napin 3'/pNapin::GGH::Napin 3'
6. pNapin::CTP1::TyrA$_{E.\ herbicola}$::Napin 3'/pNapin::HGD$_{AS}$::Napin 3'
7. pNapin::CTP1::TyrA$_{E\ herbicola}$::Napin 3'/pNapin::HGD$_{AS}$::Napin 3'/pNapin::ATPT2$_{A\ thaliana}$
8. pNapin::CTP1::TyrA$_{E\ herbicola}$::Napin 3'/pNapin::HGD$_{AS}$::Napin 3'/pNapin::ATPT2$_{A\ thaliana}$::Napin 3'/pNapin::GGH::Napin 3'
9. pNapin::CTP1::TyrA$_{E.\ herbicola}$::Napin 3'/pNapin::HGD$_{AS}$::Napin 3'/pNapin::ATPT2$_{A\ thaliana}$::Napin 3'/pNapin::CTP1::DXS$_{E\ coli}$::Napin 3'/pNapin::GGH::Napin 3'

TABLE 3

The following gene combinations are prepared and tested in *Glycine max*

1. p7S::CTP2::HPPD::E9 3'/p7S '::CTP1::TyrA::E9 3'
2. pArc5::ATPT2::Arc 3'/p7S '::CTP1::TyrA::E9 3'/pNapin::GGH::Napin 3'
3. pArc5::ATPT2::Arc 3'/p7S::CTP1::TyrA::E9 3'/pNapin::GGH::Napin 3'/pNapin::CTP1::DXS::Napin 3'

EXAMPLE 11

Construction of Vectors Encoding Multiple Enzymes

This example set forth the use of a prephenate dehydrogenase (tyrA), such as the *Erwinia herbicola* tyrA, in combination with other enzymes in the tocopherol biosynthetic pathway to enhance tocopherol production in transgenic plant seeds, such as *Arabidopsis thaliana* seeds. The enzymes combined with tyrA include ATPT2, p-hydroxyphenylpyruvate dioxygenase (HPPD$_{Arabidopsis}$), and geranylgeranylpyrophosphate synthase (GGPPS$_{Arabidopsis}$) from *Arabiclopsis thaliana*. In addition tyrA is also tested in combination with ATPT2 and an adenylate transporter (AANT1$_{Arabidopsis}$) from *Arabidopsis thaliana*.

Figure 8:
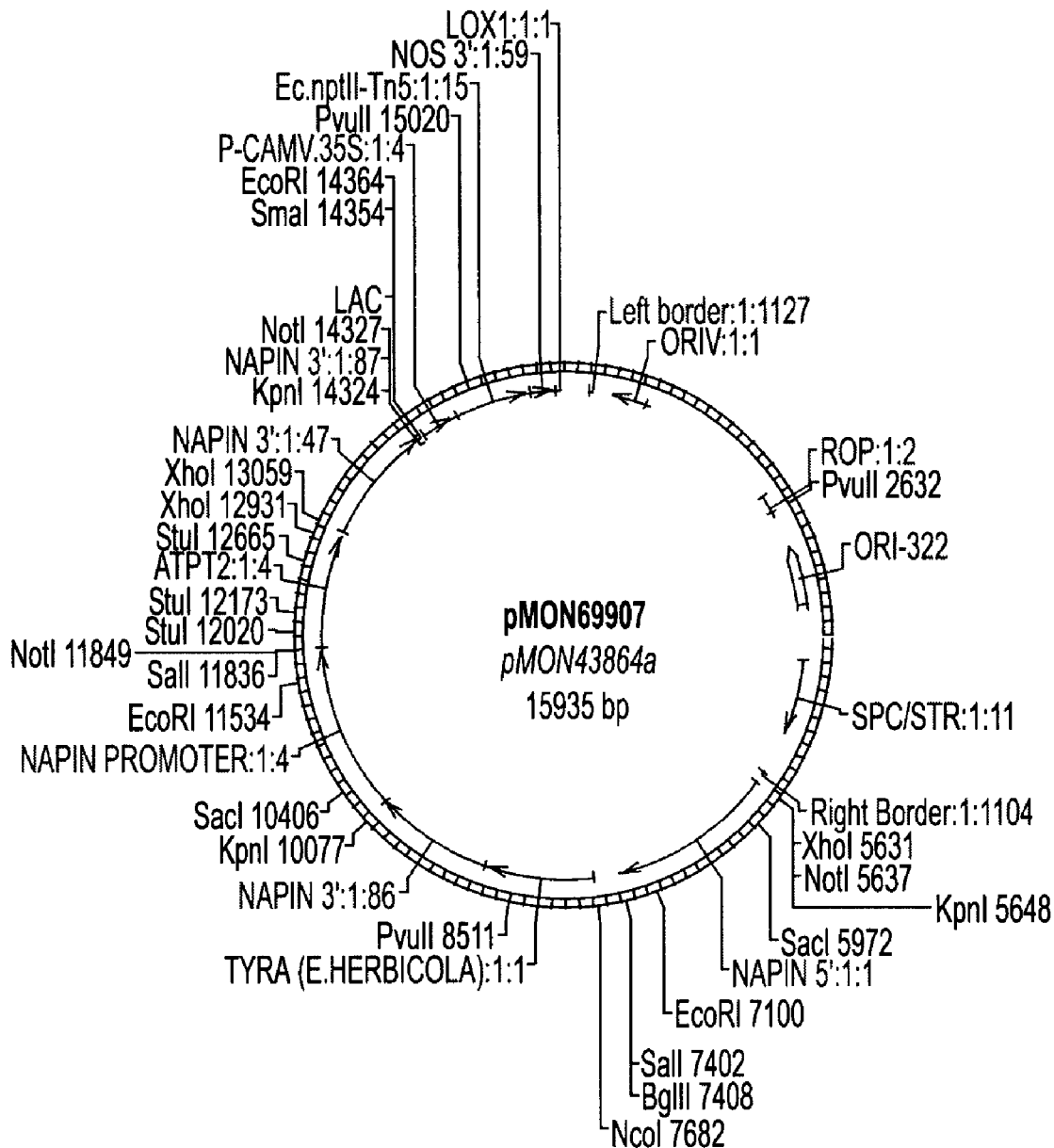
FIG. 8 is a schematic of construct pMON69907.
Figure 9:
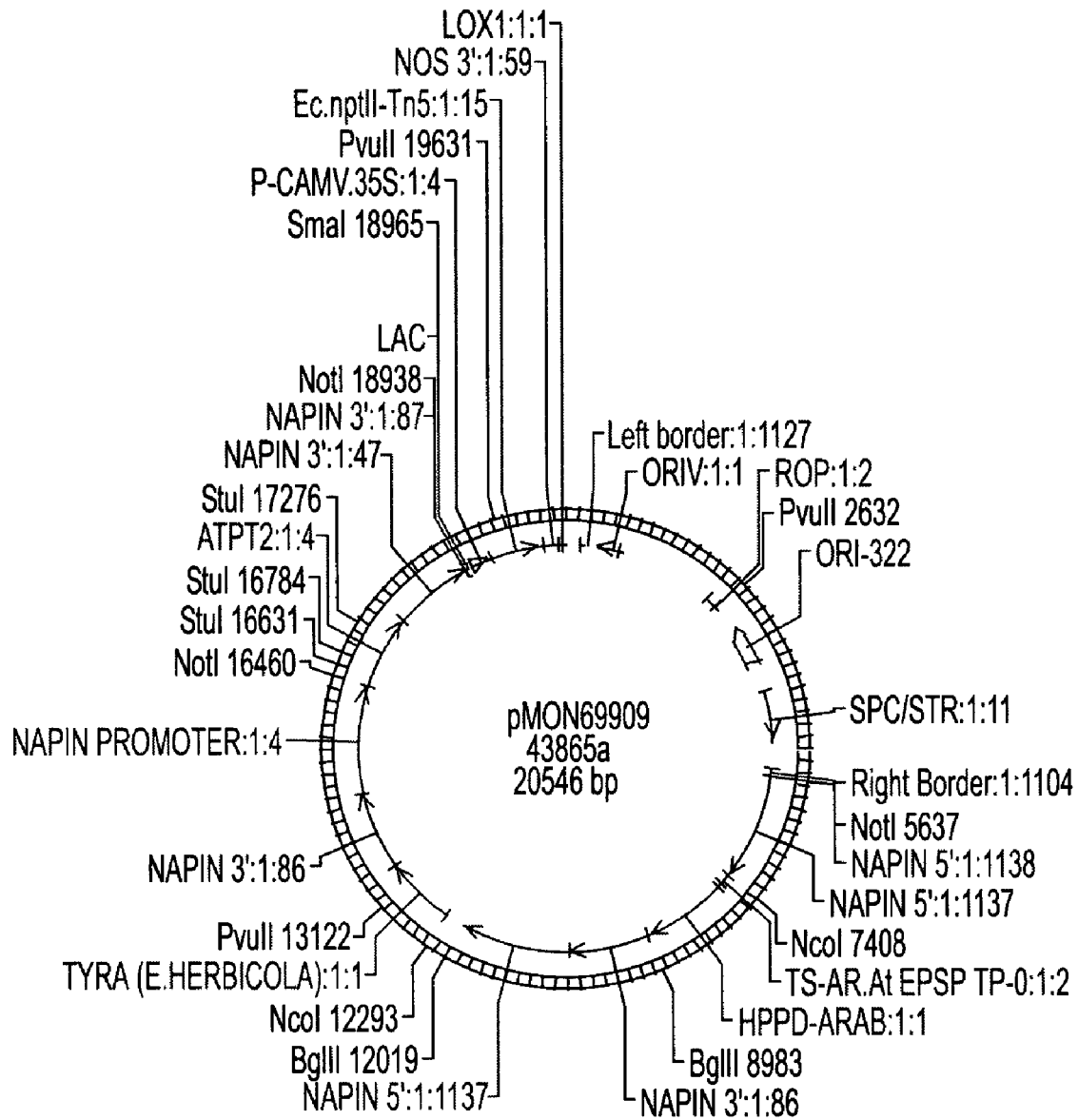
FIG. 9 is a schematic of construct pMON69909.
Figure 18:
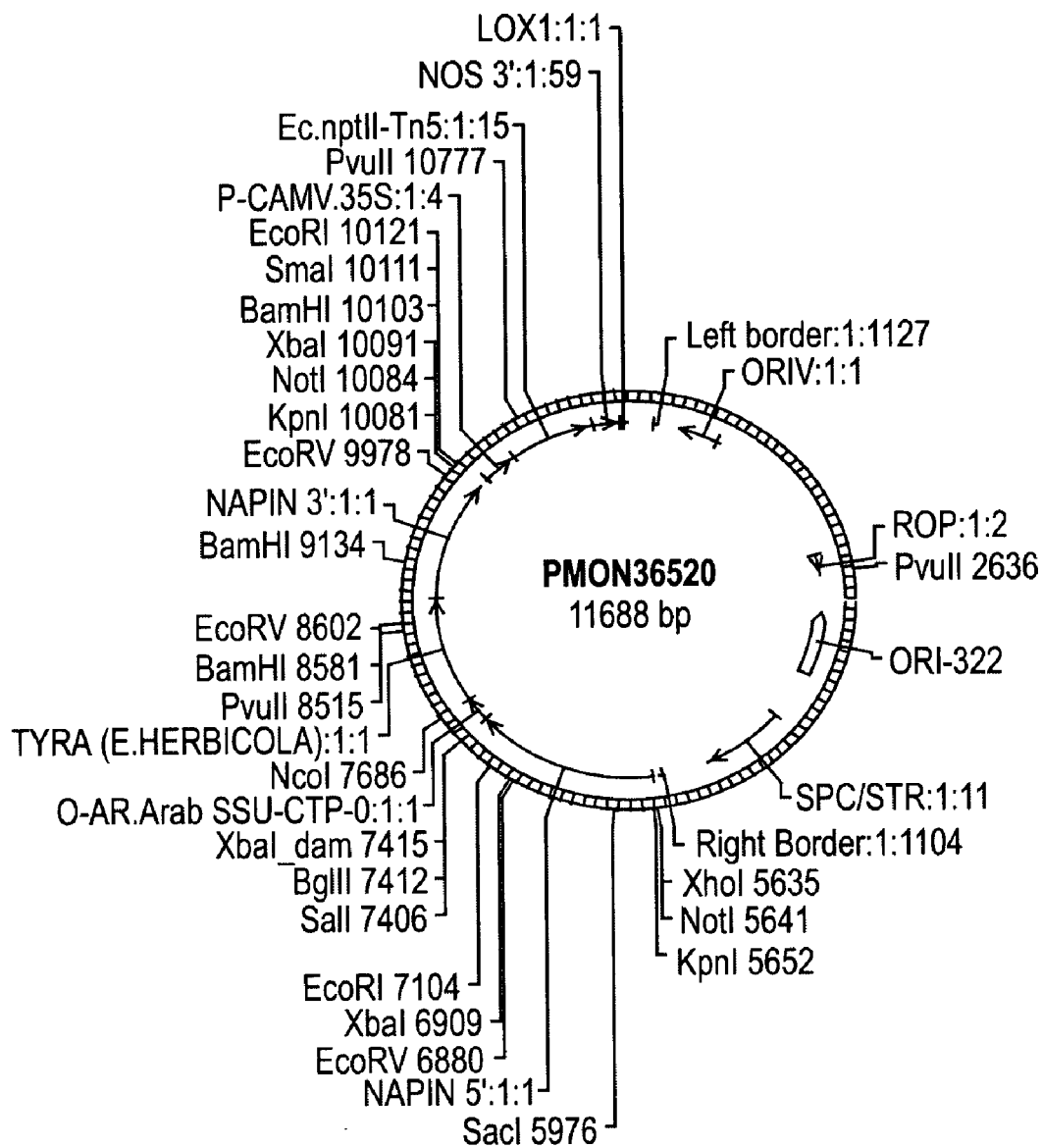
FIG. 18 is a schematic of construct pMON36520.
Figure 19:
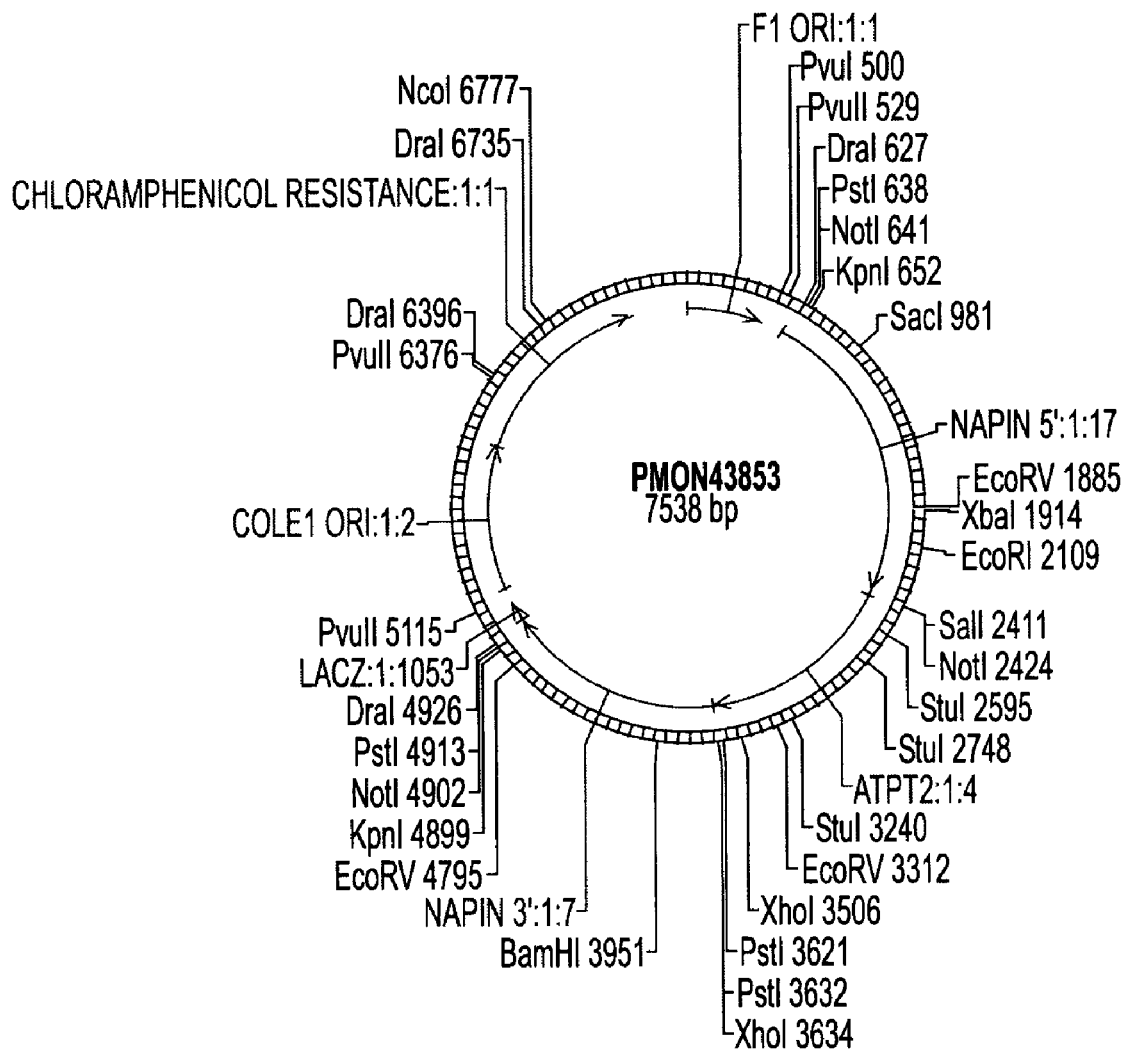
FIG. 19 is a schematic of construct pMON43853.

Construction of a double gene vector harboring seed specific tyrA and ATPT2 expression cassettes is performed as follows. Purified plasmid DNA of pMON36520 (FIG. 18) is subjected to a partial KpnI digest and ligated with a 4.2 kbp gel purified Kpn I-fragment isolated from pMON43853 (FIG. 19). The 4.2 kb insert from pMON43853 contains the PPT gene expression cassette (pNapin::ATPT2::Napin 3'). The resulting plant binary vector pMON69907 (FIG. 8) is used for transformation of *Arabidopsis thaliana* to test the combinatorial effect of seed specific expression of tyrA and ATPT2.

Figure 20:
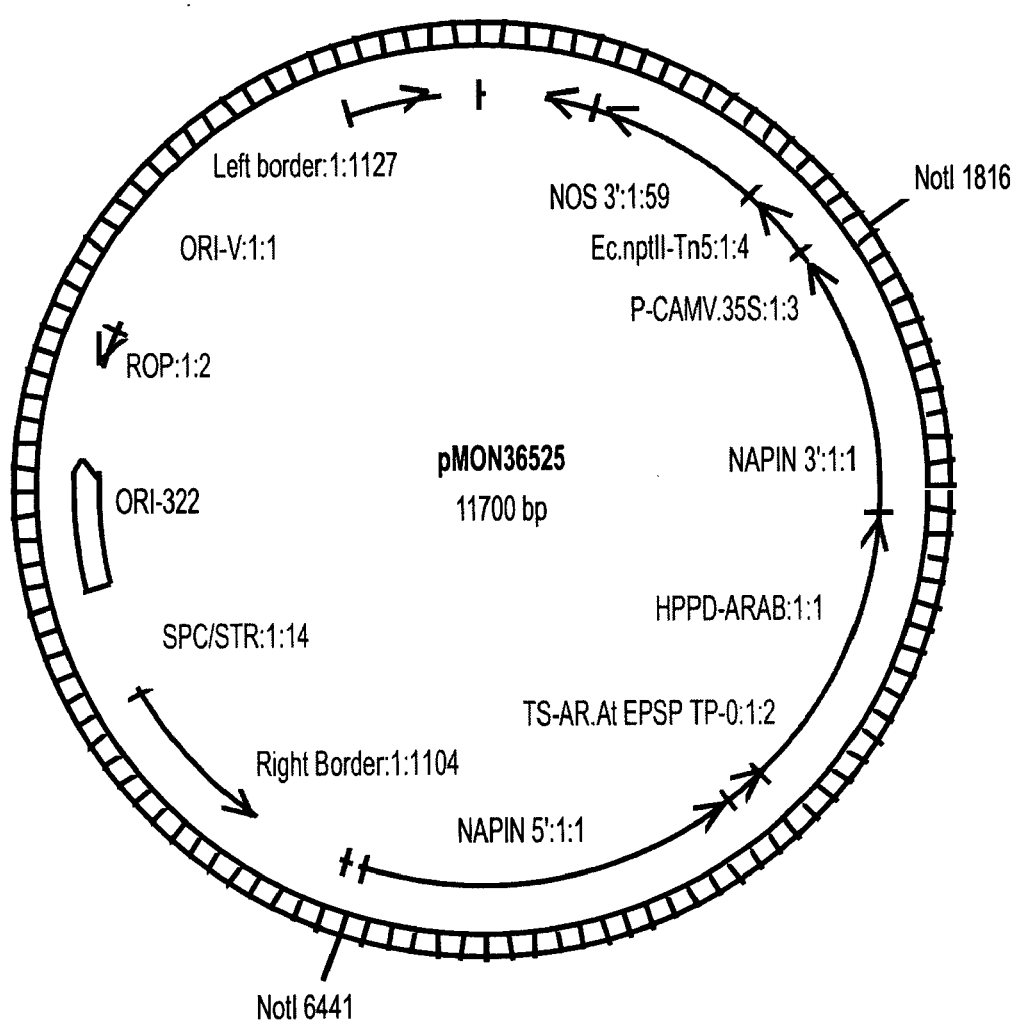
FIG. 20 is a schematic of construct pMON36525.

To further increase tocopherol biosyntheses, the HPPD$_{Arabidopsis}$ is expressed in addition to tyrA, and ATPT2 in *Arabidopsis thaliana* seed. This is achieved by adding a seed specific expression cassette for HPPD$_{Arabidopsis}$ to pMON69907 resulting in the formation of pMON69909. The binary vector pMON69909 is constructed by partially digesting pMON69907 with KpnI. The single KpnI-cut pMON69907 is gel purified and ligated with a 4.6 kb KpnI/KpnI insert isolated from pMON36525 (FIG. 20). The 4.6 kb KpnI/KpnI insert from pMON36525 contains the HPPD gene expression cassette, pNapin::CTP2::HPPD$_{Arabidopsis}$::Napin 3' to direct seed specific plastid targeted expression of HPPD. The CTP2 is a chloroplast-target signal from the *Arabidopsis* 5-enolpyruvylshikimate-3-phosphate synthase (EPSPS) gene.

Figure 21:
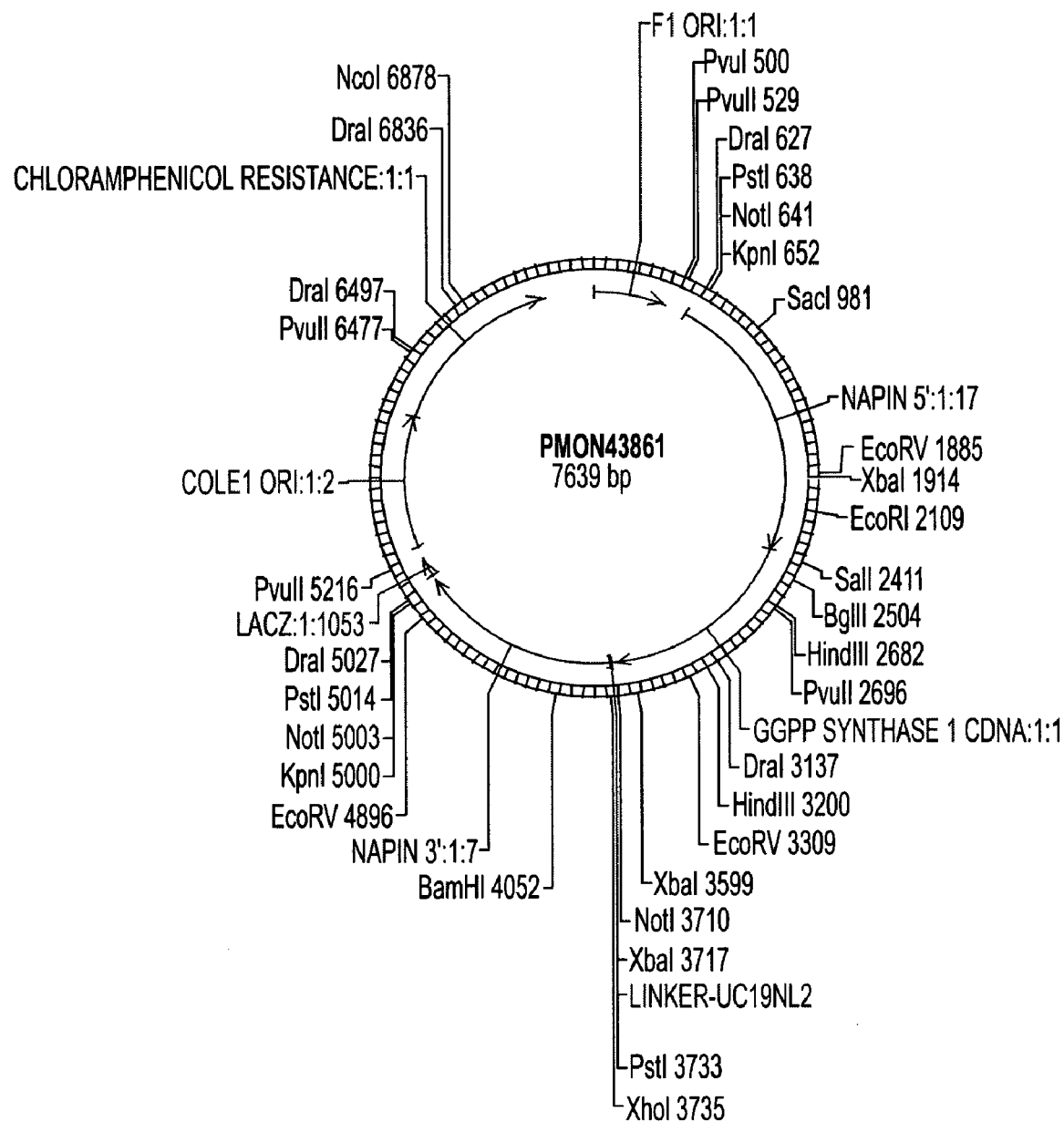
FIG. 21 is a schematic of construct pMON43861.
Figure 22:
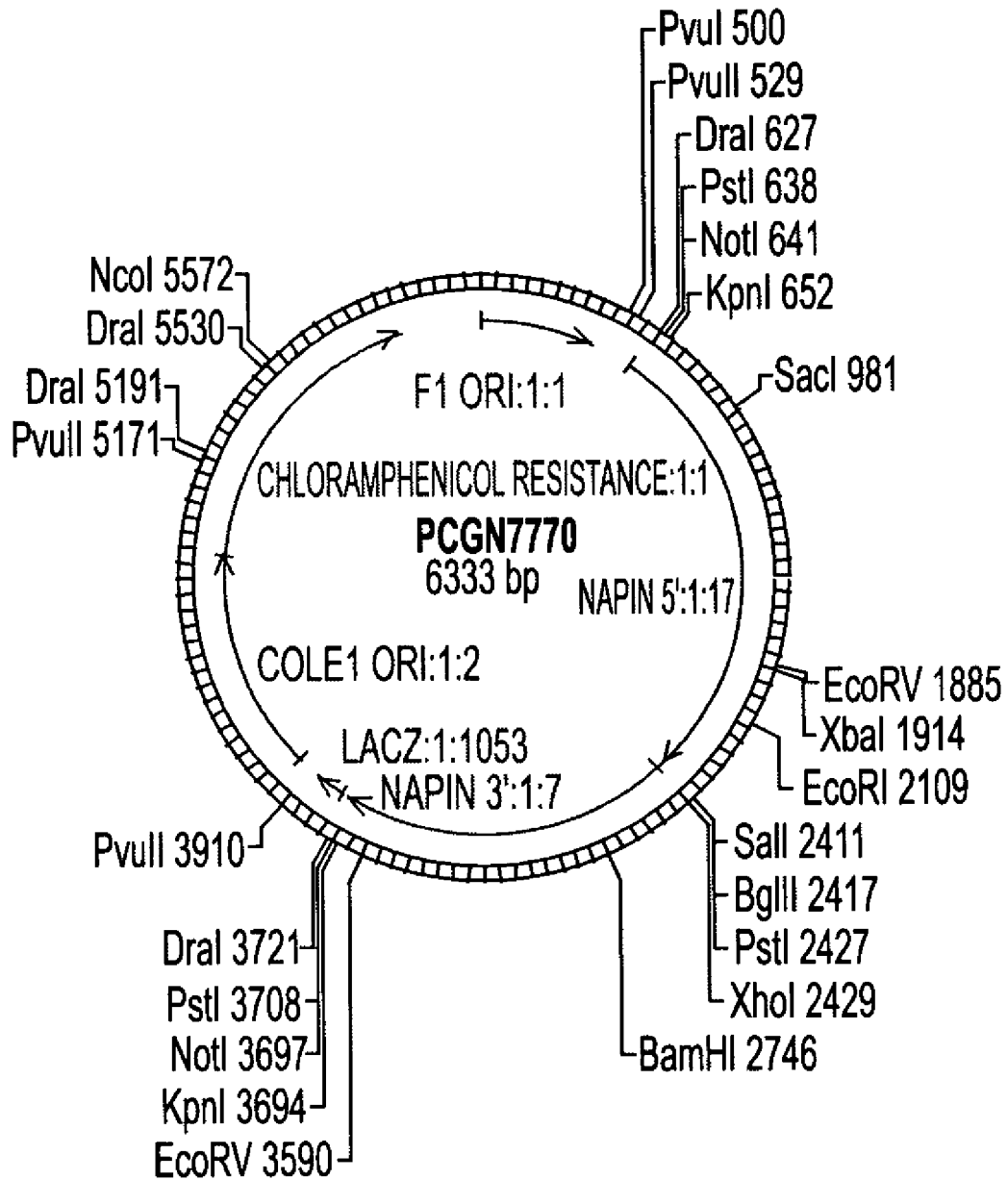
FIG. 22 is a schematic of construct pCGN7770.

The binary vector pMON69915 (FIG. 16) is constructed to test the effect of three gene combinations, tyrA, ATPT2, and GGPPS$_{Arabidopsis}$ on seed tocopherol production. Vector pMON69907 is digested partially with KpnI. Single KpnI-cut pMON69907 is gel purified and ligated with a gel purified 4.3 kb, KpnI/KpnI fragment from pMON43861 (FIG. 21) to create pMON69915. The KpnI fragment from pMON43861 contains the gene expression cassette for the *Arabidopsis* geranylgeranyldiphosphate synthase from *Arabidopsis thaliana* (pNapin::GGPPS$_{Arabidopsis}$::Napin 3'). The GGPPS cDNA is identified as an EST clone by searching an EST database with sequence information available in the literature (Okada et al., *Plant Physiol.* 122:1045–1056 (2000)). The EST clone is digested with NcoI and blunt-ended by filling the 5' overhang with the Klenow-fragment. Subsequently the clone is digested with BamHI and to excise the cDNA fragment. The gel purified BamHI/blunt cDNA fragment is ligated with BglII/SalI digested and (SalI blunt-ended) vector pCGN7770 (FIG. 22) to create pMON43861.

Figure 23:
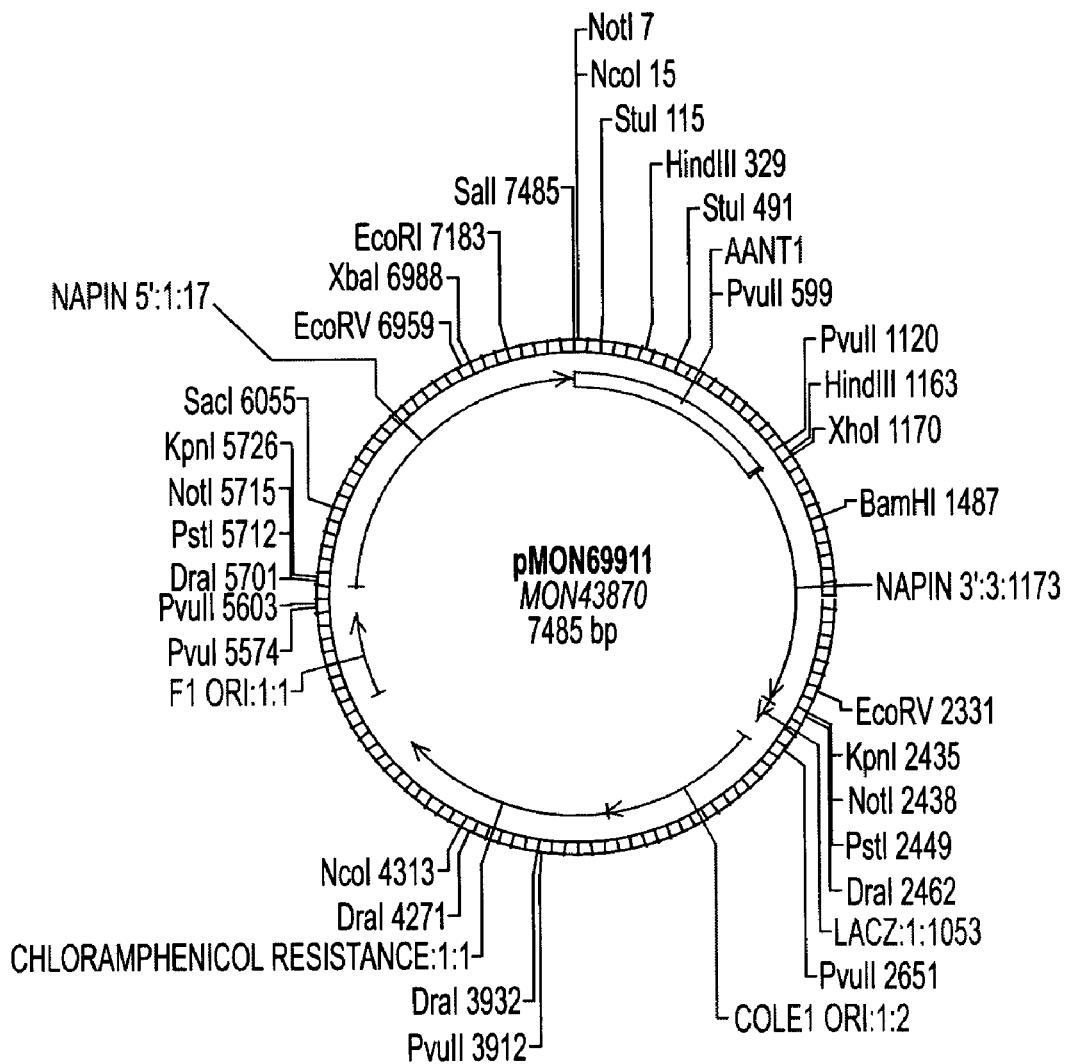
FIG. 23 is a schematic of construct pMON69911.
Figure 24:
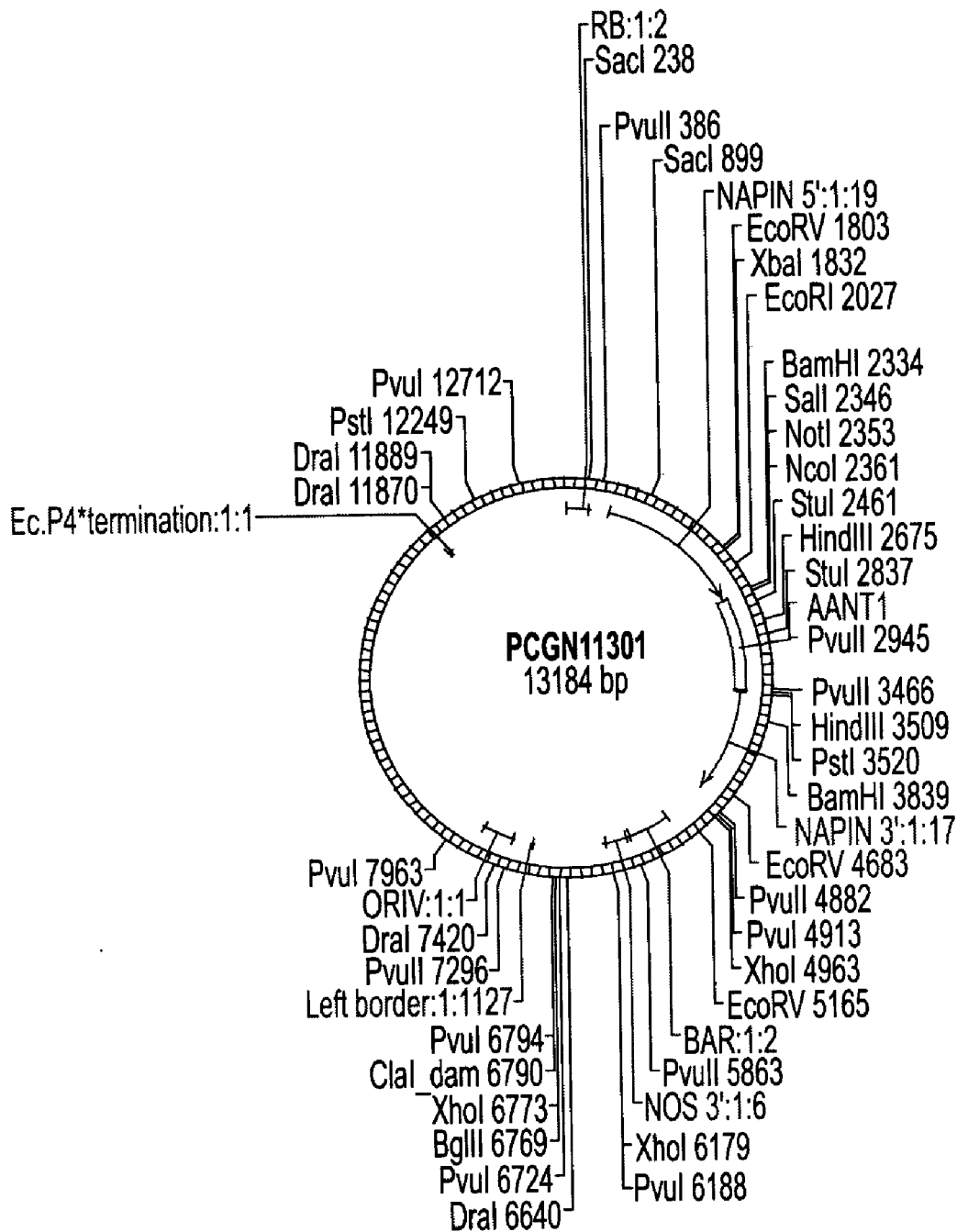
FIG. 24 is a schematic of construct pCGN11301.
Figure 25:
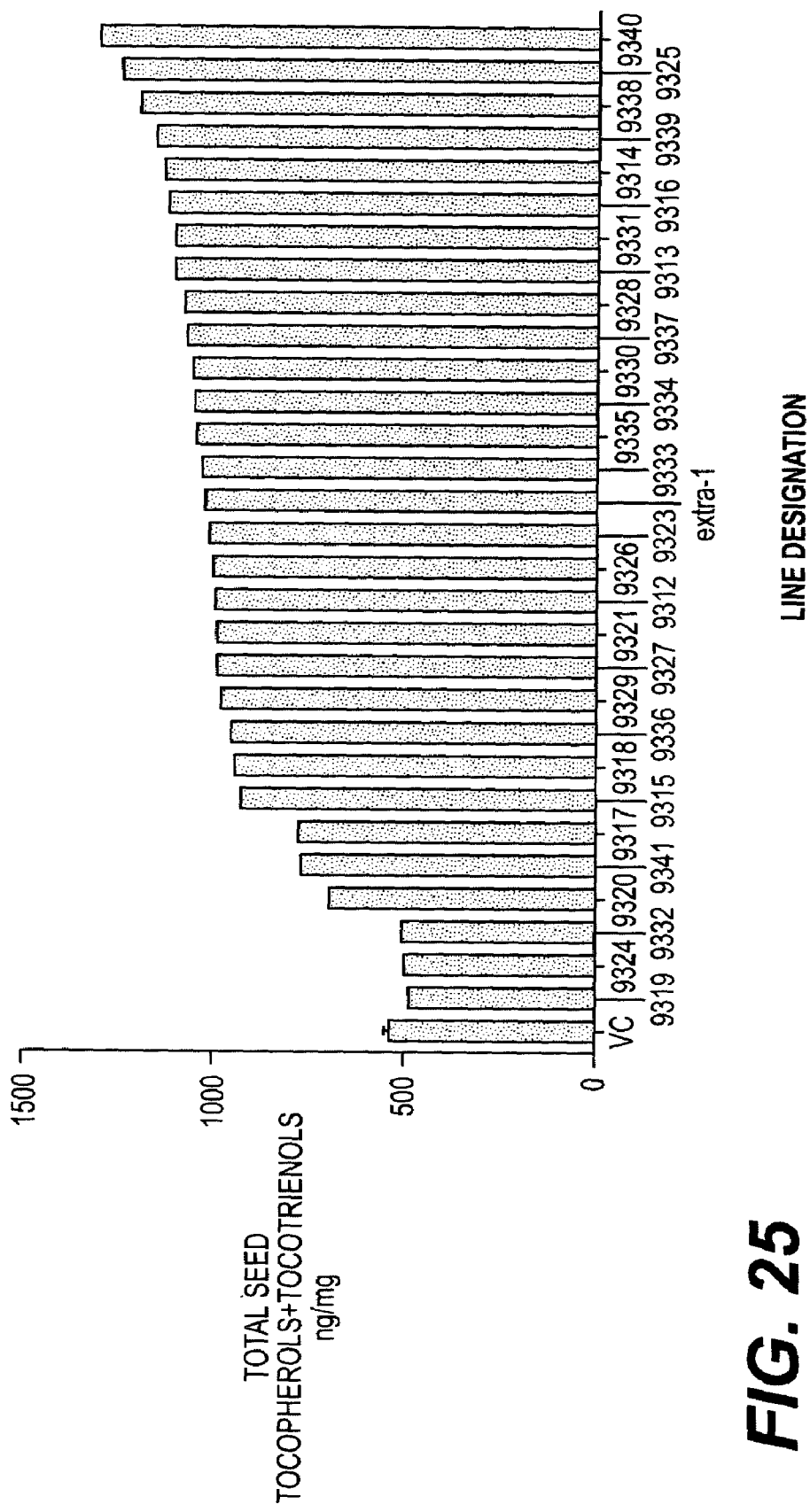
FIG. 25 depicts the total tocopherol and tocotrienol content of *Arabidopsis* seeds from wild type plants and several plant lines transformed with the plasmid vector pMON69907.
Figure 26:
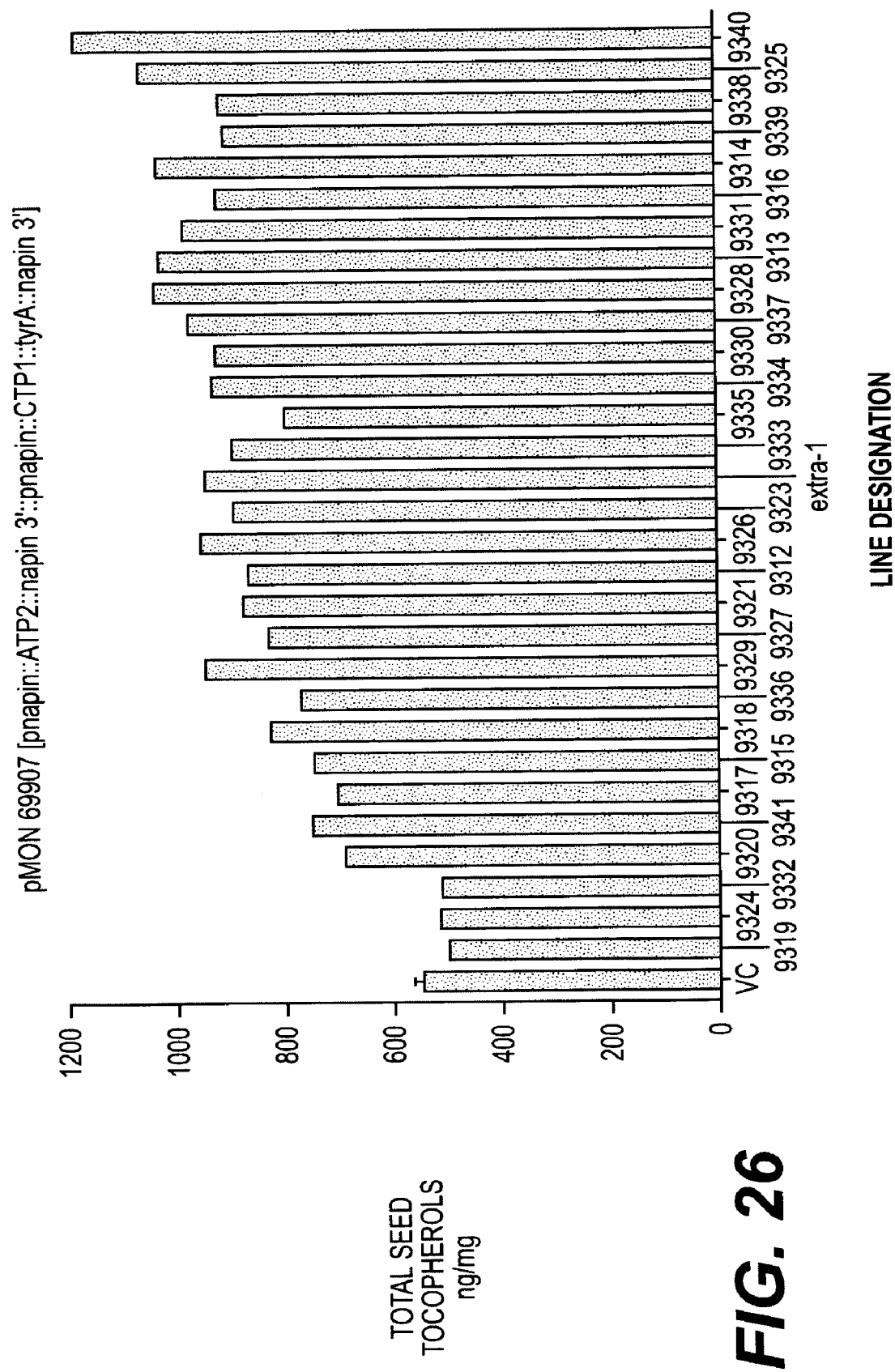
FIG. 26 depicts the total tocopherol content of *Arabidopsis* seeds from wild type plants and several plant lines transformed with the plasmid vector pMON69907.

The plant binary vector pMON69919 (FIG. 17) is constructed to test combined expression of tyrA, ATPT2, and AANT1$_{Arabidopsis}$ on seed tocopherol levels. To generate this vector, pMON69907 is partially digested with KpnI. Single KpnI-cut pMON69907 is gel purified, and ligated with a 4.2 kb gel-purified KpnI/KpnI fragment from pMON69911 (FIG. 23). The 4.2 kb fragment contains a seed specific expression cassette for the *Arabidopsis* adenylate transporter AANT1 (pNapin::AANT1$_{Arabidopsis}$::napin 3'). pMON69911 is generated by excising the AANT1 fragment from pCGN11301 (FIG. 24) with SalI and PstI (the PstI site is blunted by removing 3' overhang with Klenow) and then ligated to SalI/XhoI digested (XhoI blunt-ended) pCGN7770.

Using the published partial sequence of AANT1 (Saint-Guily et al., *Plant Physiol.* 100(2):1069–1071 (1992)) several full-length clones are identified in EST databases. The AANT1 coding region is PCR-amplified using primers, AANT1F 5'-GGATCCGCGGCCGCACCATGGTTGATCA AGTTCAGCA (SEQ ID NO: 11) and AANT1R 5'-GAGCT CCTGCAGGAAGCTTTTAGGCACCTCCTGATCCGT-3'

(SEQ ID NO: 12). The NotI site (underlined) is placed upstream of the start codon (italics) in primer AANT1F while the Sse8387I site (underlined) is placed downstream of the stop codon (italics) in AANT1R. The PCR products are first cloned into pCR2.1 and the inserts are verified by sequencing of both strands. Subsequently, the NotI/Sse8387I fragments are inserted into the NotI/Sse8387I sites of the napin expression cassette in pCGN9979 in sense orientation with respect to the napin promoter to generate pCGN11301. The plant expression constructs are used for transformation of *Arabidopsis thaliana* by *Agrobacterium* mediated transformation as described in above.

EXAMPLE 12

Expression of Vectors Encoding Multiple Enzymes in Plants

Figure 27:
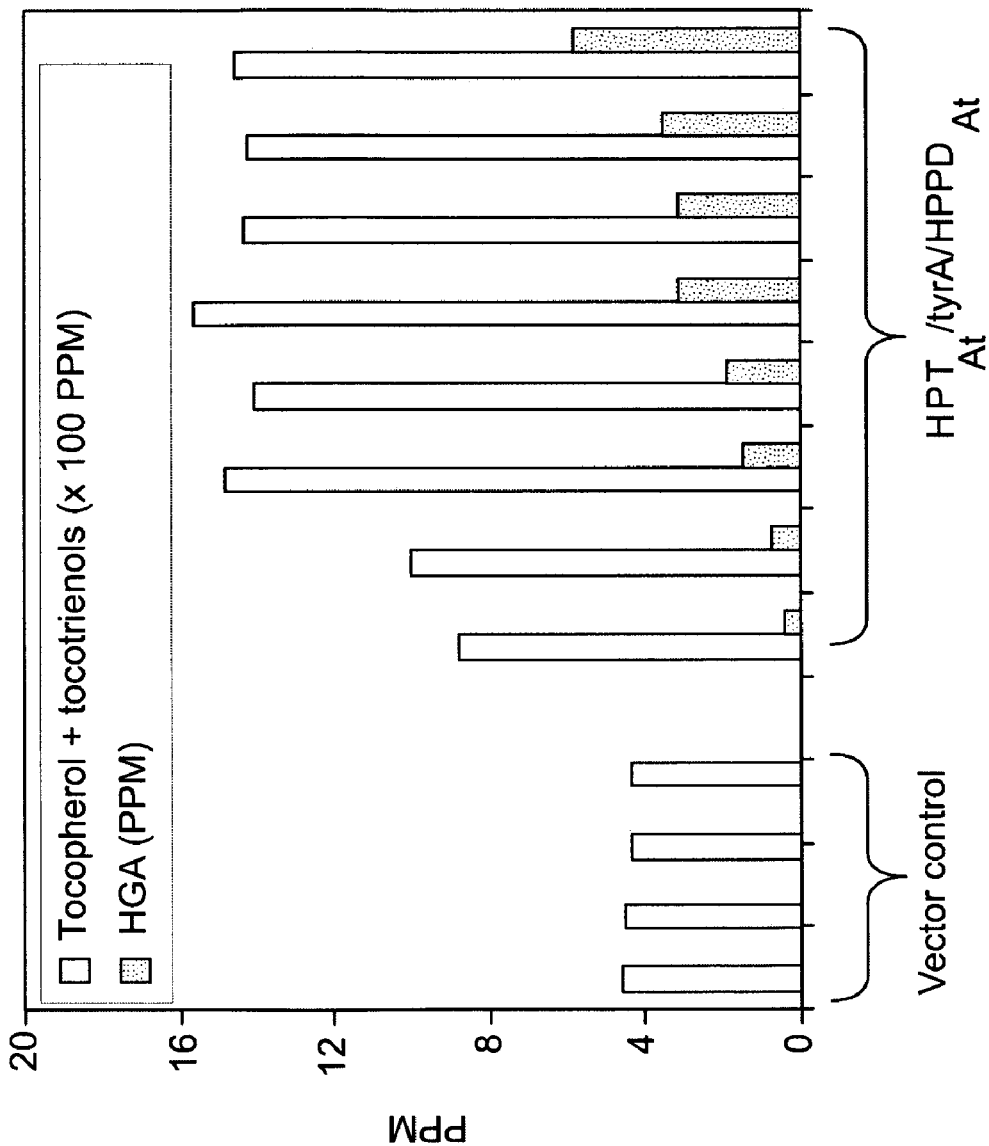
FIG. 27 shows tocopherol and tocotrienol as well as HGA levels in selected lines.
Figure 28:
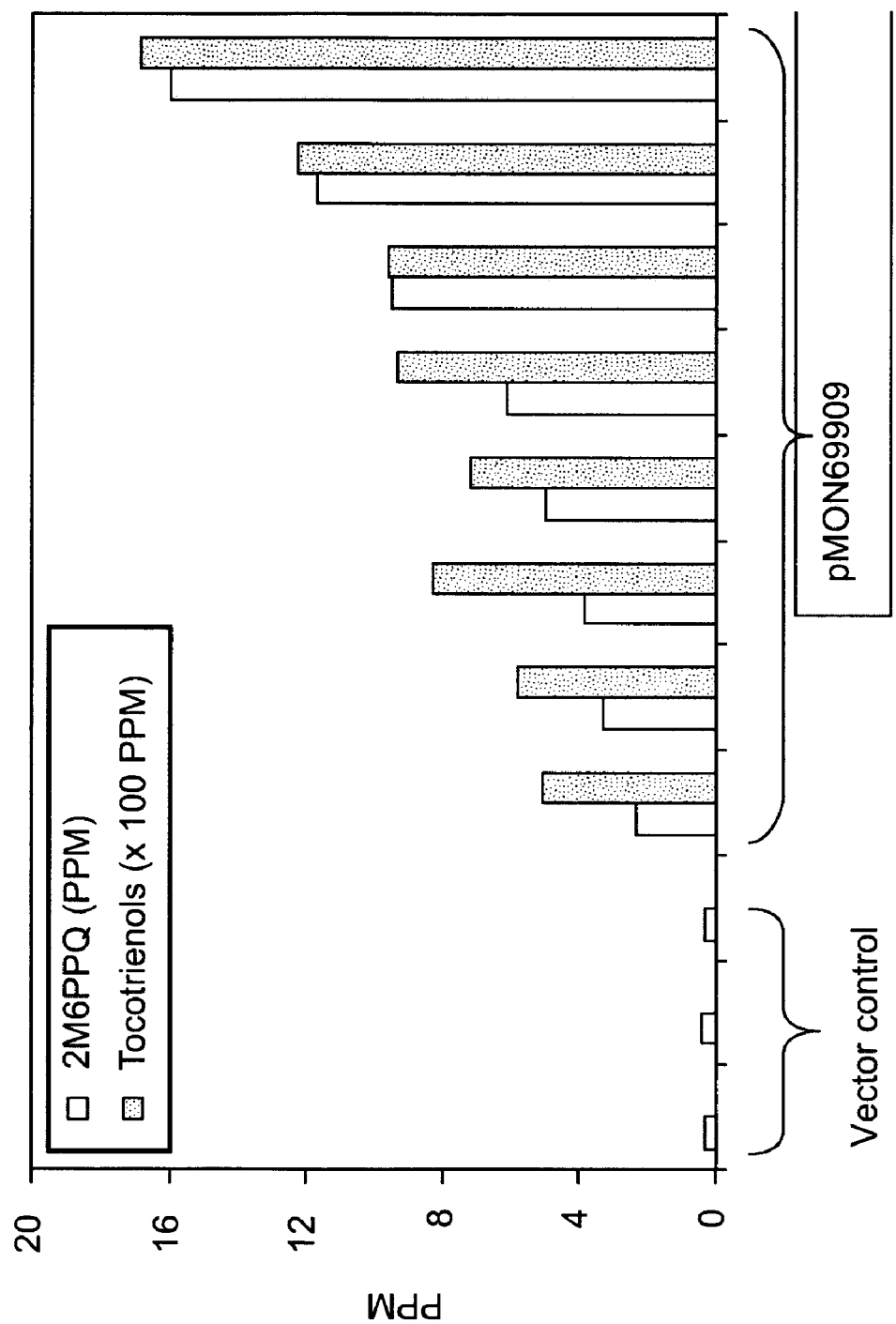
FIG. 28 shows tocotrienol and 2M6PPQ levels in selected lines.

Using the transformation technique given in Example 8, *Arabidopsis thaliana* plants are transformed with the vectors from Example 11. Results for pMON69909 are given in FIGS. 25, 26, 10–15. Further results are given in Table 4, and in FIGS. 27 and 28, which show tocopherol, tocotrienol, homogentisate, and 2-methylphytlyplastoquinol levels for transformed plants having pMON69909.

TABLE 4

| Construct | Genetic elements | Tocopherol/Tocotrienol increase | % tocopherol | % tocotrienol |
|---|---|---|---|---|
| pMON69907 | pNapin::HPT$_{Arabidopsis}$ napin 3'/pNapin::CTP1::tyrA$_{Erwinia\ herbicola}$::napin 3' | 2.4-fold | 91 | 9 |
| pMON69909 | pNapin::HPT$_{Arabidopsis}$::napin 3'/pNapin::CTP1::tyrA$_{Erwinia\ herbicola}$::napin 3'/pNapin::CTP2::HPPD$_{Arabidopsis}$::napin 3' | 5-fold | 38 | 62 |
| pMON69915 | pNapin::HPT$_{Arabidopsis}$::napin 3'/pNapin::CTP1::tyrA$_{E.\ herbicola}$::napin 3'/pNapin::GGPPS$_{Arabidopsis}$::napin 3' | 2.9-fold | 86 | 14 |
| pMON69919 | pNapin::HPT$_{Arabidopsis}$::napin 3'/pNapin::CTP1::tyrA$_{E.\ herbicola}$::napin 3'/pNapin::AANT1$_{Arabidopsis}$::napin 3' | 3-fold | 89 | 11 |

What is claimed is:

1. A substantially purified nucleic acid molecule that encodes an adenylate transporter, wherein said nucleic acid molecule is selected from the group consisting of:
   (a) a nucleic acid sequence encoding the polypeptide sequence of SEQ ID NO:2;
   (b) a nucleic acid sequence comprising the AANT1 coding region of the nucleic acid sequence of SEQ ID NO:1 or the complement thereof;
   (c) a nucleic acid sequence that hybridizes to the AANT1 coding region of the nucleic acid sequence of SEQ ID NO:1 or the complement thereof under high stringency conditions of 0.2×SSC and 65° C.; and
   (d) a nucleic acid sequence having at least 90% sequence identity to the AANT1 coding region of the nucleic acid sequence of SEQ ID NO: 1 or the complement thereof
wherein said nucleic acid molecule is operably linked to a heterologous promoter.

2. The substantially purified nucleic acid molecule according to claim 1, wherein said nucleic acid molecule encodes a protein comprising SEQ ID NO: 2.

3. The substantially purified nucleic acid molecule according to claim 1, wherein said promoter is a seed specific promoter.

4. The substantially purified nucleic acid molecule according to claim 3, wherein said seed specific promoter is a napin promoter or a 7S promoter.

5. The substantially purified nucleic acid molecule according to claim 1, wherein said promoter provides tissue-specific, cell-specific, or enhanced expression.

6. The substantially purified nucleic acid molecule according to claim 5, wherein said tissue is selected from the group consisting of tuber, fruit, leaf, seed, endosperm, ovule, pollen, aleurone, root, and stem.

7. The substantially purified nucleic acid molecule according to claim 5, wherein said promoter is selected from the group consisting of the nopaline synthase promoter, the octopine synthase promoter, the cauliflower mosaic virus 19S promoter, the cauliflower mosaic virus 35S promoter, the figwort mosaic virus 35S-promoter, the Adh promoter, the R gene complex promoter, the glutamine synthetase GS2 promoter, the fructose-1,6-biphosphatase (FBPase) promoter, the ST-LS1 promoter, the serine/threonine kinase promoter, the glucoamylase promoter, the ribulose-1,5-bisphosphate carboxylase (RbcS) promoter, the cab gene promoter, the Cab-1 promoter from wheat, the CAB-1 promoter from spinach, the cab1R promoter from rice, the pyruvate, orthophosphate dikinase (PPDK) promoter, the Lhcb1*2 promoter, the SUC2 sucrose-H+ symporter promoter, the LhcB promoter, the PsbP promoter, a class I patatin promoter, a class II patatin promoter, the potato tuber ADPGPP promoter, a chlorophyll a/b-binding protein promoter, a thylakoid membrane protein promoter, the tuber 22 kd protein complex promoter, tuber protease inhibitor promoters, the granule-bound starch synthase promoter, the phaseolin promoter, the soybean trypsin inhibitor promoter, the ACP promoter, stearoyl-ACP desaturase promoter, the soy 7S promoter, the β-conglycinin promoter, zein promoters, the waxy gene promoter, the Brittle gene promoter, the Shrunken 2 gene promoter, the branching enzyme I promoter, the branching enzyme II promoter, starch synthase promoters, debranching enzyme promoters, oleosin promoters, glutelin promoters, gliadin promoters, glutenin promoters, sucrose synthase promoters, the Osgt-1 promoter, the promoters for ADPglucose pyrosynthase subunits, embryogenesis-abundant protein promoters, hordein promoters, embryo globulin promoters, aleurone specific protein promoters arcelin 5, promoter the napin promoter, the acid chitinase promoter and the root specific subdomains of the CaMV35S promoter.

8. The nucleic acid molecule of claim 1 further defined as comprising a 3' non-translated sequence that functions in a plant cell to cause termination of transcription and addition of polyadenylated ribonucleotides to a 3' end of the mRNA molecule.

9. A transformed plant transformed with the substantially purified nucleic acid molecule of claim 1.

10. The transformed plant according to claim 9, wherein said substantially purified nucleic acid molecule comprises SEQ ID NO: 1.

11. The transformed plant according to claim 9, wherein said substantially purified nucleic acid molecule encodes a protein comprising SEQ ID NO: 2.

12. The transformed plant according to claim 9, wherein said plant is selected from the group consisting of alfalfa, *Arabidopsis*, barley, *Brassica campestris, Brassica napus*, broccoli, cabbage, citrus, canola, cotton, garlic, oat, onion, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, *Phaseolus*, crambe, mustard, castor bean, sesame, cottonseed, linseed, safflower, and oil palm.

13. The transformed plant according to claim 9, wherein said plant is selected from the group consisting of canola, maize, *Brassica campestris, Brassica napus*, soybean, crambe, mustard, castor bean, peanut, sesame, cottonseed, linseed, safflower, oil palm, flax and sunflower.

14. The transformed plant according to claim 9, wherein said plant is canola.

15. The transformed plant according to claim 9, wherein said plant is *Brassica napus*.

16. The transformed plant according to claim 9, wherein said plant is soybean.

17. The transformed plant according to claim 9, wherein said plant produces seeds with increased tocopherol levels relative to a plant with a similar genetic background but lacking said exogenous nucleic acid molecule.

18. The transformed plant according to claim 9, wherein said promoter is light inducible or provides tissue-specific, cell-specific, or enhanced expression in a tissue of tuber, fruit, leaf, seed, endosperm, ovule, pollen, aleurone, root, or stem.

19. The transformed plant according to claim 18, wherein said promoter is a seed specific promoter.

20. The transformed plant according to claim 19, wherein said seed specific promoter is selected from the group consisting of: soybean trypsin inhibitor promoter, stearoyl-ACP desaturase promoter, the soy 7S promoter, β-conglycinin promoter, zein promoters, the waxy gene promoter, the Brittle gene promoter, the Shrunken 2 gene promoter, the promoter for branching enzyme I, the promoter for branching enzyme II, a starch synthase promoter, a debranching enzyme promoter, oleosin promoters, glutelin promoters sucrose synthase promoters, the Osgt-1 promoter, ADPglucose pyrosynthase subunit promoters, the granule bound and other starch synthase promoters, the embryogenesis-abundant protein promoters, gliadin promoters, glutenin promoters, hordein promoters, embryo globulin promoters, the aleurone specific protein promoters, arcelin 5, promoter and the napin promoter.

21. A method of producing a plant having seeds with an increased tocopherol level comprising: (A) transforming said plant with the substantially purified nucleic acid molecule of claim 1; and (B) growing said plant.

22. The method of producing a plant according to claim 21, wherein said plant is selected from the group consisting of alfalfa, *Arabidopsis*, barley, *Brassica campestris, Brassica napus*, broccoli, cabbage, canola, citrus, cotton, garlic, oat, onion, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, *Phaseolus*, crambe, mustard, castor bean, sesame, cottonseed, linseed, safflower, and oil palm.

23. The method according to claim 21, wherein said plant is selected from the group consisting of canola, maize, *Brassica campestris, Brassica napus*, soybean, crambe, mustard, castor bean, peanut, sesame, cottonseed, linseed, safflower, oil palm, flax, and sunflower.

24. The method according to claim 21, wherein said plant is canola.

25. The method according to claim 21, wherein said plant is *Brassica napus*.

26. The method according to claim 21, wherein said plant is soybean.

27. The method according to claim 21, wherein said plant produces seeds, wherein said tocopherol level is increased at least 10% relative to plants with similar genetic background but lacking said nucleic acid molecule.

28. The method according to claim 21, wherein said plant produces seeds, wherein said tocopherol level is increased at least 20% relative to plants with similar genetic background but lacking said nucleic acid molecule.

29. The method according to claim 21, wherein said plant produces seeds, wherein said tocopherol level is increased at least 30% relative to plants with similar genetic background but lacking said nucleic acid molecule.

30. The method according to claim 21, wherein said plant produces seeds, wherein said tocopherol level is increased at least 40% relative to plants with similar genetic background but lacking said nucleic acid molecule.

31. A seed of the plant of claim 9, wherein said seed has an increased tocopherol level relative to seeds from a plant having a similar genetic background but lacking said exogenous nucleic acid molecule.

32. Feedstock comprising the transformed plant of claim 9 or part thereof.

33. The feedstock of claim 32, wherein said plant produces seeds with increased tocopherol levels relative to a plant with a similar genetic background but lacking said exogenous nucleic acid molecule.

34. A meal comprising plant material manufactured from the transformed plant of claim 9.

35. The meal according to claim 34, wherein said transformed plant produces seeds with increased tocopherol levels relative to a plant with a similar genetic background but lacking said exogenous nucleic acid molecule.

36. The substantially purified nucleic acid molecule of claim 1 wherein said purified nucleic acid molecule further comprises one or more expression cassettes, each of which expresses a member selected from the group consisting of slr1736, ATPT2, dxs, dxr, GGH, GGPPS, HPPD, MT1, TMT2, GMT, slr 1737, and an antisense construct for homogentisic acid dioxygenase.

37. The substantially purified nucleic acid molecule according to claim 36, wherein said nucleic acid sequence that encodes an adenylate transporter encodes the protein product of the AANT1 gene.

38. The transgenic plant of claim 9, wherein said plant further comprises one or more expression cassettes, each of which expresses a member selected from the group consisting of slr1736, ATPT2, dxs, dxr, GGH, GGPPS, HPPD, MT1, TMT2, GMT, slr 1737, and an antisense construct for homogentisic acid dioxygenase.

\* \* \* \* \*

UNITED STATES PATENT AND TRADEMARK OFFICE
CERTIFICATE OF CORRECTION

PATENT NO. : 7,161,061 B2  Page 1 of 1
APPLICATION NO. : 10/141478
DATED : January 9, 2007
INVENTOR(S) : Valentin et al.

It is certified that error appears in the above-identified patent and that said Letters Patent is hereby corrected as shown below:

In claim 7, column 58, line 66, please delete "the pyruvate," and insert --the pyruvate--.

In claim 7, column 59, lines 19-20, please delete "promoters arcelin 5, promoter the napin promoter" and insert --promoters, arcelin 5 promoter, the napin promoter--.

In claim 18, column 59, line 64, please delete "alcurone" and insert --aleurone--.

In claim 20, column 60, line 15, please delete "arcelin 5, promoter" and insert -- arcelin 5 promoter, --.

In claim 36, column 61, line 12, please delete "slf 1737" and insert --slf1737--.

In claim 38, column 62, line 10, please delete "slf 1737" and insert --slf1737--.

Signed and Sealed this

Fifteenth Day of May, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 1458
<212> TYPE: DNA
<213> ORGANISM: Arabidopsis thaliana

<400> SEQUENCE: 1

```
gataaaggcg gagtctctct ccagttattt tgctcatcca tcgattctta gagttcaaaa      60
tggttgatca agttcagcac cccactattg cgcagaaagc tgccgggcag ttcatgcgtt     120
caagtgtttc caaggacgtt caagtgggtt accagaggcc ttctatgtat caaagacatg     180
caacctacgg aaactactcc aatgctgcat ttcaatttcc tccgacatcc cggatgttgg     240
caacaactgc ttctcccgtg tttgtccaaa ccccaggaga gaagggttc actaactttg      300 cccttgactt tctgatgggt ggtgtttctg ctgccgtctc caagactgct gctgctccta     360
ttgaacgtgt taagcttttg atccagaacc aggatgagat gattaaagct ggcaggcttt     420
ctgaacccta caagggtatt ggtgactgtt tcggcaggac gattaaggat gaaggttttg     480
gttctctatg gagaggaaac actgccaatg ttatccgtta tttccccact caggccttga     540
actttgcctt caaagattac ttcaaaagac ttttcaactt taagaaggac agagatggtt     600
actggaagtg gtttgctggt aacttggcat ctggaggagc agctggtgcc tcttcccttc     660
tgtttgtgta ctcccttgac tatgcccgta cccgtctagc taatgatgcc aaggctgcaa     720
agaaaggagg tggtggaaga cagtttgatg gtcttgttga tgtctacaga aagacactta     780
agactgatgg tattgctggt ctgtaccgtg gattcaacat ctcatgtgtt ggtatcattg     840
```

```
tctaccgtgg tctgtacttt ggactctatg actctgtgaa gcctgttctc ctcactggtg    900
acttacagga cagtttcttc gctagtttcg ctcttggatg ggttattacc aatggtgcgg    960
gtcttgcatc ctaccccatt gacactgtcc gcagaagaat gatgatgacg tctaatgaag   1020
ctgtcaagta caagagttct ttggacgcct tcaagcagat cctcaagaat gaaggagcca   1080
agtcactctt caagggagct ggtgccaaca ttctgcgtgc tgttgcaggt gctggtgtgc   1140
tttccggtta cgacaaattg actctgattg tcttcggtaa gaagtacgga tcaggaggtg   1200
cctaagcatg cttcttcctc cttttcgatt taattgcggt ttaaggcccg caataaactg   1260
agatgttgat gaattttttt ttgcttaaga cttagggagc atgtgcccta aaccaaattt   1320
tatatcgttc tgacgccaac tttttttact tatggaataa ttcatgtttg agagagtttg   1380
ttagactctt cgatttttaaa gaattttgga tttatgaaat aaattcttct tttttaaaaa   1440
aaaaaaaaaa aaaaaaaa                                                 1458
```

<210> SEQ ID NO 2
<211> LENGTH: 381
<212> TYPE: PRT
<213> ORGANISM: Arabidopsis thaliana

<400> SEQUENCE: 2

```
Met Val Asp Gln Val Gln His Pro Thr Ile Ala Gln Lys Ala Ala Gly
1               5                   10                  15

Gln Phe Met Arg Ser Val Ser Lys Asp Val Gln Val Gly Tyr Gln
            20                  25                  30

Arg Pro Ser Met Tyr Gln Arg His Ala Thr Tyr Gly Asn Tyr Ser Asn
        35                  40                  45

Ala Ala Phe Gln Phe Pro Pro Thr Ser Arg Met Leu Ala Thr Thr Ala
    50                  55                  60

Ser Pro Val Phe Val Gln Thr Pro Gly Glu Lys Gly Phe Thr Asn Phe
65                  70                  75                  80

Ala Leu Asp Phe Leu Met Gly Gly Val Ser Ala Val Ser Lys Thr
                85                  90                  95

Ala Ala Ala Pro Ile Glu Arg Val Lys Leu Leu Ile Gln Asn Gln Asp
            100                 105                 110

Glu Met Ile Lys Ala Gly Arg Leu Ser Glu Pro Tyr Lys Gly Ile Gly
        115                 120                 125

Asp Cys Phe Gly Arg Thr Ile Lys Asp Glu Gly Phe Gly Ser Leu Trp
    130                 135                 140

Arg Gly Asn Thr Ala Asn Val Ile Arg Tyr Phe Pro Thr Gln Ala Leu
145                 150                 155                 160

Asn Phe Ala Phe Lys Asp Tyr Phe Lys Arg Leu Phe Asn Phe Lys Lys
                165                 170                 175

Asp Arg Asp Gly Tyr Trp Lys Trp Phe Ala Gly Asn Leu Ala Ser Gly
            180                 185                 190

Gly Ala Ala Gly Ala Ser Ser Leu Leu Phe Val Tyr Ser Leu Asp Tyr
        195                 200                 205

Ala Arg Thr Arg Leu Ala Asn Asp Ala Lys Ala Ala Lys Lys Gly Gly
    210                 215                 220

Gly Gly Arg Gln Phe Asp Gly Leu Val Asp Val Tyr Arg Lys Thr Leu
225                 230                 235                 240

Lys Thr Asp Gly Ile Ala Gly Leu Tyr Arg Gly Phe Asn Ile Ser Cys
                245                 250                 255
```

```
Val Gly Ile Ile Val Tyr Arg Gly Leu Tyr Phe Gly Leu Tyr Asp Ser
            260                 265                 270

Val Lys Pro Val Leu Leu Thr Gly Asp Leu Gln Asp Ser Phe Phe Ala
        275                 280                 285

Ser Phe Ala Leu Gly Trp Val Ile Thr Asn Gly Ala Gly Leu Ala Ser
    290                 295                 300

Tyr Pro Ile Asp Thr Val Arg Arg Arg Met Met Met Thr Ser Asn Glu
305                 310                 315                 320

Ala Val Lys Tyr Lys Ser Ser Leu Asp Ala Phe Lys Gln Ile Leu Lys
            325                 330                 335

Asn Glu Gly Ala Lys Ser Leu Phe Lys Gly Ala Gly Ala Asn Ile Leu
            340                 345                 350

Arg Ala Val Ala Gly Ala Gly Val Leu Ser Gly Tyr Asp Lys Leu Thr
            355                 360                 365

Leu Ile Val Phe Gly Lys Lys Tyr Gly Ser Gly Gly Ala
            370                 375                 380

<210> SEQ ID NO 3
<211> LENGTH: 37
<212> TYPE: DNA
<213> ORGANISM: artificial sequence
<220> FEATURE:
<223> OTHER INFORMATION: synthetic primer

<400> SEQUENCE: 3
ggatccgcgg ccgcaccatg gttgatcaag ttcagca                            37

<210> SEQ ID NO 4
<211> LENGTH: 39
<212> TYPE: DNA
<213> ORGANISM: artificial sequence
<220> FEATURE:
<223> OTHER INFORMATION: synthetic primer

<400> SEQUENCE: 4
gagctcctgc aggaagcttt taggcacctc ctgatccgt                          39
```